(12) United States Patent
Liu

(10) Patent No.: US 10,960,086 B2
(45) Date of Patent: Mar. 30, 2021

(54) APTAMER COMPOSITIONS AND METHODS OF USE THEREOF

(71) Applicant: Augusta University Research Institute, Inc., Augusta, GA (US)

(72) Inventor: Hong Yan Liu, Martinez, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 10 days.

(21) Appl. No.: 16/234,710

(22) Filed: Dec. 28, 2018

(65) Prior Publication Data

US 2019/0201552 A1 Jul. 4, 2019

Related U.S. Application Data

(60) Provisional application No. 62/738,236, filed on Sep. 28, 2018, provisional application No. 62/611,292, filed on Dec. 28, 2017.

(51) Int. Cl.
| | | |
|---|---|---|
| *A61K 48/00* | (2006.01) | |
| *A61P 35/00* | (2006.01) | |
| *C12N 15/115* | (2010.01) | |
| *A61P 31/12* | (2006.01) | |
| *C12N 15/113* | (2010.01) | |

(52) U.S. Cl.
CPC .......... *A61K 48/0066* (2013.01); *A61P 31/12* (2018.01); *A61P 35/00* (2018.01); *C12N 15/113* (2013.01); *C12N 15/115* (2013.01); *C12N 15/1138* (2013.01); *C12N 2310/14* (2013.01); *C12N 2310/16* (2013.01); *C12N 2310/3519* (2013.01); *C12N 2310/531* (2013.01)

(58) Field of Classification Search
None
See application file for complete search history.

(56) References Cited

U.S. PATENT DOCUMENTS

| 6,162,432 A | 12/2000 | Wallner et al. | |
|---|---|---|---|
| 2013/0102654 A1* | 4/2013 | Rossi .................... | C12N 15/111 514/44 A |

FOREIGN PATENT DOCUMENTS

| WO | 93/08656 | 4/1993 |
|---|---|---|
| WO | 02/44321 | 6/2002 |
| WO | 02/069904 | 9/2002 |
| WO | 02/098370 | 12/2002 |

OTHER PUBLICATIONS

Arteaga, Carlos L. et al., "ERBB Receptors: From Oncogene Discovery to Basic Science to Mechanism-Based Cancer Therapeutics", Cancer Cell, 25: 282-303 (2014).

Barnd, Donna L. et al., "Specific, Major Histocompatibility Complex-Unrestricted Recognition of tumor-associated Mucins by Human Cytotoxic T Cells", Proc. Nat. Acad. Sci. USA, 86:7159 (1989).
Bast, Robert C. et al., "A Radioimmunoassay Using a Monoclonal Antibody to Monitor the Course of Epithelial Ovarian Cancer", N. Eng. J. Med., 309:883 (1983). Abstract Only.
Bernstein, Emily et al., "Role for a Bidentate Ribonuclease in the Initiation Step of RNA Interference", Nature,409:363-366 (2001).
Chen, Chi-Hong B. et al., "Inhibition of Heregulin Signaling by an Aptamer that Preferentially Binds to the Oligomeric Form of Human Epidermal Growth Factor Receptor-3", Proc Natl Acad Sci USA, 100:9226-9231 (2003).
Dassie, Justin P. et al., "Systemic Administration of Optimized Aptamer-siRNA Chimeras Promotes Regression of PSMA-Expressing Tumors", Nat Biotechnol, 27:839-849 (2009).
Dassie, Justin P. et al., "Current Progress on Aptamer-Targeted Oligonucleotide Therapeutics", Ther Deiv, 4:1527-1546 (2013).
Dua, R. et al., "EGFR Over-Expression and Activation in High HER2, ER Negative Breast Cancer Cell Line Induces Trastuzumab Resistance", Breast Cancer Res Treat, 122:685-697 (2010). Abstract Only.
Elbashir Sayda M. et al., "RNA Interference is Mediated by 21- and 22-Nucleotide RNAs", Genes Dev., 15:188-200 (2001).
Ellington Andrew D. et al., "In Vitro Selection of RNA Molecules that Bind Specific Ligands", Nature, 346: 818-822 (1990).
Gebauer, Gerhard et al., "Tumor Marker Concentrations in Normal and Malignant Tissues of Colorectal Cancer Patients and their Prognostic Relevance", Anticancer Res., 17(4B):2939 (1997).
Hammond, Scott M. et al., "An RNA-Directed Nuclease Mediates Post-Transcriptional Gene Silencing in *Drosophila* Cells", Nature, 404:293-296 (2000).
Hannon, Gregory J. et al., "RNA Interference", Nature, 418:244-251 (2002).
Hermann, Andreas et al., "CTLA4 Aptamer Delivers STAT3 siRNA to Tumor-Associated and Malignant T Cells", J Clin Invest, 124: 2977-2987 (2014).
Hirokawa, Shinichiro et al., "Neuroblastoma in an Adult with a High Serum Level of Carbohydrate Antigen, CA125: Report of a Case", Surg. Today, 28:349 (1998).
Holbro, Thomas et al., "The ErbB2/ErbB3 Heterodimer Functions as an Oncogenic Unit: ErbB2 Requires ErbB3 to Drive Breast Tumor Cell Proliferation", Proc Natl Acad Sci USA, 100:8933-8938 (2003).
Hu, Shi et al., "Four-in-One Antibodies Have Superior Cancer Inhibitory Activity Against EGFR, HER2, HER3, and VEGF Through Disruption of HER/MET Crosstalk", Cancer Res, 75:159-170 (2015).
Hussain, Ahmad Fawzi et al., "An Aptamer-siRNA Chimera Silences the Eukaryotic Elongation Factor 2 Gene and Induces Apoptosis in Cancers Expressing ?V β3 Integrin", Nucleic Acid Ther, 23:203-212 (2013).

(Continued)

*Primary Examiner* — Tracy Vivlemore
(74) *Attorney, Agent, or Firm* — Smith, Gambrell & Russell LLP; Charles Vorndran; Ram W. Sabnis

(57) ABSTRACT

An aptamer platform capable of efficiently delivering and silencing one, two or more genes in vivo or in vitro is provided. Methods of using the aptamer compositions for selectively targeting cells to down-regulate the expression of multiple genes are also provided.

7 Claims, 56 Drawing Sheets

Specification includes a Sequence Listing.

(56) References Cited

OTHER PUBLICATIONS

Iida, Mari et al., "Targeting the HER Family with Pan-HER Effectively Overcomes Resistance to Cetuximab", Mol Cancer Ther, 15:2175-2186 (2016).
Jacobsen Helle J. et al., "Pan-HER, an Antibody Mixture Simultaneously Targeting EGFR, HER2, and HER3, Effectively Overcomes Tumor Heterogeneity and Plasticity", Clin Cancer Res, 21:4110-4122 (2015).
Jensen, Samuel A., et al., "Spherical Nucleic Acid Nanoparticle Conjugates as an RNAi-Based Therapy for Glioblastoma", Sci Transl Med, 5: 209ra152 (2013).
Keefe, Anthony D., et al., "Aptamers as Therapeutics", Nat Rev Drug Discov, 9:537-550 (2010).
Kim, Dong-Ho et al., "Interferon Induction by siRNAs and ssRNAs Synthesized by Phage Polymerase", Nat Biotechnol, 22: 321-325 (2004).
Kim, Mee Young et al., "In Vitro Selection of RNA Aptamer and Specific Targeting of ErbB2 in Breast Cancer Cells", Nucleic Acid Ther, 21:173-178 (2011).
Kontermann, Roland E. et al., "Bispecific Antibodies", Drug Discov Today, 20:838-847 (2015).
Kudoh, K. et al., "Preoperative Determination of Several Serum Tumor Markers in Patients with Primary Epithelial Ovarian Carcinoma", Gynecol. Obstet. Invest., 47:52 (1999). Abstract Only.
Lee-Hoeflich, Si Tuen et al., "A Central Role for HER3 in HER2-Amplified Breast Cancer: Implications for Targeted Therapy", Cancer Res, 68:5878-5887 (2008).
Liu, Hong Yan et al., "Co-Targeting EGFR and Survivin with a Bivalent Aptamer-Dual siRNA Chimera Effectively Suppresses Prostate Cancer", Sci Rep, 6:30346 (2016).
Lloyd, Kenneth O. et al., "Isolation and Characterization of Ovarian Cancer Antigen CA 125 Using a New Monoclonal Antibody (VK-8): Identification as a Mucin-Type Molecule", Int. J. Canc., 71:842 (1997).
Ma, Jin-Biao et al., "Structural Basis for Overhang-Specific Small Interfering RNA Recognition by the PAZ Domain", Nature, 429:318-322 (2004).
Martinez, Javier et al., "Single-Stranded Antisense siRNAs Guide Target RNA Cleavage in RNAi", Cell, 110:563-574 (2002).
Meier, Werner et al., "Prognostic Significance of CA125 in Patients with Ovarian Cancer and Secondary Debulking Surgery", Anticancer Res., 17(4B):2945 (1997).
Narayan Murli et al., "Trastuzumab-Induced HER Reprogramming in "Resistant" Breast Carcinoma Cells", Cancer Res, 69:2191-2194 (2009).
Neff, Charles Preston et al., "An Aptamer-siRNA Chimera Suppresses HIV-1 Viral Loads and Protects from Helper CD4+ T Cell Decline in Humanized Mice", Sci Transl Med, 3:66ra6 (2011). Abstract Only.
Nicholson, R.I., et al., "EGFR and Cancer Prognosis", Eur J Cancer, 37: S9-S15 (2001).
Olayioye Monilola A. et al., "The ErbB Signaling Network: Receptor Heterodimerization in Development and Cancer", EMBO, 19:3159-3167 (2000).
Ritter, Christoph A. et al., "Human Breast Cancer cells Selected for Resistance to Trastuzumab In Vivo Overexpress Epidermal Growth Factor Receptor and ErbB Ligands and Remain Dependent on the ErbB Receptor Network", Clin Cancer Res, 13:4909-4919 (2007).
Sarandakou, Angeliki et al., "Vaginal Fluid and Serum CEA, CA125 and SCC in Normal Conditions and in Benign and Malignant Diseases of the Genital Tract", Acta Oncol., 36:755 (1997).
Sarandakou, A., et al., "Tumour-Associated Antigens CEA, CA125, SCC and TPS in Gynaecological Cancer", Eur. J. Gynaecol. Oncol., 19:73 (1998).
Siomi Haruhiko et al., "On the Road to Reading the RNA-Interference Code", Nature, 457:396-404 (2009).
Slamon, D.J. et al., "Human Breast Cancer: Correlation of Relapse and Survival with Amplification of the HER-2/neu Oncogene", Science, 235:177-182 (1987). Abstract Only.
Takahashi, Mayumi et al., "High Throughput Sequencing Analysis of RNA Libraries Reveals the Influences of Initial Library and PCR Methods on SELEX Efficiency", Sci Rep, 6:33697 (2016).
Trowbridge, Ian S. et al., "Human Cell Surface Glycoprotein Related to Cell Proliferation is the Receptor for Transferrin", Proc. Nat. Acad. USA, 78:3039 (1981).
Tuerk, Craig et al., "Systematic Evolution of Ligands by Exponential Enrichment: RNA Ligands to Bacteriophage T4 DNA Polymerase", Science, 249:505-510 (1990).
Ui-Tei, Kumiko et al., "Sensitive Assay of RNA Interference in *Drosophila* and Chinese Hamster Cultured Cells Using Firefly Luciferase Gene as Target", FEBS Letters, 479:79-82 (2000).
Wang, Tao et al., "EpCAM Aptamer-Mediated Survivin Silencing Sensitized Cancer stem Cells to Doxorubicin in a Breast Cancer Model", Theranostics, 5:1456-1472 (2015).
Wheeler, Deric L., et al., "Mechanisms of Acquired Resistance to Cetuximab: Role of HER (ErbB) Family Members", Oncogene, 27:3944-3956 (2008).
Wheeler, Lee Adam et al., "Inhibition of HIV Transmission in Human Cervicovaginal Explants and Humanized Mice Using CD4 Aptamer-siRNA Chimeras", J Clin Inves, 121:2401-2412 (2011).
Whitehead, Kathryn A., et al., "Knocking Down Barriers: Advances in siRNA Delivery", Nat Rev Drug Discov, 8: 129-138 (2009).
Wu, Sherry Y. et al., "Targeting the Undruggable: Advances and Obstacles in Current RNAi Therapy", Sci Transl Med, 6:240ps7 (2014).
Xiao, Zhan et al., "A Potent HER3 Monoclonal Antibody that Blocks Both Ligand-Dependent and -Independent Activities: Differential Impacts of PTEN Status on Tumor Response", Mol Cancer Ther, 15:689-701 (2016).
Zheng, Jingying et al., "Simultaneous Targeting of CD44 and EpCAM with a Bispecific Aptamer Effectively Inhibits Intraperitoneal Ovarian Cancer Growth", Theranostics, 7:1373-1388 (2017).
Zhou, Jiehua et al., "Novel Dual Inhibitory Function Aptamer-siRNA Delivery System for HIV-1 Therapy", Mol Ther, 16:1481-1489 (2008).
Zhou, Jiehua et al., "Development of Cell-Type Specific Anti-HIV gp120 Aptamers for siRNA Delivery", J Vis Exp, 52:e2954 (2011).
Zhou, Jiehua et al., "Current Progress of RNA Aptamer-Based Therapeutics", Front Genet, 3:234 (2012).
Zhou, Jiehua et al., "Aptamers as Targeted Therapeutics: Current Potential and Challenges", Nat Drug Rev Discov, 16:181-202 (2017).

\* cited by examiner

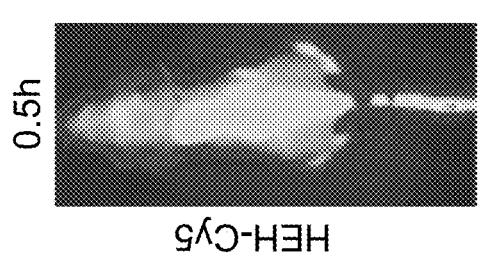
FIG. 5F  HEH-Cy5  0.5h
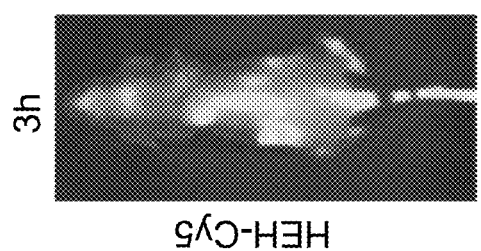
FIG. 5G  HEH-Cy5  3h
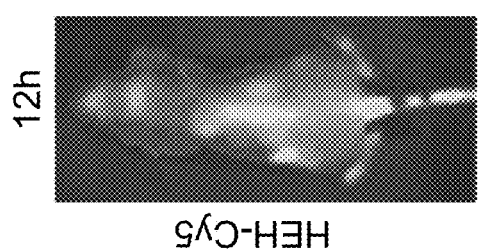
FIG. 5H  HEH-Cy5  12h
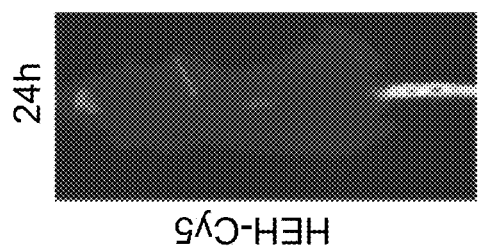
FIG. 5I  HEH-Cy5  24h
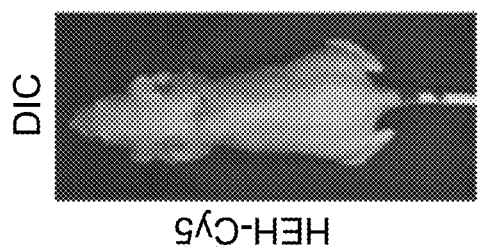
FIG. 5J  HEH-Cy5  DIC
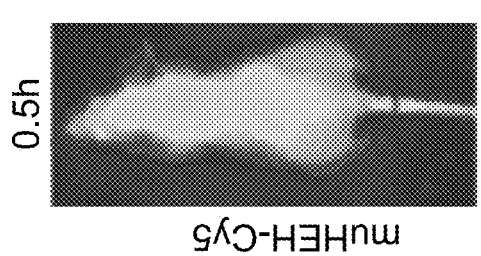
FIG. 5K  muHEH-Cy5  0.5h
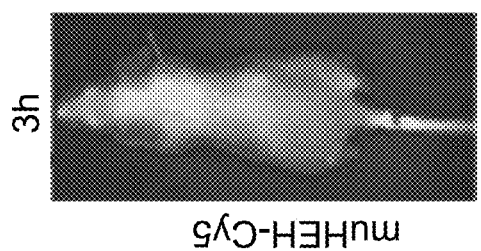
FIG. 5L  muHEH-Cy5  3h
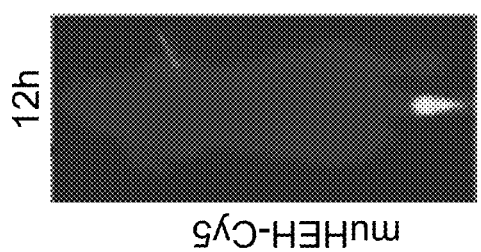
FIG. 5M  muHEH-Cy5  12h
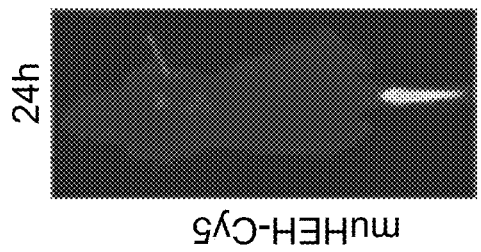
FIG. 5N  muHEH-Cy5  24h
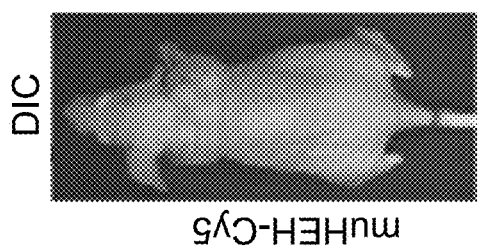
FIG. 5O  muHEH-Cy5  DIC

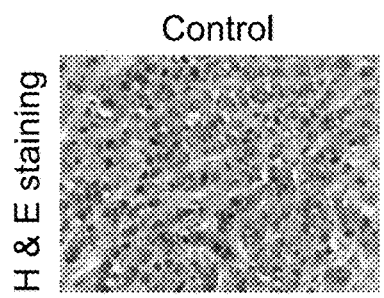
Control
H & E staining
FIG. 7A
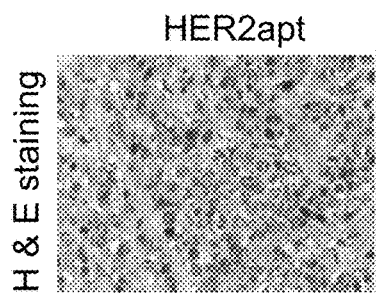
HER2apt
H & E staining
FIG. 7B
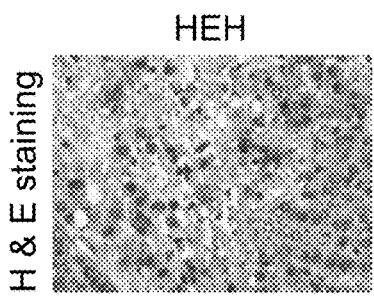
HEH
H & E staining
FIG. 7C
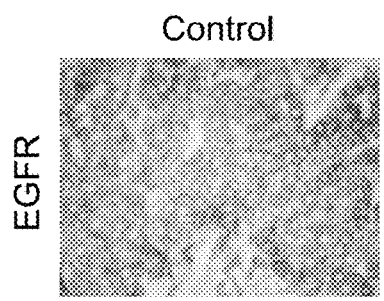
Control
EGFR
FIG. 7D
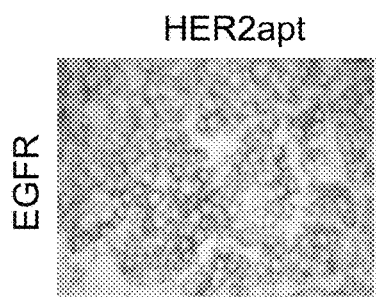
HER2apt
EGFR
FIG. 7E
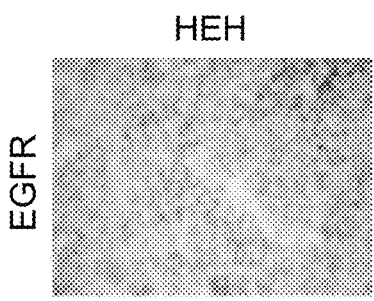
HEH
EGFR
FIG. 7F
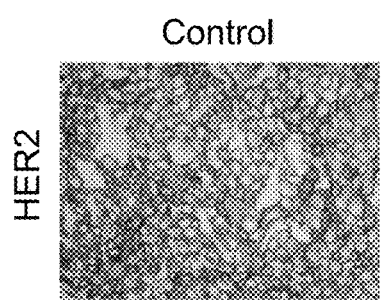
Control
HER2
FIG. 7G
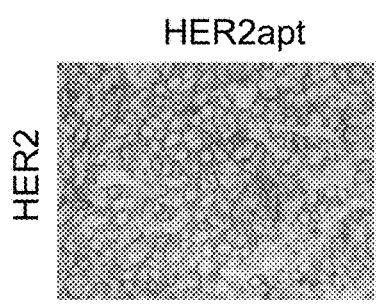
HER2apt
HER2
FIG. 7H
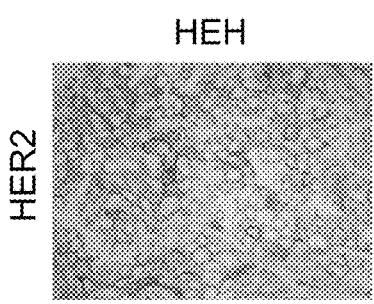
HEH
HER2
FIG. 7I
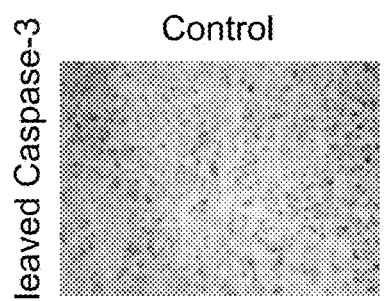
Control
Cleaved Caspase-3
FIG. 7J
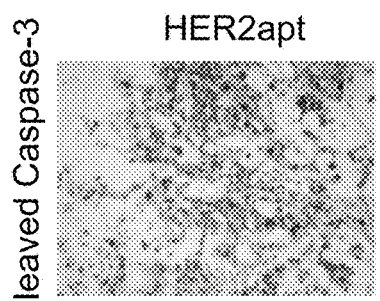
HER2apt
Cleaved Caspase-3
FIG. 7K
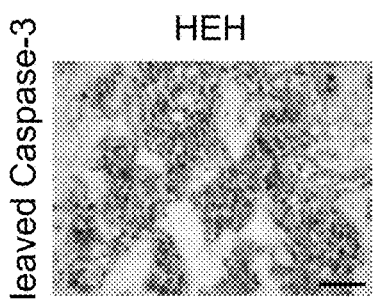
HEH
Cleaved Caspase-3
FIG. 7L  50μm

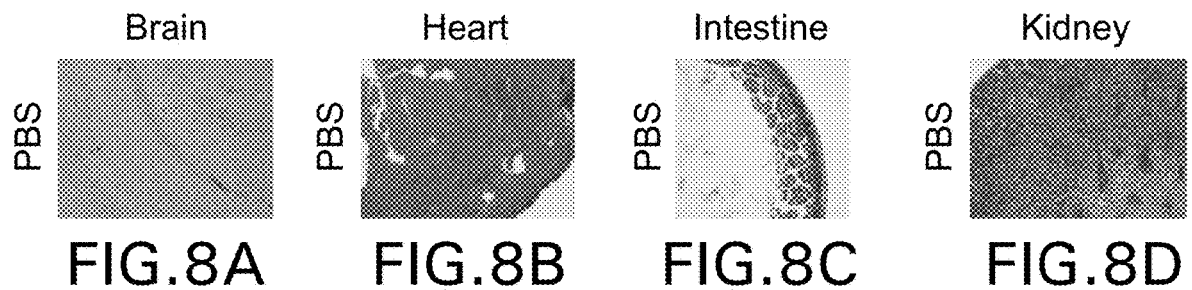
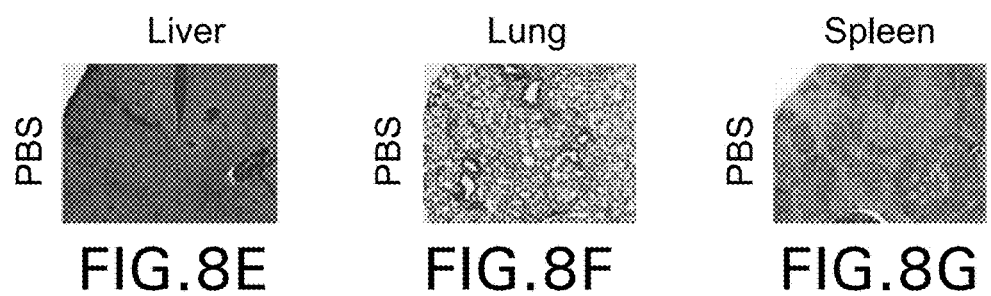
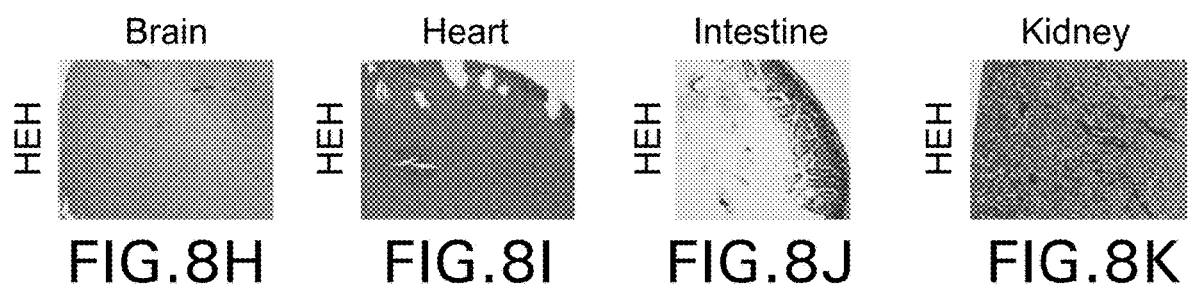
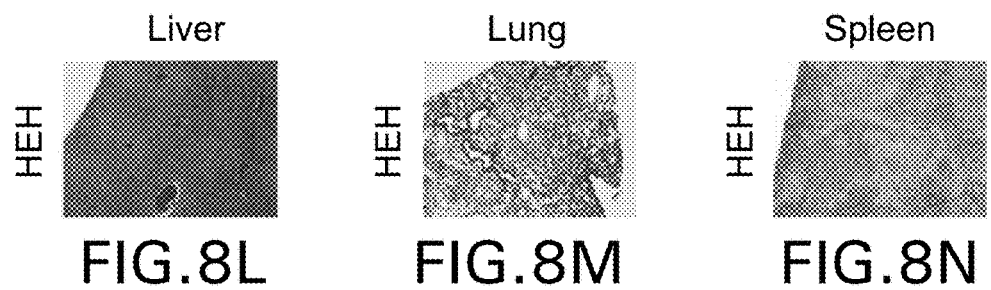

1. MW marker
2. HER2 apt-EGFR siRNA sense strand
3. Annealed HEH
4. HER2 apt-EGFR siRNA anti-sense strand

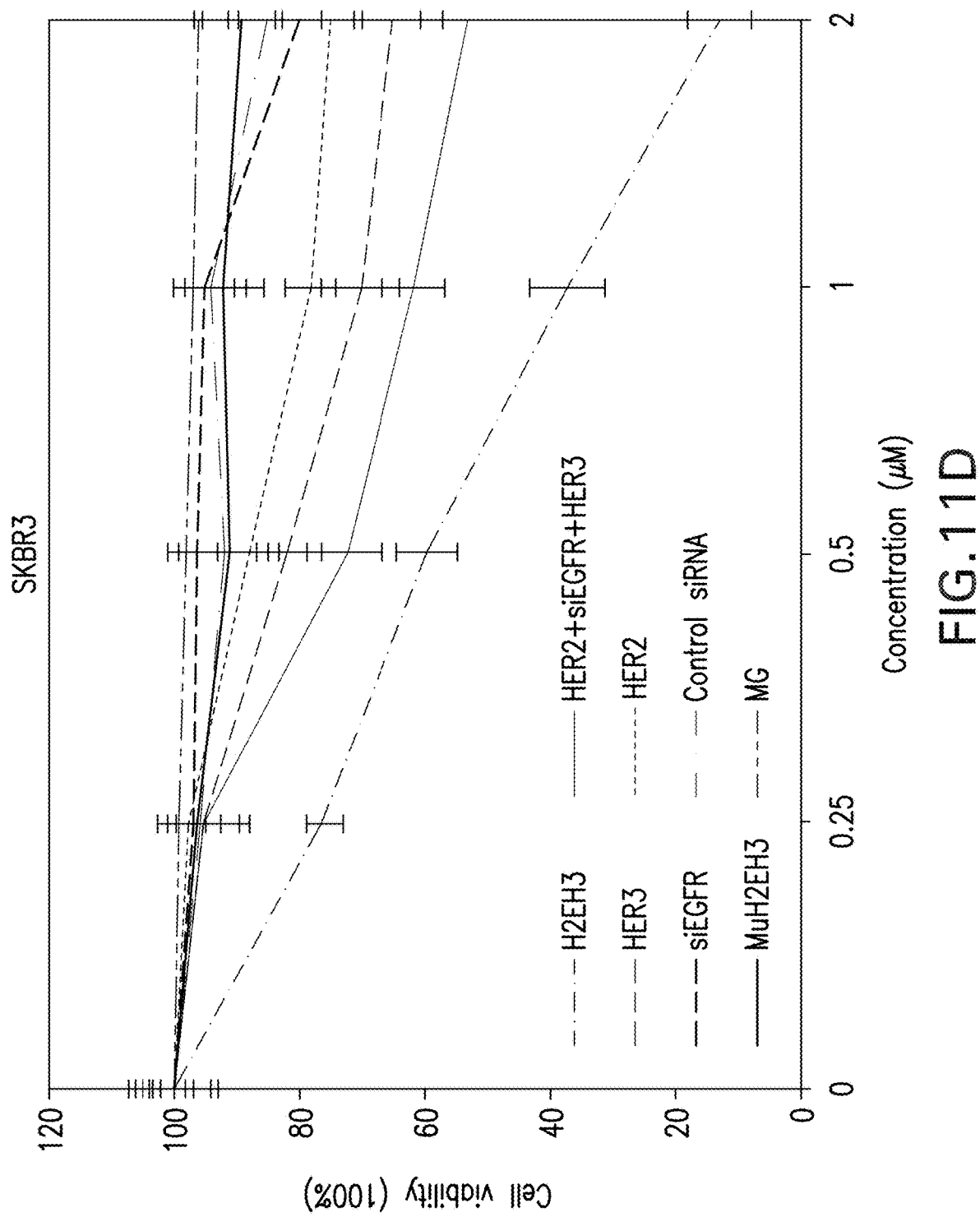

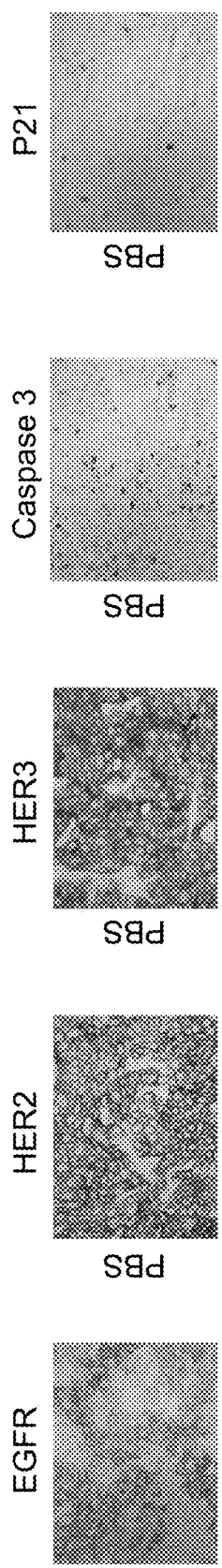
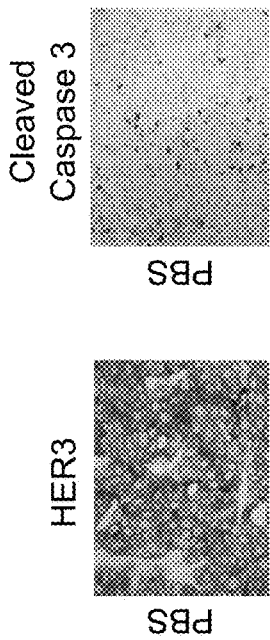
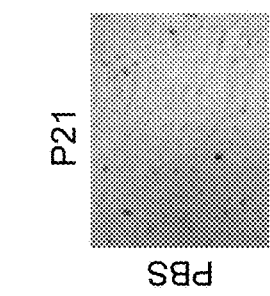
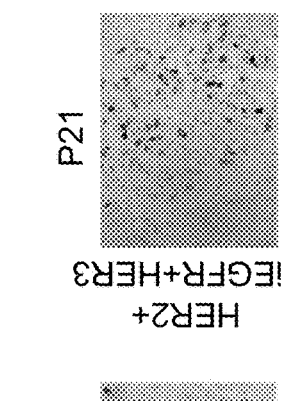
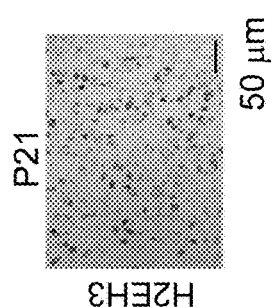
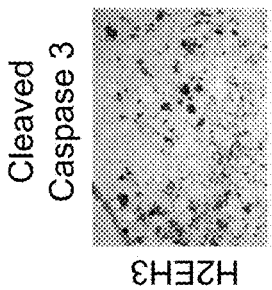
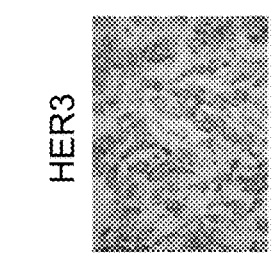
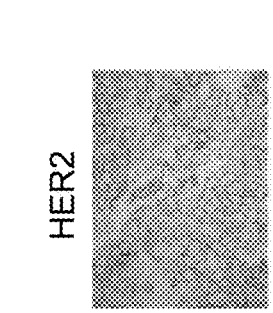
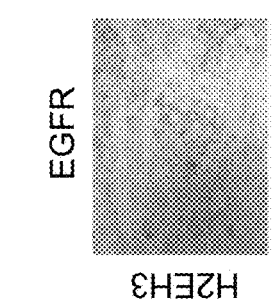

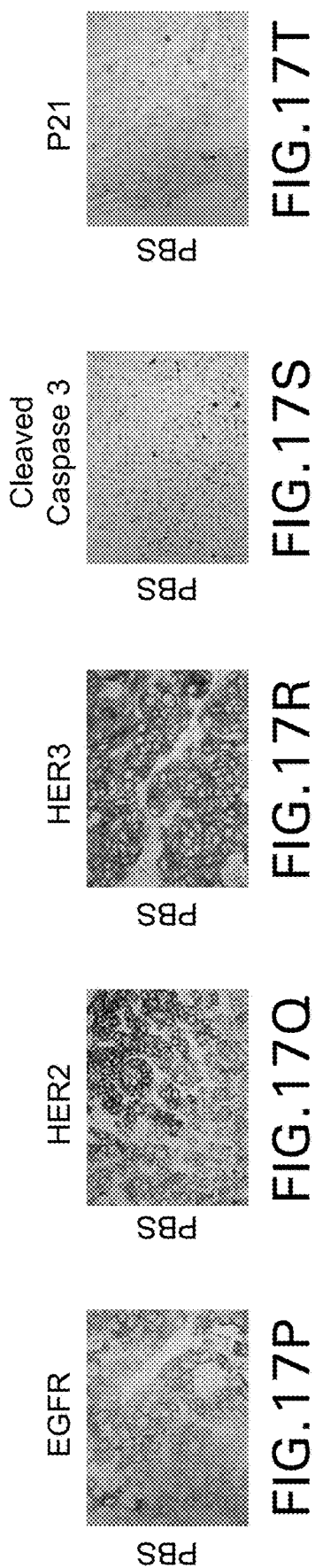
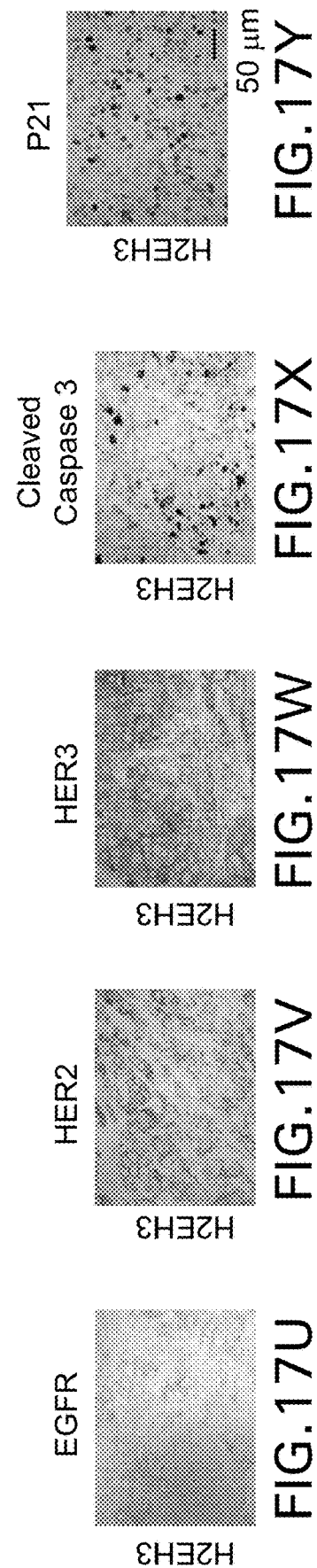

100 μm

APTAMER COMPOSITIONS AND METHODS OF USE THEREOF

CROSS-REFERENCE TO RELATED APPLICATIONS

This application claims benefit of and priority to U.S. Provisional Application No. 62/611,292 filed on Dec. 28, 2017 and 62/738,236 filed on Sep. 28, 2018, both of which are incorporated by reference in their entirety.

STATEMENT REGARDING FEDERALLY SPONSORED RESEARCH

This invention was made with government support under W81XWH-15-1-0333 awarded by the US Army Medical Research and Material Command. The government has certain rights in the invention.

REFERENCE TO SEQUENCE LISTING

The Sequence Listing submitted on Jun. 29, 2020, as a text file name "064466.082_selisting_replacement.txt" created on Jun. 23, 2020, and having a size of 7.36 KB is hereby incorporated by reference pursuant to 37 C.F.R. § 1.52 (e)(5).

FIELD OF THE INVENTION

The invention is generally directed to nucleic acid compositions for inhibiting gene expression in targeted cells.

BACKGROUND OF THE INVENTION

Twenty to thirty percent of breast cancer is characterized with HER2 overexpression that correlates with poor prognosis, high aggressiveness, and extensive drug resistance (Slamon, et al., Science, 235:177-182 (1987)). Trastuzumab (Herceptin®), a humanized antibody, is the first line treatment for patients with HER2 positive breast cancer. However, the majority of patients eventually develop resistance.

The resistance to HER2 targeted therapies is associated with the increased levels of other HER family receptors (Narayan, et al., Cancer Res, 69: 2191-2194 (2009)). The HER family consists of EGFR (HER1), HER2, HER3 and HER4 (Arteaga, et al., Cancer Cell, 25: 282-303 (2014)). It is well known that the HER family is interdependent and displays functional redundancy in that the blockade of one HER receptor can often be compensated by another HER family member (Olayioye, et al., EMBO, 19: 3159-3167 (2000)). EGFR, HER2 and HER3 contribute to the initiation and progression of many cancers, and are well recognized therapeutic targets.

Ligand binding to HER receptors results in the formation of homo- and hetero-dimers. EGFR is one of the most studied. HER-family receptors and a key oncogenic driver in many epithelial cancers (Nicholson, et al., Eur J Cancer, 37: S9-S15 (2001)). Accumulating evidence shows that HER3 is a key node in many cancers and involved in the resistance against EGFR- and HER2-targeted therapies through activating a compensatory PI3K-AKT survival pathway (Lee-Hoeflich, et al., Cancer Res, 68: 5878-5887 (2008); Holbro, et al., Proc Natl Acad Sci USA, 100: 8933-8938 (2003)). Resistance to trastuzumab in breast cancer cell lines is associated with upregulation of EGFR and HER3 (Narayan, et al., Cancer Res, 69: 2191-2194. (2009); Ritter, et al., Clin Cancer Res, 13: 4909-4919 (2007)).

HER2/HER3 heterodimer has been identified to function like an oncogene to support the proliferation of HER2-overexpressing tumor cells (Holbro, et al., Proc Natl Acad Sci USA, 100: 8933-8938 (2003)). The cross-talk and compensatory functionalities of HER family receptors provide strong rationales for co-targeting of EGFR, HER2 and HER3 in HER-dependent cancer treatment. In line with the notion of combining treatment, bi-specific antibodies and pan-HER antibodies have been developed and show more efficacious than single receptor targeting antibodies. Bispecific MM11 antibody targeting both HER2 and HER3 is able to suppress the proliferation of HER2-expressing tumor cells (Kontermann, et al., Drug Discov Today, 20:838-847 (2015)). Pan-HER with six antibody mixture targeting EGFR, HER2 and HER3 has been developed and displayed superior potency compared to agents targeting single receptors in preclinical studies (Jacobsen, et al., Clin Cancer Res, 21: 4110-4122 (2015)).

Since HER3 lacks intrinsic kinase activity, TKIs (tyrosine-kinase inhibitors) will be not effective in inhibiting HER3. Antibody combinations are the current strategies to inhibit HER family signaling network (Hu, et al., Cancer Res, 75: 159-170 (2015); Iida, et al., Mol Cancer Ther, 15: 2175-2186 (2016)). However, most antibodies are expensive to produce and have high immunogenicity. To address immunogenicity and high cost of antibody, a nucleic acid-based multiple function molecule with a siRNA and two RNA aptamers was engineered. The new siRNA-aptamer chimera is able to target EGFR/HER2/HER3 simultaneously with low toxicity. Recently, aptamer-siRNA chimera, employing only RNA molecules, is attractive for cell type-specific gene silencing. Aptamers are ssDNA or RNA and selected through in vitro enrichment process (Ellington, et al., Nature, 346: 818-822 (1990)). Like antibodies, aptamers can bind to target with high affinity and specificity. Due to small and oligonucleotide properties, aptamers offer many advantages over antibodies including non-immunogenicity, high tissue penetration, thermostability, low cost, and ease of synthesis and modification (Keefe, et al., Nat Rev Drug Discov, 9:537-550 (2010); Zhou et al., Nat Drug Rev Discov, 16: 181-202 (2017)). Current cell type-specific RNA aptamers have been used for targeting delivery of siRNA and drugs (Wheeler, et al., J Clin Inves, 121: 2401-2412 (2011); Neff, et al., Sci Transl Med.)

HER3 aptamer has been identified and is able to specifically bind to the extracellular domains of HER3 (Chen, et al., Proc Natl Acad Sci USA, 100: 9226-9231 (2003)). HER3 aptamer inhibits HRG-dependent tyrosine phosphorylation of HER2 (Takahashi, et al., Sci Rep, 6: 33697 (2016)). With a similar generation approach, HER2 aptamer has been identified and synthesized. HER2 aptamer shows high specificity to HER2 positive but not negative cancer cell lines (Kim, et al., Nucleic Acid Ther, 21:173-178 (2011)).

Therefore, it is an object of the invention to provide immunotherapies that have reduced off-target effects for the treatment of cancer including but not limited to, ovarian cancer, non-small-cell lung cancer, cervical cancer, prostate cancer, esophageal and stomach cancers, preferably breast cancer, It is also an object of the invention to provide methods of treating cancer using non-antibody therapies.

SUMMARY OF THE INVENTION

An aptamer platform capable of efficiently delivering and silencing two or more genes in vivo or in vitro is provided.

Methods of using the apatmers compositions for selectively targeting cells to down-regulate the expression of multiple genes are also provided.

Currently, most chimeras are designed as the fusion of one aptamer with one siRNA (Dassie, et al., *Nat Biotechnol*, 27: 839-849 (2009); Herrmann, et al., *J Clin Invest*, 124: 2977-2987 (2014); Zhou, et al., *Mol Ther*, 16: 1481-1489 (2008); Hussain, et al., *Nucleic Acid Ther*, 23: 203-212 (2013); Wheeler, et al., *J Clin Invest*, 121: 2401-2412 (2011)). Importantly, simultaneous delivery of multiple siRNAs has not been reported. In one embodiment, the disclosed aptamers delivers at least one siRNAs against one or more different genes to cells expressing a specific cell surface protein or secreting a specific protein into the microenvironment of the cell. The genes to be down-regulated include, but are not limited to oncogenes, proto-oncogenes, tumor specific antigens, and viruses.

One embodiment provides an aptamer composition that contains an siRNA that down-regulates expression of EGFR. The aptamer composition also contains two aptamers on either end of the chimera that specifically bind to a cell surface protein, for example a tumor specific antigen or a viral antigen. Using multiple aptamers specific to a cell surface protein increases efficiency of delivering the siRNAs to the targeted cell. The disclosed aptamer compositions are processed by cellular RNA interference machinery (Siomi, et al., *Nature*, 457: 396-404 (2009)) to produce separate and active siRNAs that inhibit expression of three different genes. In one embodiment, the aptamer composition can simultaneously silence EGFR, HER2, and HER3 in vitro and in vivo. The data in the Examples demonstrates a profound efficacy against breast tumor growth through cell cycle arrest and the induction of apoptosis. Delivery of an siRNA by a tumor targeting aptamer-siRNA chimera represents a new approach for combination therapy of using siRNA molecules.

In one embodiment, the aptamer composition specifically binds to HER2 and HER3. Thus, a method for treating HER2 or HER3 expressing breast cancer is provided which includes administering to a subject in need thereof an effective amount of aptamer composition having aptamers that specifically bind to HER2 and HER3 and siRNA constructs that are processed to produce siRNA that inhibits expression of EGFR.

Another embodiment provides a pharmaceutical composition containing one or more aptamer compositions in an amount effective to down-regulate at least two different genes in a target cell.

Another embodiment provides a method for treating a viral infection by administering to a subject in need thereof an effective amount of an aptamer-composition that targets virally infected cells and down regulates two or more genes of the virus infecting the subject.

BRIEF DESCRIPTION OF THE DRAWINGS

FIGS. 5F-5O are a panel of immunofluorescent images showing the results of a biodistribution assay. Athymic female mice were implanted with BT474 cells. After 4 weeks, tumor bearing mice were i.v. injected with Cy5-HEH or Cy5-muHEH. Cy5 fluorescence of whole body was captured at the time points of 0.5 h, 3 h, 12 h, and 24 h using Xenogen IVIS100.

FIGS. 7A-7L are a panel of photomicrographs of formalin-fixed paraffin-embedded sections of xenograft tumors were analyzed with HE staining for detection of morphologic changes and IHC staining for detection of protein levels of EGFR, HER2, and Cleaved Caspase-3. Scale bar, 50 μm.

FIGS. 8A-8N are a panel of photomicrographs showing histological examination of organ damage after HEH treatment with HE staining.

FIG. 11C-11H are line graphs showing dose-dependent cytotoxicity of H2EH3 on different breast cancer cell lines. Data are the mean±SE from three independent experiments.

FIG. 13AA-13BB are Western blots showing total HER family receptors and apoptosis-associated molecules in SKBR3 cells.

FIGS. 17A-17O represents gene expression and apoptosis in xenograft tumors treated with PBS, HER2+siEGFR+HER3, or H2EH3. FIG. 17A-17C show EGFR expression, FIG. 17D-17F show HER2 expression, FIG. 17G-17I show HER3 expression, FIG. 17J-17L show cleaved caspase 3, and FIG. 17M-17O show P21 expression. FIG. 17P-17Y represent gene expression and apoptosis in orthotopic tumors treated with PBS or H2EH3. FIG. 17P-17Q show EGFR expression, FIG. 17R-17S show HER2 expression, FIG. 17T-17U show HER3 expression, FIG. 17V-17W show cleaved caspase 3 expression, and FIG. 17X-17Y show P21 expression.

FIG. 18A-18P are representative histological images of H&E staining of organs from mice with orthotopic tumors treated with PBS or H2EH3. Tissues include: Brain (FIG. 18A-18B), Heart (FIG. 18C-18D), Intestine (FIG. 18E-18F), Kidney (FIG. 18G-18H), Liver (FIG. 18I-18J), Lung (FIG. 18K-18L), Spleen (FIG. 18M-18N), and Muscle (FIG. 18O-18P).

DETAILED DESCRIPTION OF THE INVENTION

I. Definitions

Figure 1A:
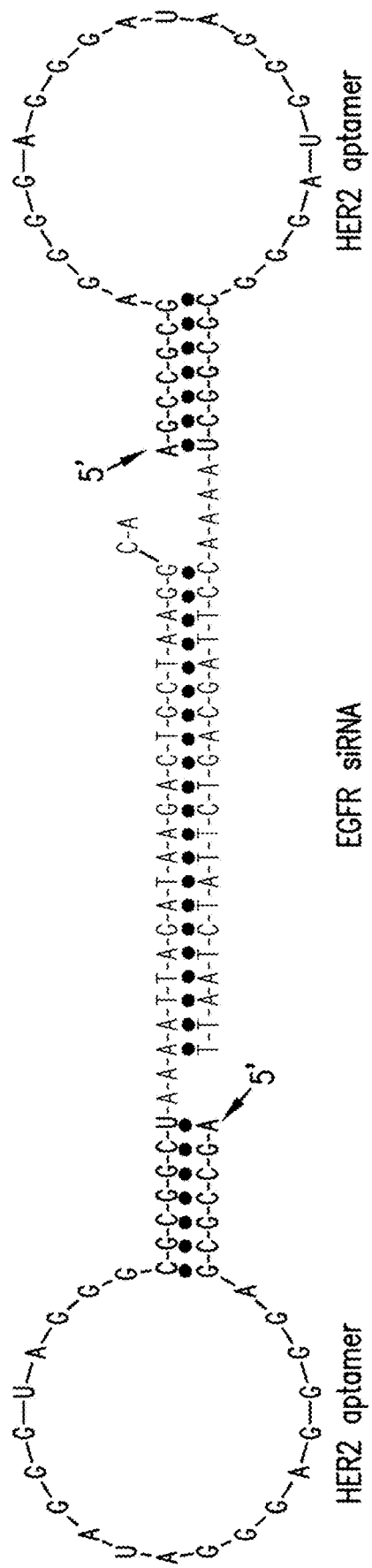
FIG. 1A is a schematic illustration of HER aptamer-EGFR siRNA-HER2 aptamer chimera (HEH).

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "effective amount" in the context of the administration of a therapy to a subject refers to the amount of a therapy that achieves a desired prophylactic or therapeutic effect.

As used herein, the term "in combination" refers to the use of more than one therapy (e.g., one or more prophylactic and/or therapeutic agents). The use of the term "in combination" does not restrict the order in which therapies are administered to a subject with a disease or disorder, or the route of administration. A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disease or disorder or a symptom thereof.

As used herein, the terms "subject" and "patient" are used interchangeably and refer to an animal. In a specific embodiment, such terms refer to a mammal such as a non-primate (e.g., cows, pigs, horses, cats, dogs, rats etc.) and a primate (e.g., monkey and human), most preferably a human. In certain embodiments, such terms refer to a non-human animal (e.g., a non-human animal such as a pig, horse, cow, cat, or dog). In some embodiments, such terms refer to a pet or farm animal. In specific embodiments, such terms refer to a human.

As used herein, the terms "treat", "treating" and "treatment" in the context of the administration of a disclosed aptamer compositions to a subject refer to the beneficial effects that a subject derives from the therapy. In certain embodiments, treatment of a subject with the aptamer composition achieves one, two, three, four, or more of the following effects: (i) reduction or amelioration the severity of disease or symptom associated therewith; (ii) reduction in the duration of a symptom associated with a disease; (iii) prevention of the progression of a disease or symptom associated therewith; (iv) regression of a disease or symptom associated therewith; (v) prevention of the development or onset of a symptom associated with a disease; (vi) prevention of the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy.

The term "oncogene" refers to a gene that can in some circumstances transform a cell into a cancerous cell or a gene that promotes the survival of a cancer cell.

II. Aptamer-siRNA Chimeras

An aptamer platform capable of efficiently delivering and silencing two or more genes in vivo or in vitro is provided. Methods of using the aptamer compositions for treating infections or cancer, for example breast cancer, are also provided.

A. Aptamer Platform Design

Figure 11A:
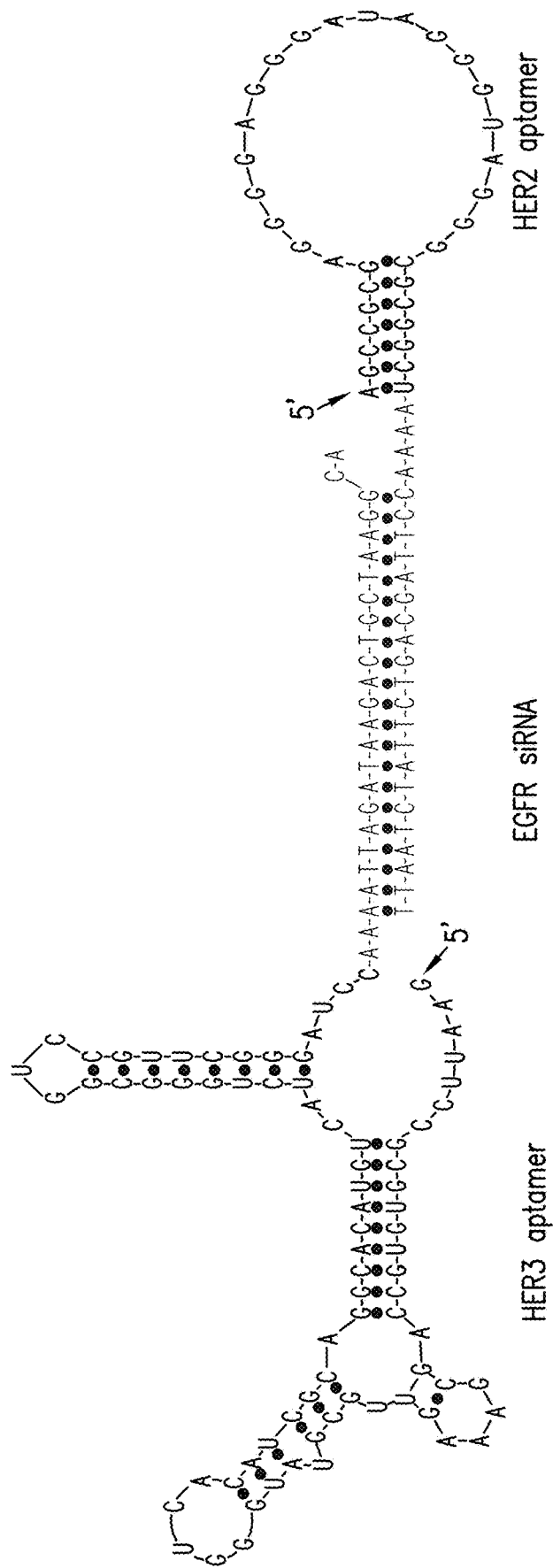
FIG. 11A is a schematic illustration of HER aptamer-EGFR siRNA-HER2 aptamer chimera (H2EH3). The nucleic acid sequence for the HER3 aptamer is SEQ ID NO:36. The nucleic acid sequence for the HER2 aptamer is SEQ ID NO:35. The nucleic acid sequence for the EGFR siRNA affixed to the HER3 aptamer is SEQ ID NO:38 and the siRNA affixed to the HER2 aptamer is SEQ ID NO:37.

In one embodiment, the aptamer composition contains at least one siRNA that inhibits or reduces expression of one or more oncogenes (FIG. 1A). The aptamer-siRNA chimera also contains a different aptamer on each end of the chimera that specifically binds to a tumor cell surface protein are provided. Exemplary tumor cell surface proteins include oncogenes and proto-oncogenes. The structure of chimera can be processed by cellular RNAi machinery to produce the active siRNAs for each targeted oncogene. Having two different aptamers offers enhanced cargo internalization and target specificity (FIG. 11A).

In one embodiment, the aptamer and siRNAs are separated by a linker. The linker can be about 2-10, 3-9, or preferably about 4 nucleotides. An exemplary linker is four Adenine ("A"). The linker helps to warrant the cleavage with dicer but not mixing two genes, since dicer is able to measure and cut 21-25-nt RNA duplex. The size of the exemplary HER2 aptamer-EGFR siRNA-HER3 aptamer is about 55.4 Kd, which is larger than each single aptamer, and larger than renal glomerulus cutoff mass (30-50 Kd), but smaller than antibody (150 Kd). Chimera with two aptamers are expected to have a longer circulation time than single aptamer alone.

In one embodiment, the RNA chimera incorporates 2' F into the entire RNA chimera by T7 RNA polymerase-driven transcription. Previously reported aptamer-siRNA chimeras contain one strand unmodified siRNA (Xiao, et al., Mol Cancer Ther, 15: 689-701 (2016); Dassie, et al., Nat Biotechnol, 27: 839-849 (2009)). 2' F completely modified RNA offers more serum stability than partial modified chimeras. The efficacy in tumor targeting and gene knockdown of EGFR, HER 2, and HER3 was confirmed, and the profound reduction of tumor size and induction of apoptosis have been achieved, suggesting the efficacy of targeting on multiple proliferation pathways.

Dysregulation of cell cycle progression and apoptosis are hallmarks of cancer formation and progression. Cell cycle genes include but are not limited to cyclins and cyclin-dependent kinases (CDK), P53, and Ki67. Apoptotic genes include but are not limited to Fas, Fas ligands, caspases, P21, PARP, and Bcl-2 family members. The data show that H2EH3 enables down-regulation of the expression of HER2, HER3, and EGFR, thereby triggering cell cycle arrest and apoptosis. HER2+HER3+ cells lines treated with H2EH3 showed G2/M arrest and an increase in Annexin V positive cells.

The data show that siRNAs can be delivered to targeted cells by the aptamer compositions. Delivery of siRNA to a cell targeted by two different aptamers in one chimera provides a new and efficient approach for combination therapy. Since the system is highly modular, it can be applied to many targeting co-delivery designs by using siRNA and aptamers. The data also demonstrated that repeated administration is well tolerated and did not elicit an innate immune response.

Small interfering RNA (siRNA) has great potential for sequence-specific silencing of any genes and has emerged as a promising new therapeutic paradigm for "undruggable" targets (Hannon, et al., Nature, 418: 244-251 (2002); Jensen, et al., *Sci Transl Med*, 5: 209ra152. doi: 10.1126/scitranslmed.3006839 (2013); Wu, et al., *Sci Transl Med*, 6: 240ps7, doi:10.1126/scitranslmed.3008362 (2014)). However, the use of siRNA as a therapeutic has been hampered by the difficulty of delivery (Whitehead, et al., *Nat Rev Drug Discov*, 8: 129-138 (2009)). Recently, aptamers (synthetic DNA/RNA ligands) have proven to be a promising platform for delivering siRNA into cells. Selected in a process known as SELEX (systematic evolution of ligands by exponential enrichment) (Ellington, et al., *Nature*, 346: 818-822 (1990); Tuerk, et al., *Science*, 249: 505-510 (1990)), aptamers can specifically bind to various targets including organics, peptides, proteins and cells (Zhou, et al., *Front Genet*, 3: 234, doi:10.3389/fgene.2012.00234 (2012)). Particularly, cell-based SELEX allows the selection of internalized aptamers, which can induce the intracellular delivery of cargo through receptor-mediated endocytosis (Zhou, et al., *J Vis Exp*, 52: e2954, doi: 10.3791/2954 (2011)). Aptamers have specific 3-dimensional structures for target binding with high affinity, which can be maintained in vivo. Aptamer-siRNA chimera (AsiC), employing only RNA molecules, is a new targeting therapeutic (Dassie, et al., *Ther Deliv*, 4: 1527-1546 (2013); Wang, et al., *Theranostics*, 5: 1456-1472 (2015)) and has shown the promise of minimizing off-target effects that are usually associated with small molecule drugs and immunogenicity of antibody-based therapeutic. As a single-component entity, AsiC also has advantages in ease of synthesis and high tissue penetrability. Importantly, AsiC-based drugs can utilize endogenous enzymes (e.g., dicer, argonaute) and enable cell type- and mRNA sequence-specific gene silencing, which can provide selective and effective inhibition of protein targets regardless their cellular localization. For examples, CD4 aptamer-tat/rev siRNA chimera has shown the efficacy in inhibition of HIV transmission (Neff, et al., *Sci Transl Med*, 3: 66ra6 (2011)), PSMA aptamer-PLK1siRNA enables the regression of prostate cancer (Dassie, et al., *Nat Biotechnol*, 27: 839-849 (2009)). CTLA4 aptamer-STAT3 siRNA inhibits tumor-associated Tregs and reduces tumor burden in multiple mouse tumor models (Herrmann, et al., *J Clin Invest*, 124: 2977-2987 (2014)). EpCAM aptamer-survivin siRNA enables reversal of doxorubicin resistance and prolongs survival in mice bearing chemoresistant tumors (Wang, et al., *Theranostics*, 5: 1456-1472 (2015)).

B. Aptamers

In one embodiment, the aptamer composition contains two aptamers. The aptamers can specifically bind the same target, or in some embodiments, the aptamers can specifically bind to different targets. In a preferred embodiment, the aptamers bind to the same target, for example HER 2 or HER3.

Aptamers are molecules that interact with a target molecule, preferably in a specific way. Typically aptamers are small nucleic acids ranging from 15-200 bases in length that fold into defined secondary and tertiary structures, such as stem-loops or G-quartets. Aptamers can bind to protein, cells, small organic, peptide. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

III. Targeted Cell Surface Proteins

In one embodiment, the aptamers in the aptamer compositions can specifically bind to a cell surface protein or a protein or peptide secreted into the microenvironment of cell to be treated, for example a cancer cell, tumor cell, or virally infected cell. In some embodiments, the protein or peptide that is specifically recognized by the aptamers of the aptamer composition can be cell surface proteins involved in signal transduction, tumor specific antigens, tumor neovasculature antigens, viral proteins or viral peptides displayed in the surface of cells, cytokines, and cytokine receptors. These targeted proteins or peptides may be substances produced by a cell or may be substances which accumulate at a cell microenvironment site, or on cell surfaces.

In one embodiment, the aptamers specifically bind to PDGF, nucleolin, P-selectin, EpCAM, CD44, Mucin, AXL, PSMA, ICAM-1, VCAM-1, transferrin receptor, ErbB2, VEGFR, HIV-1 Tat protein, HIV Nuceocapsid, integrin, Her3, IL-10, anti-NF-KB, Kanamycin A, catenin, ERK2, C-reactive protein, L-tryptophan, SARS Coronavirus, influenza B, thrombin Hemagglutinin, tumor necrosis factor-alpha, VEGF, streptavidin, Kit-129, HIV Reverse transcriptase, insulin, PSA, RNase H1, Swine influenza A virus, Human neutrophil elastase, anti-IgE, L-selectin, 4-1BB, Tenascin-C, Protein Kinase C, RBP4, Enterotoxin B, her2, Hepatocyte growth factor receptor, Hepatitis C, Fibrogen, HGF, IgG, EGFR, survivin, Osteopontin, P-selectin, neurotrophin receptor, interferon-γ, Human matrix metalloprotease 9, Keratinocyte growth factor, MCP-1, von-Willebrand factor, Plasminogen activator inhibitor-1, OX40, CD4, CD3, CD8, Tenascin-C, androgen receptor (AR), androgen receptor splicing variants (ARV7 (AR3), ARV12, ARV3, ARV1, ARV9, ARV2, ARV5/6, ARV8, ARV9, ARV10, ARV11).

In one embodiment, the aptamers of the aptamer composition specifically bind to HER2 or HER3.

A. Tumor Specific Antigens

In some embodiments disclosed aptamers may be specific to or selective for a variety of cell surface or disease-associated antigens. In certain embodiments, such as treating tumors, the aptamers of the disclosed compositions specifically bind tumor-associated antigens. These antigenic markers may be substances produced by a tumor or may be substances which accumulate at a tumor site, or on tumor cell surfaces.

In some embodiments, the targeting domains bind to antigens, ligands or receptors that are specific to tumor cells or tumor-associated neovasculature, or are upregulated in tumor cells or tumor-associated neovasculature compared to normal tissue.

1. Oncogenes

Tumor-associated antigens that are targeted by the disclosed compositions may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

Exemplary oncogenes that can be targeted to direct the disclosed compositions to tumors, tumor cells, or tumor microenvironments include, but are not limited to ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, S S18, TCL1A, TET2, TFG, MLL, TLX1, TPR, and USP6.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.*, 309:883 (1983); Lloyd, et al., *Int. J. Canc.*, 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.*, 36:755 (1997); Sarandakou, et al., *Eur. J. Gynaecol. Oncol.*, 19:73 (1998); Meier, et al., *Anticancer Res.*, 17(4B):2945 (1997); Kudoh, et al., *Gynecol. Obstet. Invest.*, 47:52 (1999)). Elevated serum CA125 may also accompany neuroblastoma (e.g., Hirokawa, et al., *Surg. Today*, 28:349 (1998), while elevated CEA and SCC, among others, may accompany colorectal cancer (Gebauer, et al., *Anticancer Res.*, 17(4B):2939 (1997)).

A tumor antigen may include a cell surface molecule. Tumor antigens of known structure and having a known or described function, include the following cell surface receptors: HER1 (GenBank Accession No. U48722), HER2 (GenBank Acc. Nos. X03363 and M17730), HER3 (GenBank Acc. Nos. U29339 and M34309), HER4 (GenBank Acc. Nos. L07868 and T64105), epidermal growth factor receptor (EGFR) (GenBank Acc. Nos. U48722, and KO3193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043), insulin-like growth factor-II (GenBank Acc. Nos. X03562, X00910, M17863 and M17862), transferrin receptor (Trowbridge and Omary, *Proc. Nat. Acad. USA*, 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA*, 86:7159 (1989); GenBank Acc. Nos. M65132 and M64928) NY-ESO-1 (GenBank Acc. Nos. AJ003149 and U87459), NA 17-A, Melan-A/MART-1 GenBank Acc. Nos. U06654 and U06452), tyrosinase (GenBank Acc. No. M26729), Gp-100 (GenBank Acc. No. S73003), MAGE (GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA; GenBank Acc. Nos. M59710, M59255 and M29540), and PyLT (GenBank Acc. Nos. J02289 and J02038); p97 (melanotransferrin), Additional tumor associated antigens include prostate surface antigen (PSA); β-human chorionic gonadotropin (β-HCG); glycosyltransferase acetylgalactosaminyltransferases (GalNAc); NUC18; melanoma antigen gp75 (GenBank Accession No. X51455); human cytokeratin 8; high molecular weight melanoma antigen.

Tumor antigens of interest include antigens regarded in the art as "cancer/testis" (CT) antigens that are immunogenic in subjects having a malignant condition. CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARa fusion protein, PTPRK, K-ras, N-ras, Triosephosphate isomeras, Bage-1, Gage 3,4, 5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the disclosed fusion proteins.

2. Tumor Neovasculature Antigens

The targeted antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $a_5\beta_3$ integrin/vitronectin. Other antigens that are over-expressed by tumor-associated neovasculature as compared to normal vasculature are known to those of skill in the art and are suitable for targeting by the disclosed fusion proteins.

B. Chemokine or Chemokine Receptors

In another embodiment, the aptamer on the composition specifically binds to a chemokine or a chemokine receptor. Chemokines are soluble, small molecular weight (8-14 kDa) proteins that bind to their cognate G-protein coupled receptors (GPCRs) to elicit a cellular response, usually directional migration or chemotaxis. Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are important for tumor progression.

Based on the positioning of the conserved two N-terminal cysteine residues of the chemokines, they are classified into four groups namely CXC, CC, CX3C and C chemokines. The CXC chemokines can be further classified into ELR+ and ELR− chemokines based on the presence or absence of the motif 'glu-leu-arg (ELR motif)' preceding the CXC sequence. The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor. Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

In one embodiment, tumor or tumor-associated neovasculature targeting domains are ligands that bind to cell surface antigens or receptors that are specifically expressed on tumor cells or tumor-associated neovasculature or are overexpressed on tumor cells or tumor-associated neovasculature as compared to normal tissue. Tumors also secrete a large number of ligands into the tumor microenvironment that affect tumor growth and development. Receptors that bind to ligands secreted by tumors, including, but not limited to growth factors, cytokines and chemokines, including the chemokines provided above, are suitable for use in the disclosed fusion proteins. Ligands secreted by tumors can be targeted using soluble fragments of receptors that bind to the secreted ligands. Soluble receptor fragments are fragments polypeptides that may be shed, secreted or otherwise extracted from the producing cells and include the entire extracellular domain, or fragments thereof.

In another embodiment the aptamers of the disclosed compositions specifically bind to target antigens selected from the group consisting of carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, PSMA, CEACAM5, CEACAM6, c-met, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, PLAGL2, and an oncogene product. A particularly preferred target antigen is CEACAM5 (CEA).

C. Viral Antigens

In some embodiments, the protein that is bound by the aptamer is a viral protein selected from the group consisting of a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

D. Genes to be Down-Regulated

The disclosed aptamer composition contains one or more siRNAs that specifically inhibit or down-regulate expression of one or more different genes. In some embodiments, the one or more different genes are oncogenes. In a preferred embodiment, at least one siRNA inhibits or reduces the expression of EGFR.

1. Oncogenes

Exemplary oncogenes or proto-oncogenes that can be inhibited by the siRNA include, but are not limited to the oncogenes and proto-oncogenes discussed above is Section II.A.1. Representative oncogenes that can be down-regulated by the siRNA in the chimeras include, for example ABL1, ABL2, AKT1, AKT2, ATF1, BCL11A, BCL2, BCL3, BCL6, BCR, BRAF, BIRC5, CARD11, CBLB, CBLC, CCND1, CCND2, CCND3, CCNE1, CDX2, CTNNB1, DDB2, DDIT3, DDX6, DEK, EGFR, ELK4, ERBB2, ETV4, ETV6, EVI1, EWSR1, FEV, FGFR1, FGFR2, FGFR3, FGFR4, FGFR6, FGFR1OP, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6.

Sequence information for these oncogenes are known in the art, and one of skill in the art could readily make siRNA constructs to specifically inhibit oncogene expression.

2. Virus Expression to be Inhibited.

Genes encoding viruses or virus components can be targeted for siRNA inhibition using the aptamer compositions Exemplary viruses to be targeted for siRNA inhibition include, but are not limited to pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

Sequence information for the genes of these viruses are known in the art, and one of skill in the art could readily make siRNA constructs to specifically inhibit viral gene expression.

IV. siRNA

In one embodiment, the aptamer compositions contain aptamers and siRNA that specifically inhibit expression of two or more genes. The siRNA in the chimera is processed using cellular siRNA machinery to produce siRNA in active form.

Gene expression can be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

V. Methods of Use

The disclosed aptamer compositions can be used to down-regulate specific genes in targeted cells. In some embodiments, the chimeras are used to down-regulated two or more genes in a targeted cell through siRNA inhibition. The aptamers in the chimeras can be designed to target a protein or peptide that is expressed by the cell.

A. Cancer

In one embodiment, the aptamer compositions are administered to a subject having or suspected of having cancer in an amount effective to inhibit expression of two or more genes in the cancer survival pathway. For example, the aptamer composition can have two aptamers that specifically bind to a cancer antigen or a tumor specific antigen.

A preferred tumor specific antigen is HER2. The genes to be down-regulated in the cancer or tumor cell are typically oncogenes or proto-oncogenes, for example EGFR. In another embodiment, EGFR is down-regulated and an oncogene selected from the group consisting of ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, ELK4, ERBB2, ETV4, ETV6, EVI1 EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6 is also down-regulated.

Thus, methods for treating breast cancer are provided. Other cancers that can be treated include, but are not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or ureter); Wilms' tumor; bladder cancers including, but not limited to, transitional cell carcinoma, squamous cell cancer, adenocarcinoma, carcinosarcoma. Cancers that can be prevented, treated or otherwise diminished by the MDNPs include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, and gastric cancer.

B. Tumor Burden

Another embodiment provides a method for reducing the tumor burden of a subject by administering an effective amount of an aptamer composition that specifically binds a tumor specific antigen produced by the tumor and is processed by cellular iRNA machinery to produce two or more siRNAs that inhibit the expression of at least two genes in the tumor to promote apoptosis of tumor cells.

C. Viral Infections

Another embodiment provides a method for treating a viral infection in a subject in need thereof by administering an effective amount of aptamer composition that contain aptamers that specifically bind to proteins on the virus expressed on the surface of virally infected cells and wherein the chimera is internalized by a virally infected celled and processed to produce two or more siRNAs that inhibit viral genes.

Exemplary viruses that can be treated include, but are not limited to pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

D. Co-Therapies

The aptamer compositions can be used in combination or alternation with a second therapeutic.

1. Cancer Co-Therapies

Non-limiting examples of one or more other therapies that can be used in combination with the aptamer compositions include immunomodulatory agents, such as but not limited to, chemotherapeutic agents and non-chemotherapeutic immunomodulatory agents. Non-limiting examples of chemotherapeutic agents include cyclophosphamide, methotrexate, cyclosporin A, leflunomide, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1 (DEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-alpha antibodies, anti-IL-1alpha antibodies, anti-IL-6 antibodies, anti-IL-8 antibodies (e.g., ABX-TL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-alpha receptor or a fragment thereof, the extracellular domain of an IL-1 alpha receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, INF-alpha, INF-beta, interferon (IFN)-alpha, IFN-beta, IFN-gamma, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-alpha antibodies, and anti-IFN-gamma antibodies), and antibodies that immunospecifically bind to tumor-associated antigens (e.g., Herceptin®). In certain embodiments, an immunomodulatory agent is an immunomodulatory agent other than a chemotherapeutic agent. In other embodiments an immunomodulatory agent is an immunomodulatory agent other than a cytokine or hemapoietic such as IL-1, IL-2, IL-4, IL-12, IL-15, TNF, IFN-alpha, IFN-beta, IFN-gamma, M-CSF, G-CSF, IL-3 or erythropoietin. In yet other embodiments, an immunomodulatory agent is an agent other than a chemotherapeutic agent and a cytokine or hemapoietic factor.

Non-limiting examples of anti-cancer agents that can be used as therapies in combination with the aptamer compositions, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimus tine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine;

bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In specific embodiments, the anti-cancer agent is not a chemotherapeutic agent.

2. Antiviral Co-Therapies

Antiviral agents that can be used in combination with aptamer compositions include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination with aptamer composition include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oscltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

3. Genetic Disorder Co-Therapies

Genetic disorders including: Down's Syndrome, muscular dystrophy, Huntington's Disease, asthma, heart disease, diabetes, obesity, hypertension, X-linked dominant genetic diseases, and autosomal dominant genetic diseases can be treated using the disclosed aptamer composition. The genes known to be involved in the genetic disease or syndrome can be targeted for down-regulation using the disclosed aptamer platform.

E. Administration and Formulations

The disclosed aptamers can be formulated as pharmaceutical compositions for parenteral administration. The formulations can contain one or more pharmaceutically acceptable excipients.

EXAMPLES

Example 1: Engineering of an Aptamer-siRNA Chimera. Bivalent HER2 Aptamer-EGFR siRNA Aptamer Chimera (HEH)

Materials and Methods

Chemicals and Cell culture. Vendors for specific chemicals are listed below. Cell culture products were purchased from Life Technologies (Carlsbad, Calif.). Antibodies were from Cell Signaling Technology (Danvers, Mass.). Single stranded DNAs were synthesized by Integrated DNA Technologies (IDT, Coralville, Iowa). TranscriptAid T7 High Yield Transcription Kits were purchased from Thermo Fisher Scientific. HER2 and HER3 siRNAs were purchased from Life Technologies Corporation. LysoTracker Green DND-26 and Alexa Fluor 488 Annexin V/Dead Cell Apoptosis kits were from Invitrogen. ELISA kits for detection of IFNα and IL-6 were obtained from RayBiotech (Norcross, Ga.). TUNEL assay kit was purchased from R&D systems (Minneapolis, Minn.). 2'Fluoro-2'-deoxycytidine-5'triphosphate and 2'-Fluoro-2'-deoxyuridine-5'-triphosphate, and Cy5 labeled 2'fluoro-labeled HER2 aptamer were purchased from TriLink Biotechnologies (San Diego, Calif.). Cell lines were purchased from the American Type Culture Collection (ATCC, Manassas, Va.). Human serum (Normal Pool) was obtained from Thermo Fisher Scientific.

Aptamer-siRNA Chimera synthesis. The ssDNA templates and primers were synthesized from IDT. For HEH chimera synthesis, two RNAs (RNA1 and RNA2) were generated separately.

RNA1: HER2 aptamer-EGFR sense siRNA.

RNA1 PCR template: 5'-AGCCGCGAGGGGAGGGAT-AGGGTAGGGCGCGGCTAAAACCTTAGCAGTCT-TATCTAATT-3' (SEQ ID NO:1).

RNA1 5' primer: 5'-TAATACGACTCACTATA-AGCCGCGAGGGGAGGGA-3' (SEQ ID NO:2). The forward primer contains T7 RNA polymerase promoter site (bolded) (P1).

RNA1 3'primer: 5'-AATTAGATAA-GACTGCTAAGGTTTTA-3'. (SEQ ID NO:3) (P2)

RNA2: HER2 aptamer-EGFR antisense siRNA.

RNA2 PCR template: 5'-AGCCGCGAGGGGAGGGAT-AGGGTAGGGCGCGGCTAAAATTAGATAA-GACTGCTA-AGGCA-3' (SEQ ID NO:4).

RNA2 5'-primer: P1 (SEQ ID NO:2)

RNA2 3'-primer: 5'-TGCCTTAGCAGTCTTATC-TAAT-TTTAGCCGCGCCCT-3' (SEQ ID NO:5) (P3).

RNA1 and RNA2 were generated by in vitro transcription with PCR products as templates. The PCR products were put into T-A cloning pCR2.1 vector (Invitrogen) and sequenced. Transcription was performed with Transcript Aid T7 High Yield Transcription Kits. 2' F-modified pyrimidines were incorporated into RNAs to replace CTP and UTP. The transcribed RNAs were purified with phenol/chloroform/ isoamyl alcohol (25:24:1) (Sigma-Aldrich), precipitated with isopropanol (Sigma-Aldrich) followed by cold 70% ethanol wash. The RNA pellets were dissolved in nuclease free water (IDT). The purification procedures were used for all transcribed RNAs. RNA1 and RNA2 were mixed at a molar ratio of 1:1 and annealed to form one entity by heating at 94° C. for 3 min, followed by slowly cooling to room temperature.

For HER2 aptamer (RNA3) synthesis, RNA1 PCR template and RNA1 5'-primer will be used as the above sequences, and RNA3 3'-primer is 5'-AGCCGCGCCC-TACCCTATCCCT-3' (SEQ ID NO:6) (P4).

For mutant HEH3 synthesis, RNA4 and RNA5 will be separately synthesized and annealed together.

RNA4: mutant HER2 aptamer-EGFR sense siRNA.

RNA4 PCR template: 5'-AGCCAAACGAGGGGGGAG-AGGGTGGGGGCGCCTGAAAACCTTAGC-AGTCT-TATCTAATT-3' (SEQ ID NO:7).

RNA4 5' primer: 5'-TAATACGACTCACTATAA-GC-CAAACGAGGGGGGAGAGGGT-3' (SEQ ID NO:8) (P5).

RNA4 3' primer: 5'-AATTAGATAA-GACTGCTAAGGTTTTCA-3' (SEQ ID NO:9) (P6).

RNA 5: mutant HER2 aptamer-EGFR antisense siRNA.

RNA5 PCR template: 5'-AGCCAAACGAGGGGGGAG-AGGGTGGGGGCGCCTGAAAATTAGATAA-GACTGCTAAGGCA-3' (SEQ ID NO:10).

RNA5 5'-primer: P5 (SEQ ID NO:8).

RNA5 3'-primer: 5'-TGCCTTAGCAGTCTTATCTAAT-TTTCA-3' (SEQ ID NO:11) (P7).

For HER2 aptamer-scrambled siRNA synthesis, RNA6 and RNA7 will be separately synthesized and annealed together.

RNA 6: HER2-scrambled sense siRNA.

RNA 6 PCR template: 5'-AGCCAAACGAGGGGG-GAGAGGGTGG-GGGCGCCTGAAAAAACAGTC-GCGTTTGCGACTGG-3' (SEQ ID NO:12).

RNA 6 5' primer: P5 (SEQ ID NO:8)

RNA6 3' primer: 5'-CCAGTCGCAAACGCGACTGTTTTTTCA-3'. (SEQ ID NO:13)

RNA 7: HER2-scrambled antisense siRNA.

RNA 7 PCR template: 5'-AGCCAAACGAGGGGG-GAG-AGGGTGGGGGCGCCT-GAAAACCAGTCGCAAACGCGACTGTT-3'. (SEQ ID NO:14)

RNA7 5'-primer: P5 (SEQ ID NO:8).

RNA7 3'primer: AACAGTCGCGTTTGCGACTGGTTTTCA-3' (SEQ ID NO:15).

Western Blot Analysis. Whole-cell protein was extracted with RIPA lysis buffer containing 1× Halt Protease Inhibitor Cocktails and quantitated with Bio-Rad Protein Assay. Protein (100 μg per sample) was resolved on 10% SDS-PAGE and transferred to PVDF membrane. After blocking for 2 h at room temperature in 5% milk in TBS/0.1% Tween™-20, membrane were incubated overnight at 4° C. with the indicated primary antibodies (HER2, EGFR, Cleaved Caspase-3, GAPDH, 1:1000 dilution, Cell signaling), followed by incubation with horseradish peroxidase-conjugated secondary antibodies for 2 h at room temperature. After ECL Western Blotting Substrate (Pierce) was added onto membrane, the signals were captured by the exposure to X-ray film.

Cytotoxicity Assay. Cellular cytotoxicity was quantified by measuring WST-8 formazan using Cell Counting. Cells in RPMI 1640 containing 5% fetal bovine serum were seeded into 96-well plate at a density 5×103 per well for 24 h at 37° C., and then cells were treated with HEH (1 μM), HER2 aptamer (2 μM), EGFR siRNA (1 μM), HScH (1 μM), and muHEH (1 μM) for 72 h at quadruplicate wells without transfection reagents (e.g., Lipofectamine). CCK-8 solution (10 μM) (Dojindo, Japan) was added to each well and incubated at 37° C. for 4 h. Absorbance at 450 nm was measured using a plate reader.

HEH Stability in Cell Culture Medium. 2' F-modified HEH (0.2 nmoles) were put into 40 μL of RPMI 1640 containing 5% fetal bovine serum, which was the condition for chimera treatment, for different time periods. RNA integrity was detected with 3% agarose gel electrophoresis. HEH intensity was measured with ImageJ.

qRT-PCR Assay. Total RNA from BT474 and MDA-MB-231 cells was extracted with RNAeasy plus kits (Qiagen). The quantity of RNAs was determined by NanoDrop. cDNA was generated with iScript cDNA synthesis kits (Bio-Rad). qRT-PCR analyses were performed using SYBR Green Master Mix™ (Bio-Rad) and further carried out on a CFX96™ Real-Time System (Bio-Rad).

```
EGFR primers:
forward
                                         (SEQ ID NO: 16)
5'-CCATGCCTTTGAGAACCTAGAA-3',
and reverse
                                         (SEQ ID NO: 17)
5'-GAGCGTAATCCCAAGGATGTTA-3'.
```

```
GAPDH primers:
forward
                                         (SEQ ID NO: 18)
5'-GGTGTGAACCATGAGAAGTATGA-3',
and reverse
                                         (SEQ ID NO: 19)
5'-GAGTCCTTCCACGATACCAAAG-3'.
```

Detection of Apoptosis by Flow Cytometry. SKBR3 and BT474 cells were treated with HEH (1 μM) or HER2 aptamer (2 μM) or muHEH for 48 h and 72 h. The cells were harvested and washed in cold PBS. Cells were stained with Alexa Fluor 488 annexin V-PI solution for 1 h at room temperature. Cells were acquired by BD FACSCalibur and analyzed using BD FACStation software.

Cellular Uptake Assay with Laser Scanning Confocal Microscopy. Cells were seeded into 35 mm glass-bottom Petri dishes for 24 h in RPMI 1640 supplemented with 5% fetal bovine serum. Cy5-labeled HEH (1 μM), HER2 aptamer (2 μM), or EGFR siRNA (1 μM) was added into culture for 12 h at 37° C. At the same time, LysoTracker Green DND-26 (80 nM) and DAPI (10 μg/mL) were added to the culture medium for imaging. Images were captured using confocal laser scanning microscope (Zeiss 780 inverted). The internalization of treatments was captured by "Z" stacking using an oil-immersion lens (63× magnification). Data were analyzed with 249 Zeiss LSM image Browser.

Cell-type Binding Specificity. Cells including BT474, SKBR3, MDA-MB-231, MCF7, and Hs578T were grown and harvested. After washing, cells were incubated with Cy5-labeled HEH (2 μM) or Cy3-labeled muHEH (2 μM) in the presence of yeast tRNA (300 μg/mL) and sperm DNA (500 μg/mL) for 1 h at 37° C. Cell binding was detected using BD FACSCalibur flow cytometry.

Biodistribution Assay. Athymic nude female mice were implanted with 2×10⁶ BT474 cells. After 4 weeks of implantation, tumor-bearing mice (n=3 per group) were intravenously administered Cy5-labeled HEH (20 nmoles, 200 mL) or an equal mole amount of Cy5-labeled muHEH. The whole-body images were obtained at 0.5 h, 3 h, 12 h, and 24 h using the Xenogen IVIS100 imaging system by setting the wavelength at an excitation of 640 nm and emission at 710 nm.

Mouse Xenograft Models and Drug Administration. Athymic nude female mice (4-6-week old) were obtained from Envigo. BT474 cells (2×106) were injected into the flank of the mouse. Once tumor reached 100 mm3, mice were randomly divided into three groups (n=4). Mice were i.p. injected with PBS (200 μL), HEH (10 nmoles, 200 μL), HER2 aptamer (20 nmoles, 200 μL) three times per week for 4 weeks. Tumor sizes were measured weekly and calculated with the formula V=(L×W2)/2 (W, width; L, length; V, volume). The animals were euthanized 2 days after the last treatment. The tumors and organs were removed.

Histology Assay. Tumor tissue samples and major organs were collected from xenografts and fixed in 10% neutral-buffered formalin and paraffin-embedded. Sections (6 μm) were cut and mounted on the slides and then deparaffinized in xylene and ethyl alcohol. Each block has a section for HE staining. For immunohistochemistry assay, antigen retrieval was performed in 10 mmol/L citrate buffer (pH6) at 95° C. for 30 min, and then sections were incubated in 3% normal goat serum for 2 h and incubated with primary antibodies: caspase-3 (1:200), HER2 (1:800), and EGFR (1:50). After washing, the sections were incubated with biotinylated secondary antibody (1:200) (Vector Laboratories, Burlingame, Calif.) for 1 h. Following washing, the sections were incubated with VECTASTAIN ABC reagents for 30 min. The images were captured with a Nuance fluorescence microscope with a bright field imaging system.

Statistical Analysis. GraphPad Prism™ software was used to perform all statistical analyses. The results were expressed as a mean±SE. All data were analyzed using two-tailed Student's t test by comparing with the control group, and P<0.05 was considered statistically significant.

Figure 1B:
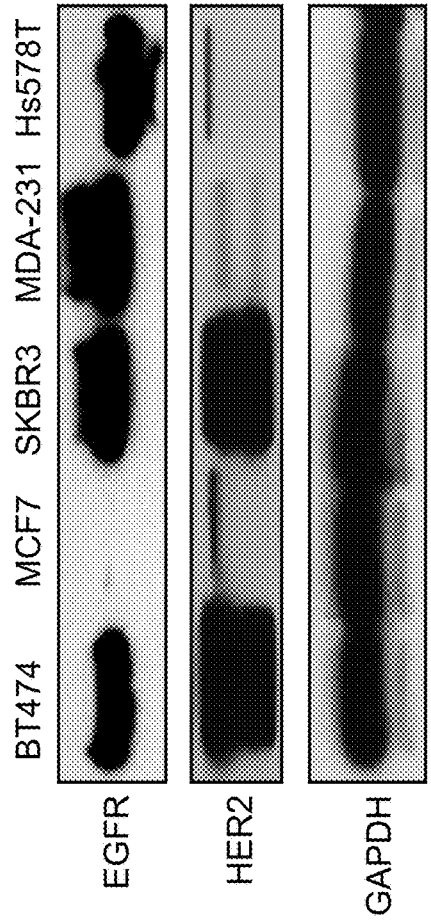
FIG. 1B is an autoradiograph showing detection of HER2 and EGFR expression in breast cancer cell lines by Western blot.
Figure 1C:
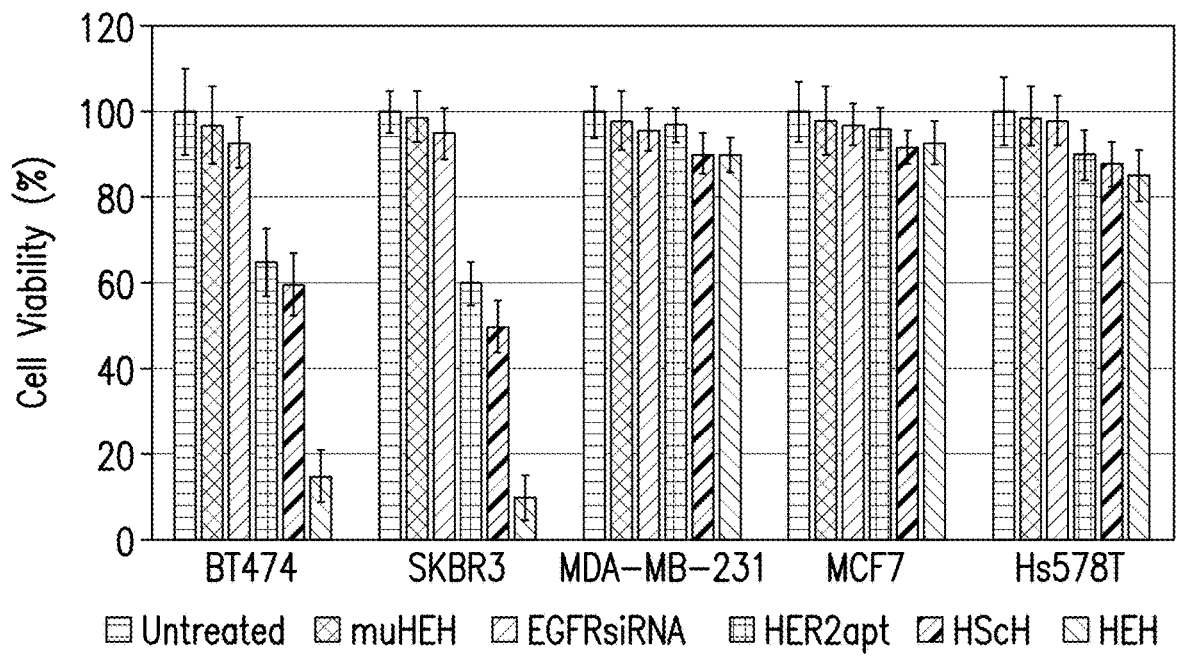
FIG. 1C is a bar graph showing the evaluation of the cytotoxicity of HEH.
Figure 1D:
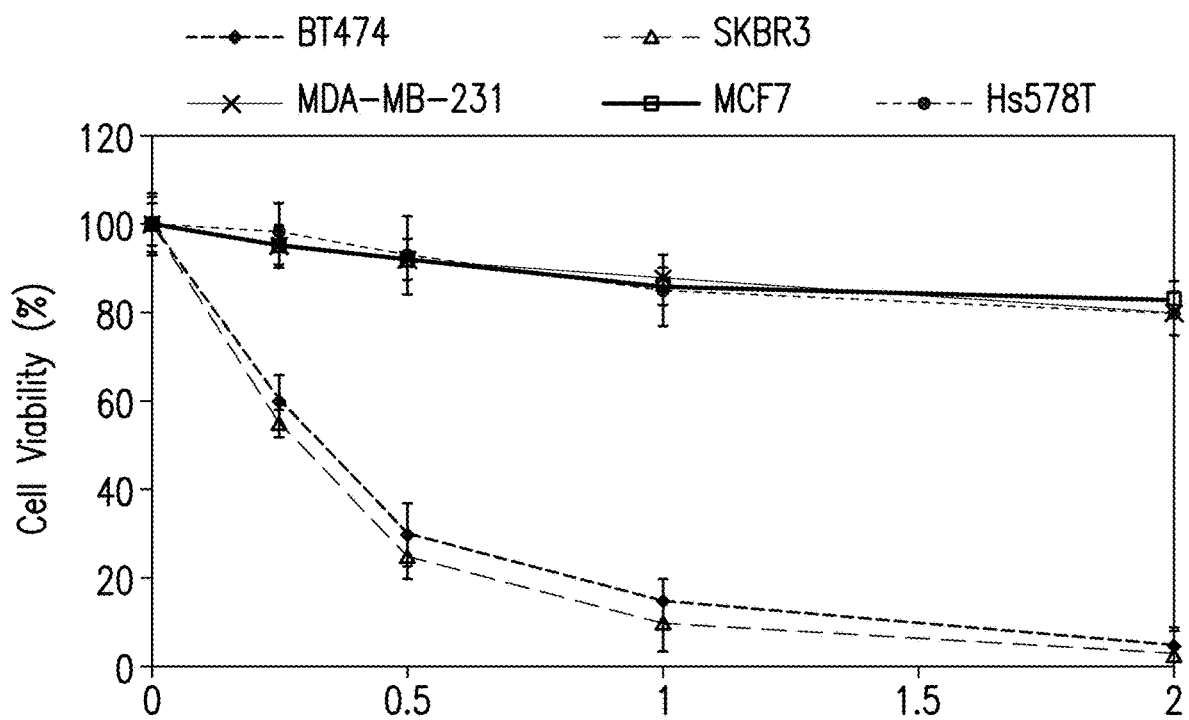
FIG. 1D is a line graph showing dose-dependent cytotoxicity assay of HEH on different breast cancer cell lines. Data are the mean±SE from three independent experiments.
Figure 1E:
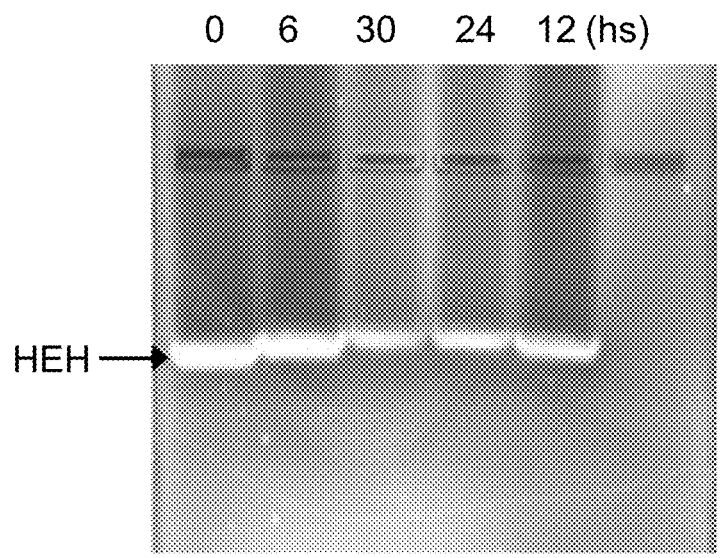
FIG. 1E is a gel and FIG. 1F is a line graph showing HEH stability in cell culture medium.
Figure 1F:
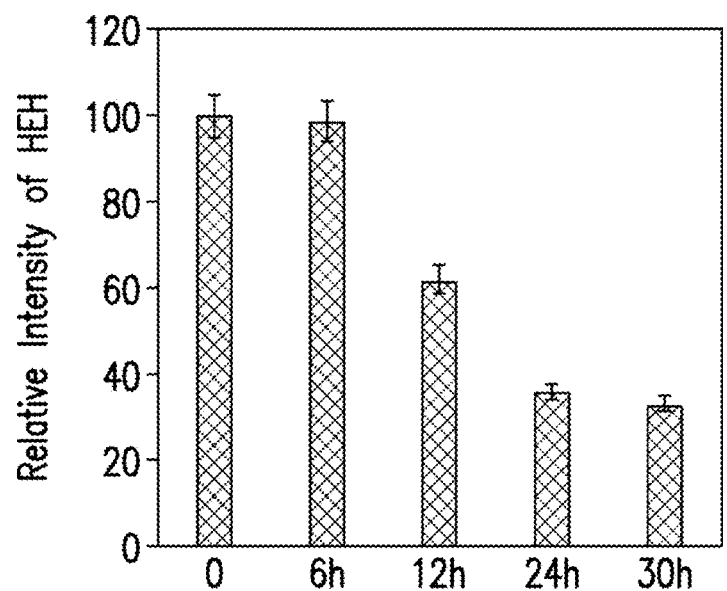

Example 2: Synthesis of Bivalent HER2 Aptamer-EGFR siRNA 298 Chimera and Comparison of Cytotoxicity Bivalent aptamer chimera was constructed with previously established methods. A HER2 aptamer with 34 nucleic acids was selected and was used in this investigation. This aptamer can specifically bind to HER2 expressing tumors in previous studies. Briefly, HER2 aptamer containing EGFR sense strand was fused with HER2 aptamer containing EGFR antisense strand to construct a HER2 aptamer-EGFR siRNA-HER2 aptamer chimera (HEH) as in FIG. 1A. Between aptamer and siRNA, 2-4 unpaired "A"s were added to maintain the flexibility of HER2 aptamer. 2'-Fluoro modified pyrimidines have been incorporated into RNA during transcription to enhance the resistance to nuclease degradation. As shown in FIGS. 1E-1F, in cell culture medium, HEH has no detectable degradation after 6 h incubation, keeps over 60% integrity after 12 h, and still has over 30% integrity after 30 h incubation.

Next, the cytotoxicity of HEH was measured comparing with HER2 aptamer only. Prior to cytotoxicity detection, HER2 and EGFR expression among different breast cancer cell lines was evaluated. As shown in FIG. 1B, SKBR3 and BT474 show the high expression of HER2 and EGFR, and cell lines including MDA-MB-231 and Hs578T are HER2 low expression but with high EGFR expression. MCF7 cells are HER2 low and EGFR negative.

Furthermore, cytotoxicity was measured after treated with HEH (1.0 μM), HER2 aptamer (2.0 μM), mutant HEH (muHEH) (1.0 μM), HER2 aptamer-scrambled siRNA-HER2 aptamer (HScH) (1.0 μM), and EGFR siRNA (1.0 μM) in the above five cell lines. Because one HEH has two copies of HER2 aptamer and one copy of EGFR siRNA, aptamer and siRNA was adjusted with the same amounts (i.e., moles) as HEH. After 72-h treatment, Cell Counting Kit-8 (CCK-8) reagents have been added into the cells. As shown in FIG. 1C, HEH shows the significant cytotoxicity to HER2 expressing SKBR3 and BT474 cells, but not to HER2 negative MCF7, MDA-MB-231, and Hs578T, although both of MDA-MB-231 and Hs578T have high EGFR expression. HER2 aptamer only also shows cytotoxicity to SKBR3 and BT474 cells, but much less efficient than HEH. HER2 aptamer can reduce cell viability by 40% in SKBR3 cells and 35% in BT474 cells. However, HEH can reduce cell viability by 90% in SKBR3 cells and 85% in BT474 cells. Notably, EGFR siRNA and muHEH do not show any cytotoxicity to all detected cell lines. That is not surprising since EGFR siRNA without delivery vehicles cannot freely diffuse into cells and will not play gene silencing functionality outside cells. Because of loss of 3-D conformation of HER2 aptamer in muHEH, muHEH is inactive in binding HER2 receptor and thus lost the capabilities of blocking HER2 receptor and inducing EGFR siRNA internalization. Bivalent HER2 aptamer with scrambles siRNA (HScH) has shown the similar treatment effect as HER2 aptamer only since scrambled siRNA does not target any human genes. These results suggest that HEH have cell type-specific cytotoxicity, and bivalent HER2 aptamer-EGFR siRNA has synergistic effect on HER2 positive breast cancer and outperforms single-targeted HER2 aptamer only.

Example 3: HEH Induced Cell Apoptosis

Figure 2A:
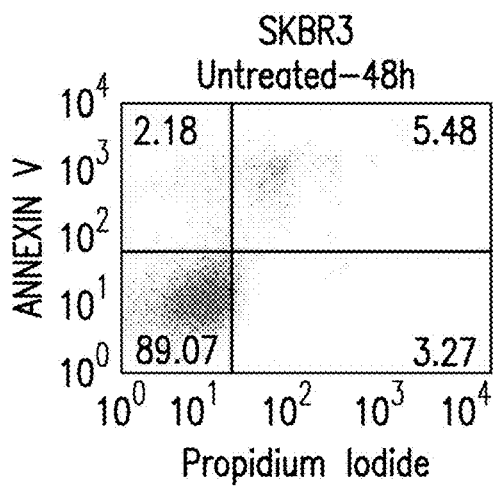
FIGS. 2A-2P are scatter plots showing the detection of cell apoptosis and death by flow cytometry. BT474 and SKBR3 cells were treated with HEH, HScH, and HER2 aptamer for 48 h and 72 h, and then cells were stained with Alexa Fluor 488 Annexin V-Propidium Iodide and analyzed by flow cytometry.
Figure 2B:
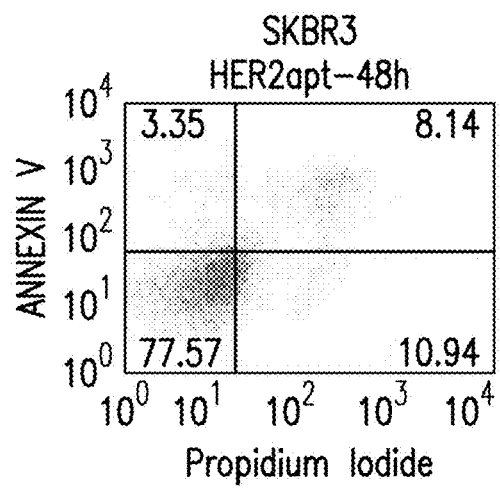
Figure 2C:
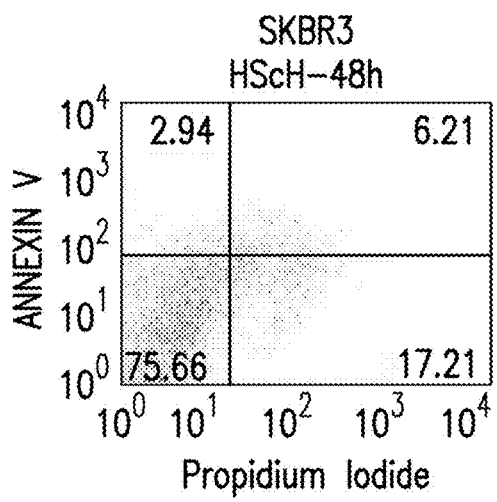
Figure 2D:
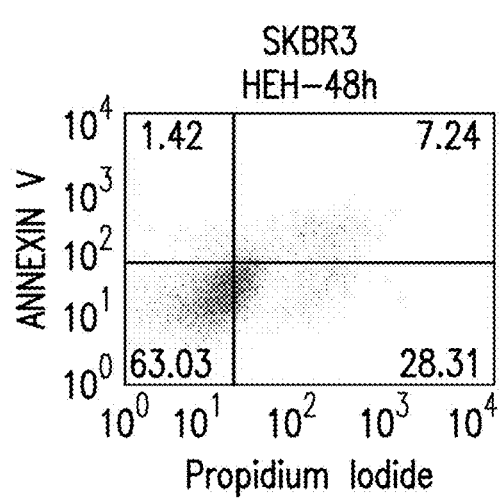
Figure 2E:
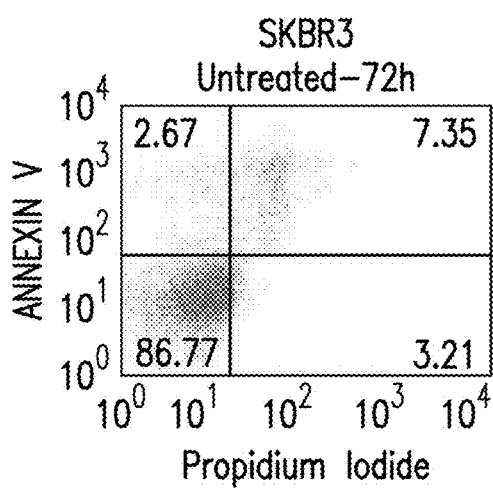
Figure 2F:
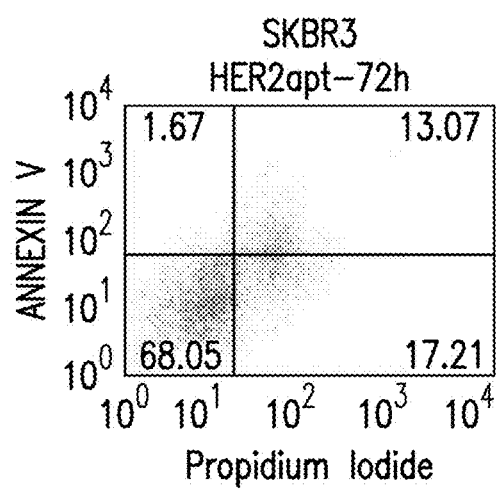
Figure 2G:
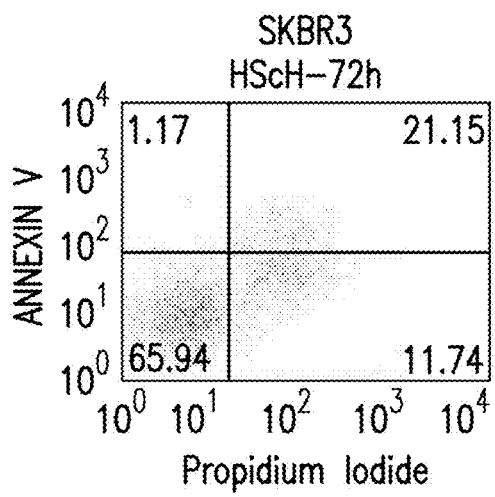
Figure 2H:
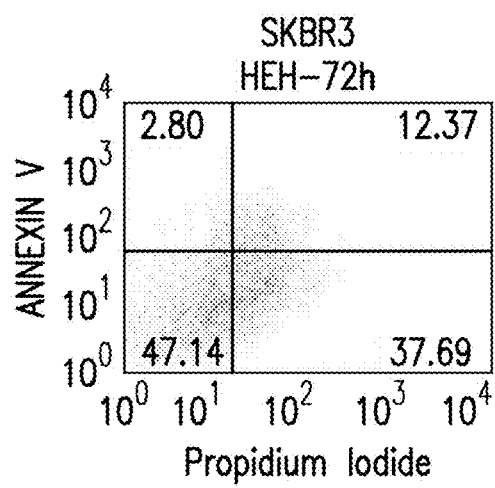
Figure 2I:
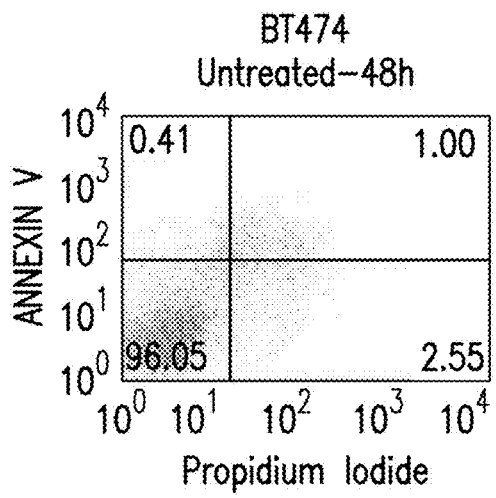
Figure 2J:
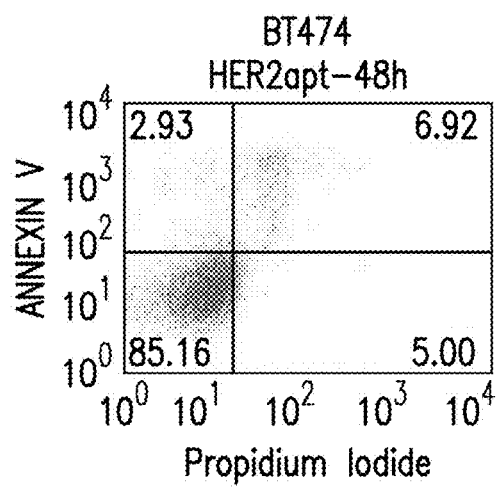
Figure 2K:
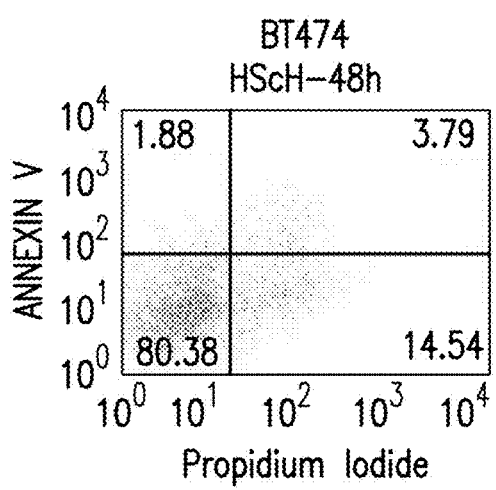
Figure 2L:
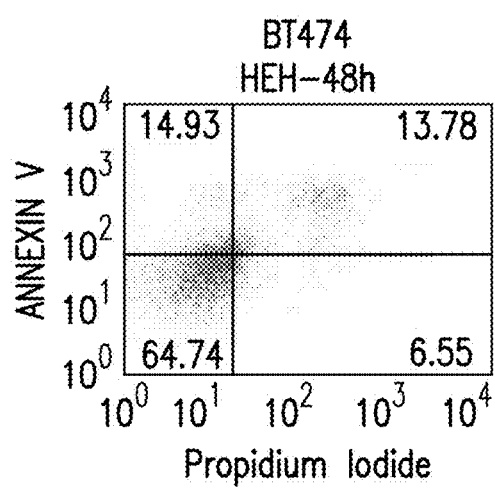
Figure 2M:
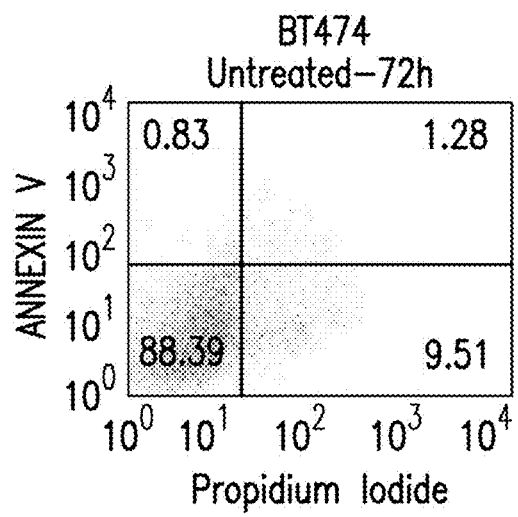
Figure 2N:
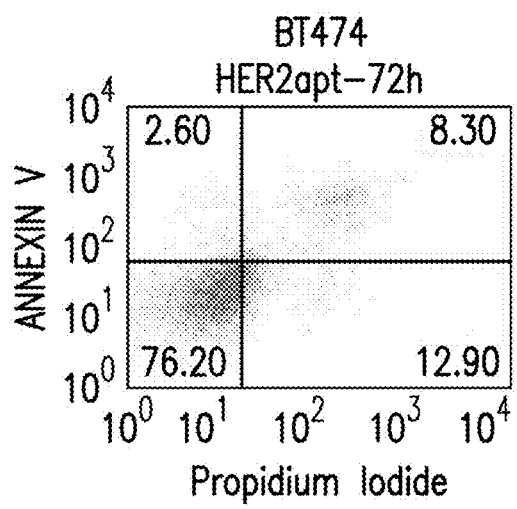
Figure 2O:
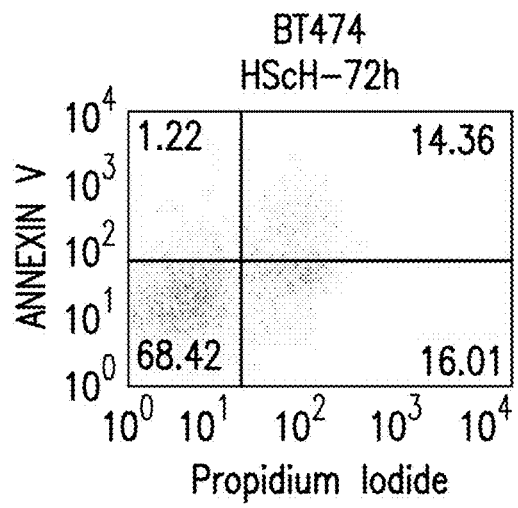
Figure 2P:
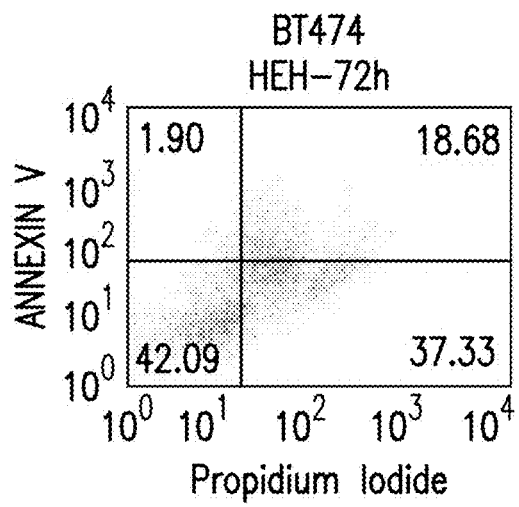

Results:

To test if HEH induced cytotoxicity is through triggering apoptosis, HER2 positive SKBR3 and BT474 cells were treated with HER2 aptamer (2 μM), HScH (1 μM), or HEH (1 μM) for 48 h and 72 h. Cell apoptosis and death were measured with Annexin Vf2 Propidium Iodied (PI) staining. As shown in FIGS. 2A-2P, HER2 aptamer, HScH, and HEH can cause time-dependent cell apoptosis and followed by death in SKBR3 and BT474 cells. In SKBR3 cells, compared with untreated cells, upon treatment with HER2 aptamer alone, the rates of apoptotic and necrotic cells increased by 11.5% after 48 h and 16.04% after 72 h incubation, while upon treatment with HEH, apoptotic and necrotic cells increased by 18.72% after 48 h and 39.63% after 72 h incubation (FIGS. 2A-2H). Similar to SKBR3 cells, in BT474 cells, compared with untreated cells, upon treatment with HER2, apoptotic, and necrotic cells increased by 3.91% after 48 h and 372 24.33% after 72 h, whereas upon treatment with HEH, the rates increase by 12.19% in 48 h and 41.30% in 72 h (FIGS. 2I-2P). HScH showed the similar treatment efficacy as HER2 aptamer only. Overall, HER2 aptamer and HEH can induce cell apoptosis and death; HEH initiates higher levels of cell apoptosis and death than HER2 aptamer only or HScH in both cell lines.

Example 4: HEH can be Internalized into HER2 Expressing Cells and Distribute Cross Cytoplasm Results:

EGFR siRNA between two HER2 aptamers is expected to silence EGFR gene. In previous studies, it was demonstrated that bivalent aptamer, like antibody, can cross-link cell surface receptors and active cells and thus induce significantly increased siRNA internalization compared with monovalent aptamer counter-parts. To validate if bivalent HER2 aptamer has driven EGFR siRNA internalization and enables endosomal escape, which is the prerequisite of siRNA silencing, confocal microscopy was performed to evaluate internalization of Cy5-labeled constructs. BT474 cells were treated with Cy5 labeled HEH, HER2 aptamer, muHEH, and EGFR siRNA. Nuclei were stained with DAPI and endosome/lysosomes were revealed by Lysotracker. After 12-h incubation, confocal laser scanning microscopy with Z-stack was performed to evaluate subcellular distribution of treatments. From Z-stack imaging shown in FIGS. 3A-3E, EGFR siRNA treated cells showed marginal amount of Cy5-EGFR siRNA into cells, whereas HEH treated cells showed significantly increased Cy5-HEH that distributes across entire cells. HER2 aptamer only also shows increased Cy5 signals compared with EGFR siRNA. Quantitatively, about 60% HEH has escaped from endosome entrapment, while about 40% HEH is still entrapped in endosomes. Compared with bivalent HEH, HER2 aptamer shows less overall Cy5 signals than HEH but with similar percentage of endosomal escape as HEH. The results suggest that bivalent HEH indeed can induce cargo internalization and enables endosome escape. The z-stack imaging shows very low amount Cy5 signals in EGFR siRNA treated cells because naked EGFR siRNA cannot diffuse freely through cell membrane.

Figure 3A:
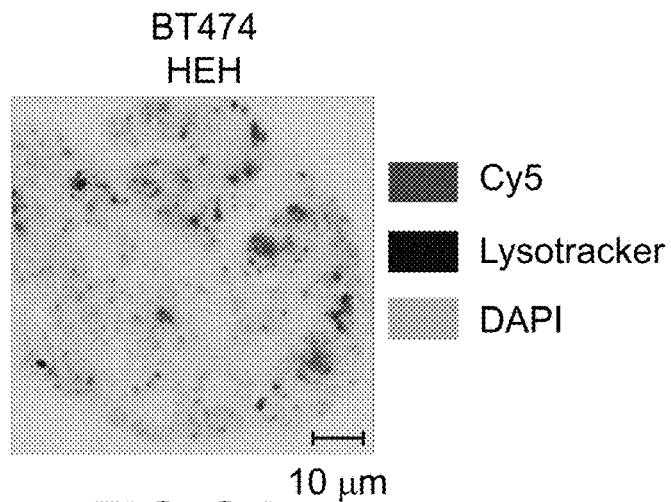
FIGS. 3A-3E is a panel of immunofluorescent micrographs Detection of HEH internalization by Z-stack confocal microscopy. Cy5-labeled HEH, muHEH, HER2 aptamer, or EGFR siRNA was added into BT474 cells for 12 h at 37° C. Lysotracker Green and DAPI were added into cells at the same time as the chimeras. LysoTracker Green was used to show lysosomes and endosomes. DAPI was used to display nucleus. Confocal laser scanning microscopy with z-stack was performed to show cell binding and internalization.
Figure 3B:
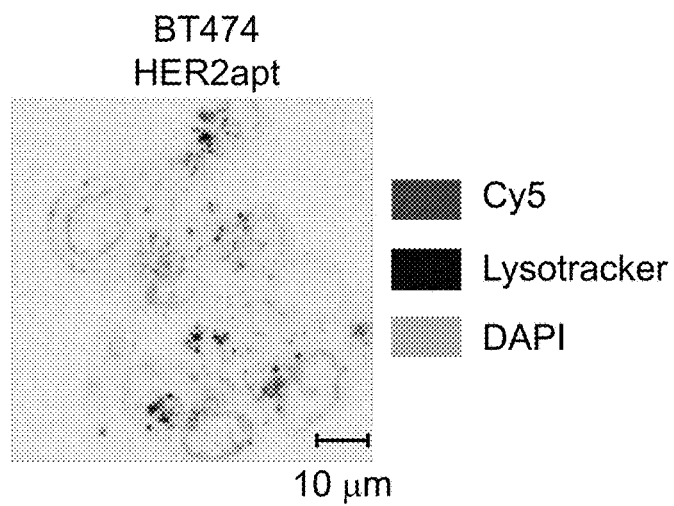
Figure 3C:
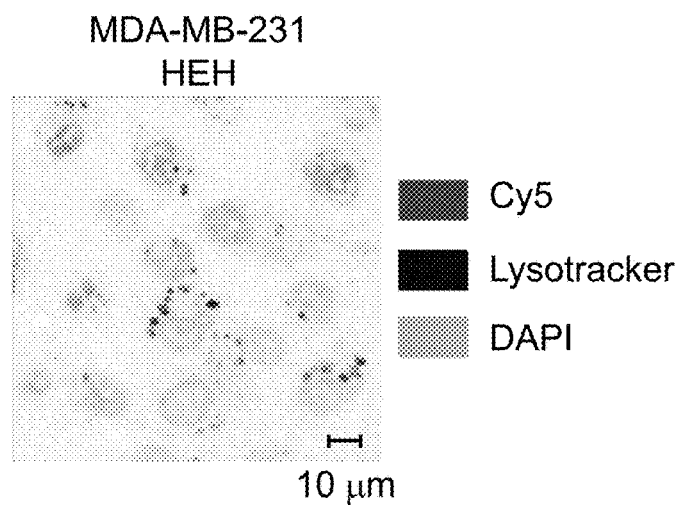
Figure 3D:
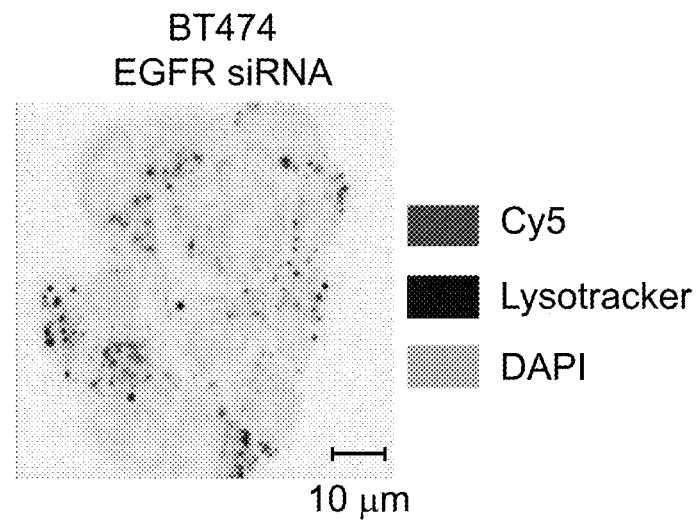
Figure 3E:
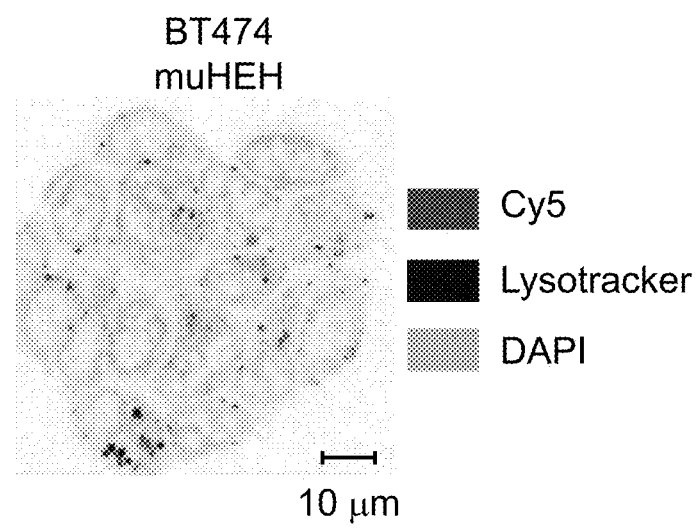
Figure 4A:
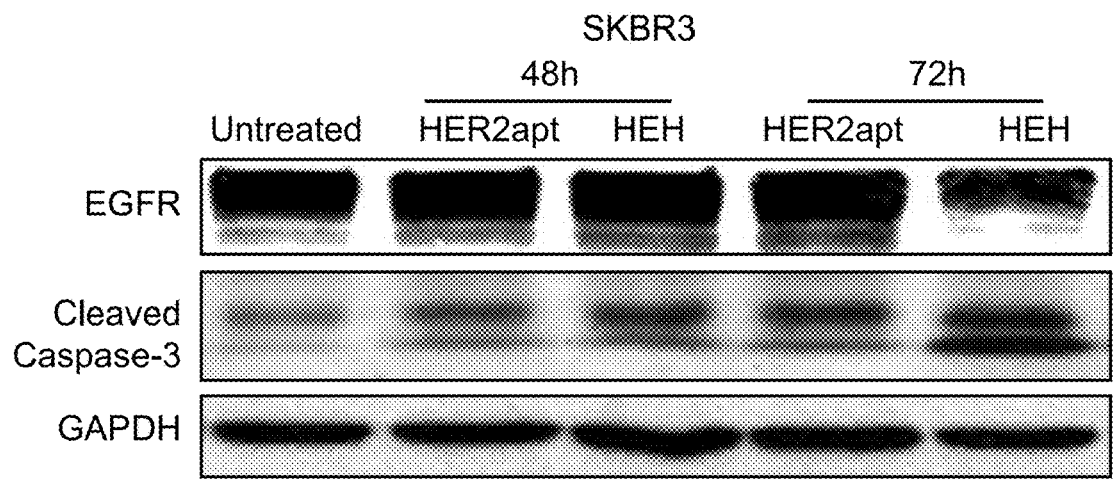
FIGS. 4A-4B show an autoradiograph and a bar graph showing EGFR, cleaved Caspase-3 and GAPDH protein levels in SKBR3 cells treated with HER2 aptamer and HEH, probed in 48 h and 72 h.
Figure 4B:
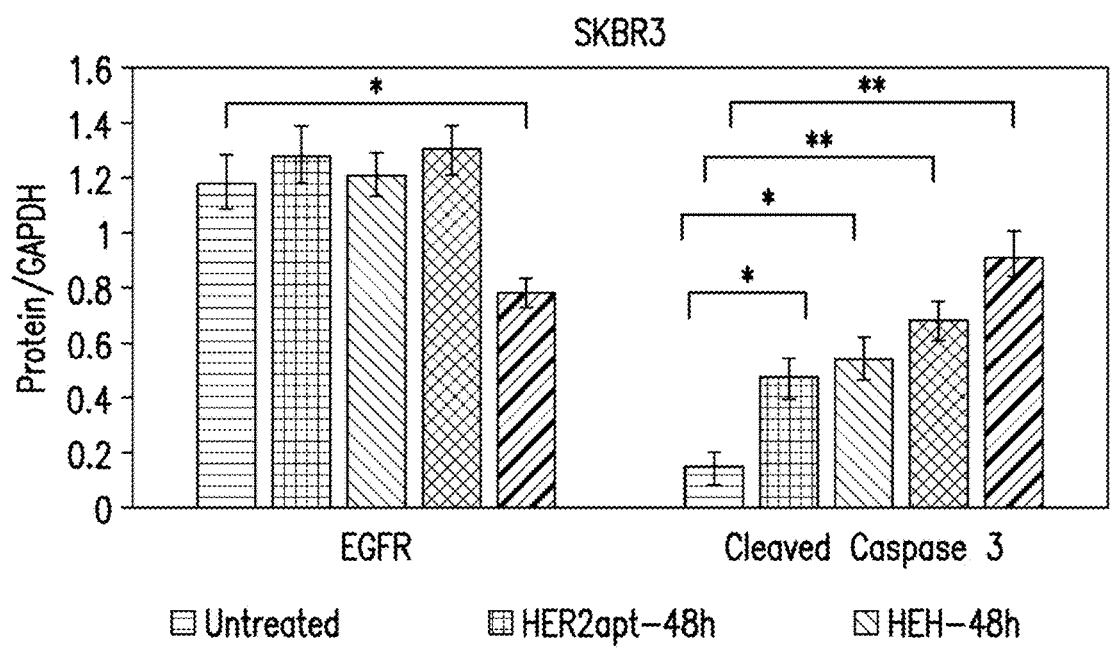
Figure 4C:
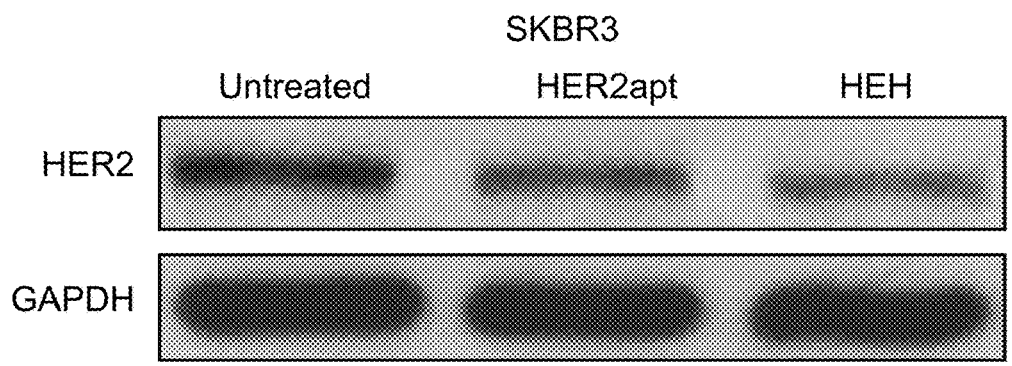
FIGS. 4C-4D are an autoradiograph and a bar graph, respectively, showing EGFR, cleaved Caspase-3 and GAPDH protein levels in SKBR3 cells treated with HER2 aptamer and HEH, probed in 72 h.
Figure 4D:
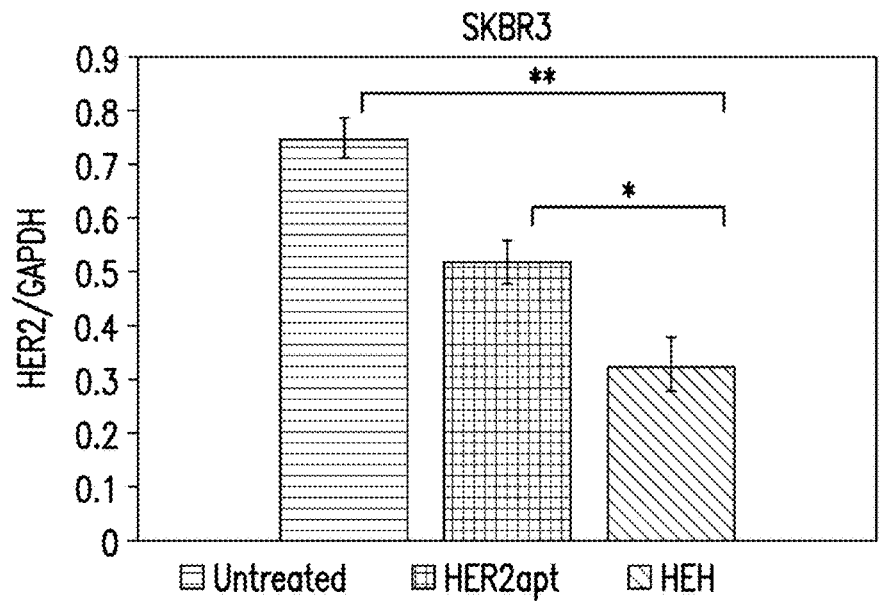
Figure 4E:
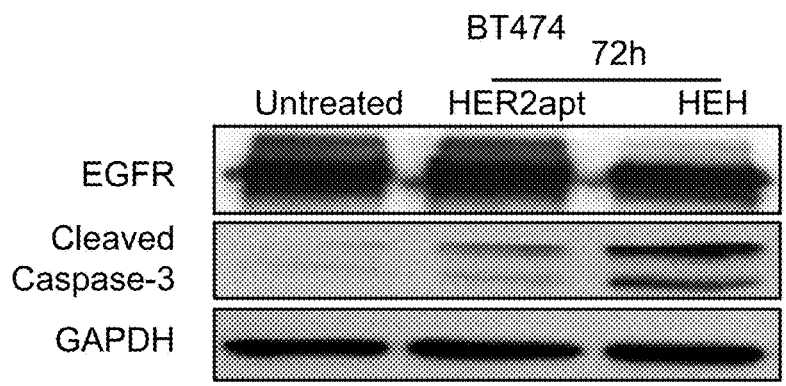
FIGS. 4E-4F are an autoradiograph and a bar graph, respectively, showing EGFR, cleaved Caspase-3 and GAPDH protein levels in BT474 cells treated with HER2 aptamer and HEH, probed in 48 h and 72 h.
Figure 4F:
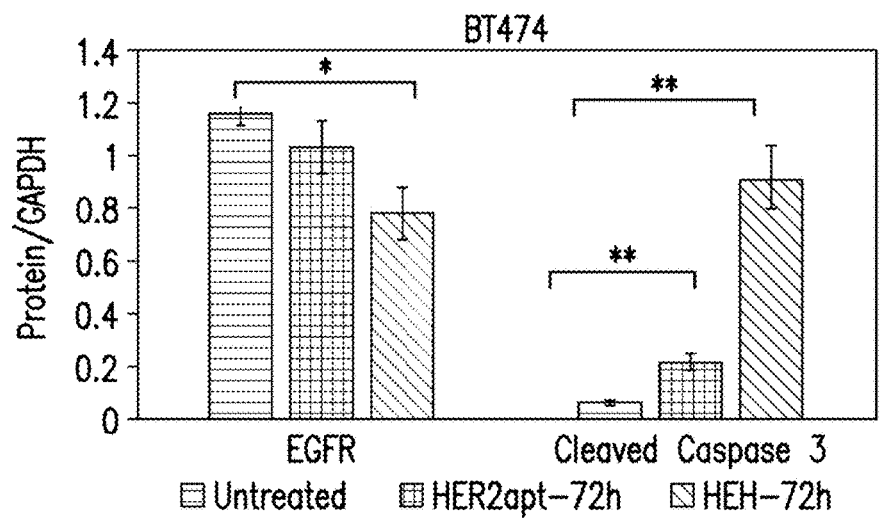
Figure 4G:
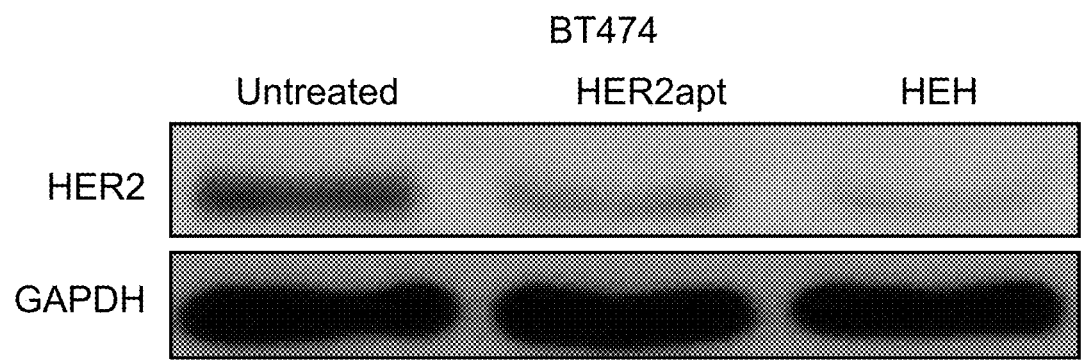
FIGS. 4G-4H are an autoradiograph and a bar graph, respectively, of BT474 cells probed with HER2 was probed. Quantification of protein levels normalized by GPDH using ImageJ. The results are the mean±SEM from three independent experiments. *P<0.05, **P<0.01.
Figure 4H:
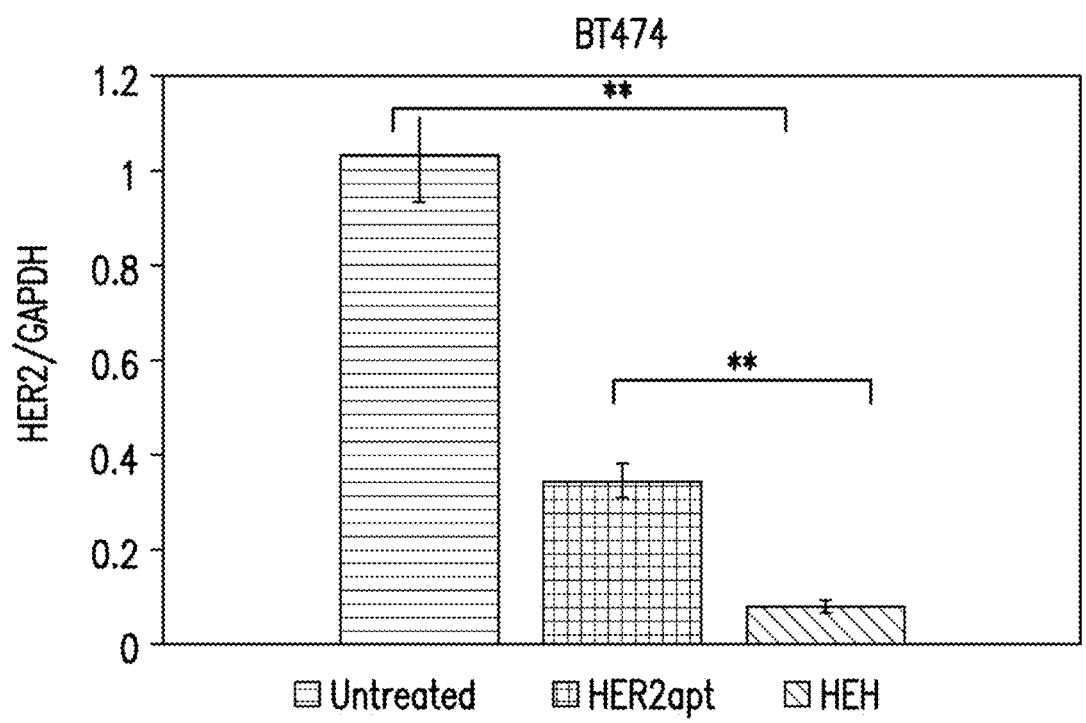

In HEH and HER2 aptamer treated cells, Cy5 signals show puncta pattern, which is the feature of internalization through endocytosis. However, Cy5 signals from EGFR siRNA almost evenly distribute in cytoplasm, which means siRNA only has different uptake mechanisms from HER2 receptor mediated endocytosis. SiRNA only uptake has much lower efficiency than endocytosis. muHEH showed similar Cy5 pattern as EGFR siRNA only, which indicates mHEH cannot enter to cells through endocytosis. This study also emphasizes that an effective carrier is indeed needed to aid siRNA cellular uptake and suggests that bivalent aptamer is a potent carrier for cell-type specific siRNA delivery. As a cell control, HER2 negative MDA-MD-231 cells were treated with Cy5-HEH; as shown in FIG. 3C, there is very low amount of Cy5-HEH in cytoplasm, which suggests that HEH has a high cell-type specific uptake.

HEH is capable of reducing expression levels of EGFR and HER2. Furthermore, the ability of HEH to induce EGFR silencing and reduce EGFR protein level was investigated. Western blot was performed to evaluate EGFR protein expression. As shown in FIGS. 4A-4B and 4E-4F, HEH, but not HER2 aptamer, can reduce EGFR expression after 72 h treatment in SKBR3 and BT474 cells. HEH and HER2 aptamer can upregulate Cleaved Caspase-3 in SKBR3 and BT474 cells, while HEH showed higher levels of Cleaved Caspase-3 than HER aptamer only.

Next, the ability of HER2 aptamer to behave like antibody was evaluated. It has been well documented that antibody upon binding to its cell surface receptors can induce receptor-mediated endocytosis and initiate degradation of bound receptors. As shown in FIGS. 4C-4D and 4G-4H, after 72 h treatment, both HER2 aptamer and HEH indeed can significantly reduce HER2 protein expression. The results indicate that co-targeting EGFR and HER2 with HEH enables down regulation of both EGFR and HER2 and effective upregulation of apoptotic executioner Caspase-3, which has translated into inhibit cell growth and induce cell apoptosis on HER2 expressing cancer cell lines.

Figure 5A:
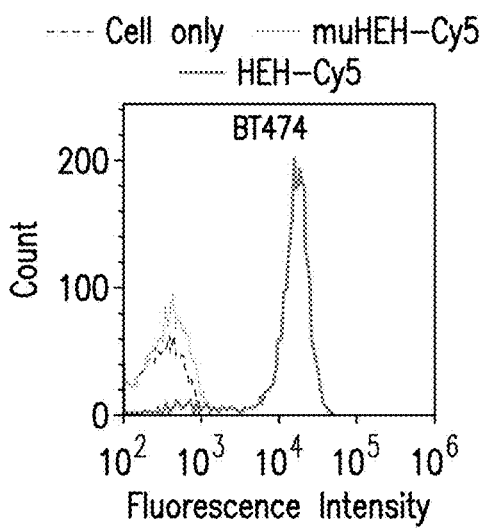
FIGS. 5A-5E are a panel of line graphs showing the evaluation of cell binding specificity by flow cytometry. HER2 positive and HER2 negative breast cancer cell lines were incubated with Cy5 labeled HEH or muHEH, for 1 h at 37° C., and detected with flow cytometry.
Figure 5B:
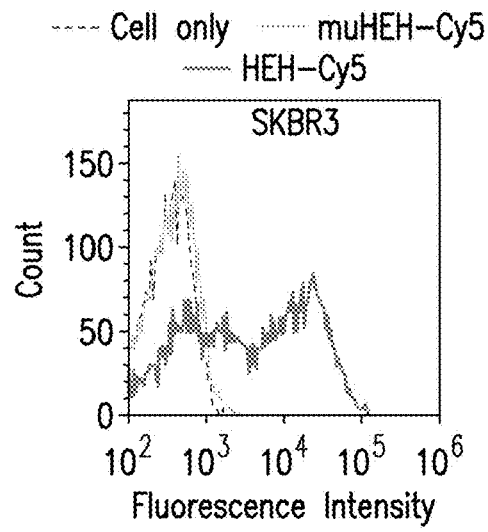
Figure 5C:
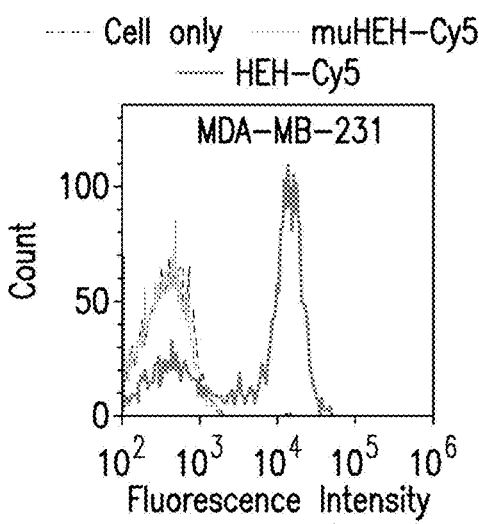
Figure 5D:
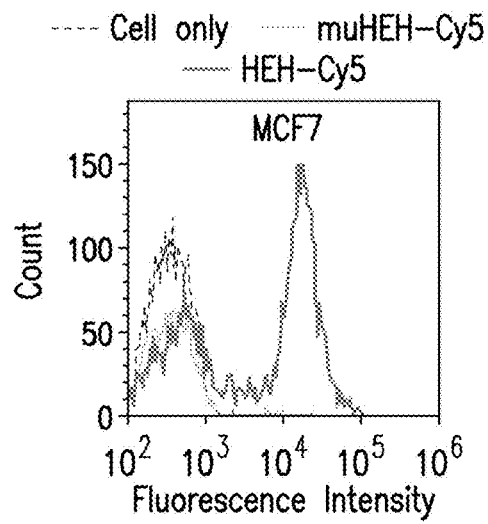
Figure 5E:
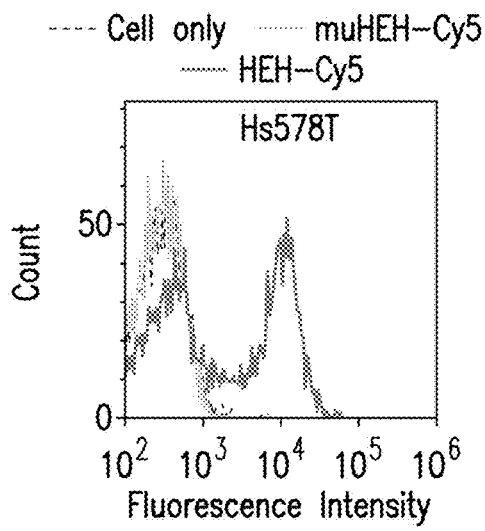

Example 5: HEH Showed Cell Binding Specificity that is Correlated with HER2 Protein Expression Results:
To explore if HEH has different binding patterns on breast cancer cell lines, breast cancer cells were incubated with Cy5-HEH or Cy5-muHEH and detected with flow cytometry. As shown in FIG. 5A, BT474 cells are all positive for HEH. SKBR3 has two populations: one is HEH negative and other one is HEH high expression (FIG. 5B). Interestingly, MDA-MB-231, MCF7, and Hs578 T also have two cell populations: one is HEH negative and other has certain amount HEH positive (FIGS. 5C-5E). As shown in FIG. 1B, indeed, MDA-MB-231, MCF7, and Hs578 T express low amount HER2. Previous studies by immunohistochemistry have shown that MDA-MB-231, MCF7, and Hs578 T indeed express low HER2 but not null or absence of HER2. HEH can differentiate SKBR3, MDA-MB-231, MCF7, and Hs578T into two populations that may suggest bivalent aptamer is more sensitive to detect HER2 expressing cells.

Example 6: HEH Possesses High Tumor-Targeting Capability In Vivo

Results:
To explore tumor-targeting capability and biodistribution of HEH in vivo, tumor-bearing mice (BT474 cell derived xenografts) were i.v. injected with Cy5-HEH or Cy5-mHEH. Biodistribution was monitored with Xenogen IVIS 100 imaging system. As shown in FIG. 5G, after 3 h, in HEH treated mice, Cy5 signals can be clearly visualized in tumor sites. The Cy5-HEH signals can last for 12 h in tumor sites (FIG. 5H). However, in muHEH treated mice, the signals of chimera in tumor site are not clear in 3 h and muHEH chimera has been cleared from the body after 12 (FIGS. 5K-5O). The results showed that HEH has tumor targeting capability and its half-life time in vivo can reach 12 h. In HEH- and muHEH-treated groups, after 24-h injection, Cy5 signals disappeared in main bodies except tails. That also indicates that HEH and muHEH will have shorter deposit time in vivo and may cause less side effect on the normal organs than polymer-based siRNA delivery vehicles.

Example 7: HEH Suppressed HER2 Expressing Breast Tumor Growth

Figure 6A:
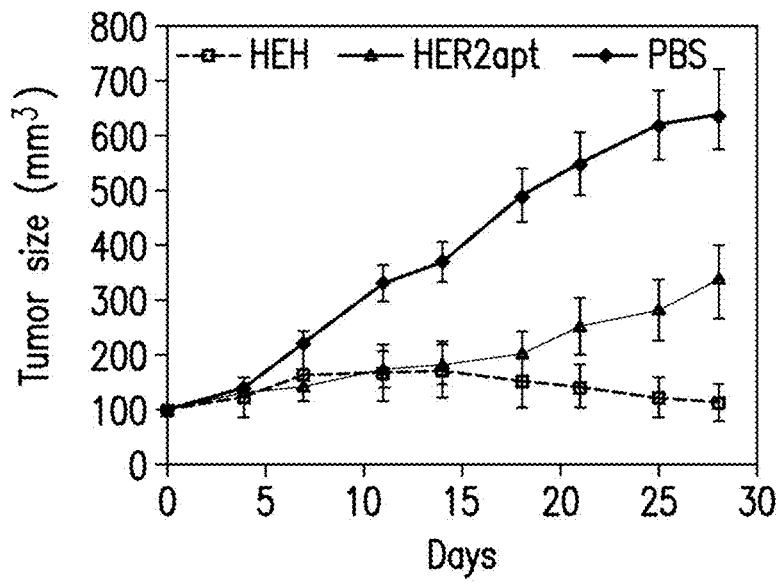
FIG. 6A is a line graph showing a tumor growth curve. Tumor sizes were measured twice a week with digital calipers (n=4).
Figure 6B:
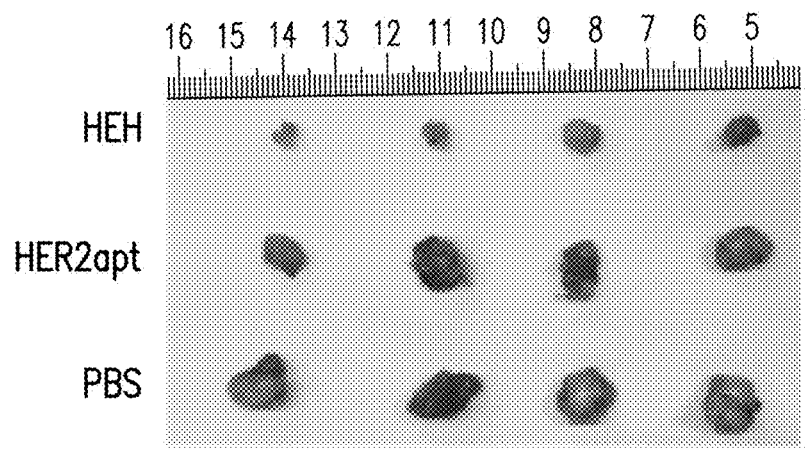
FIG. 6B is a photograph of dissected tumors after treatment.
Figure 6C:
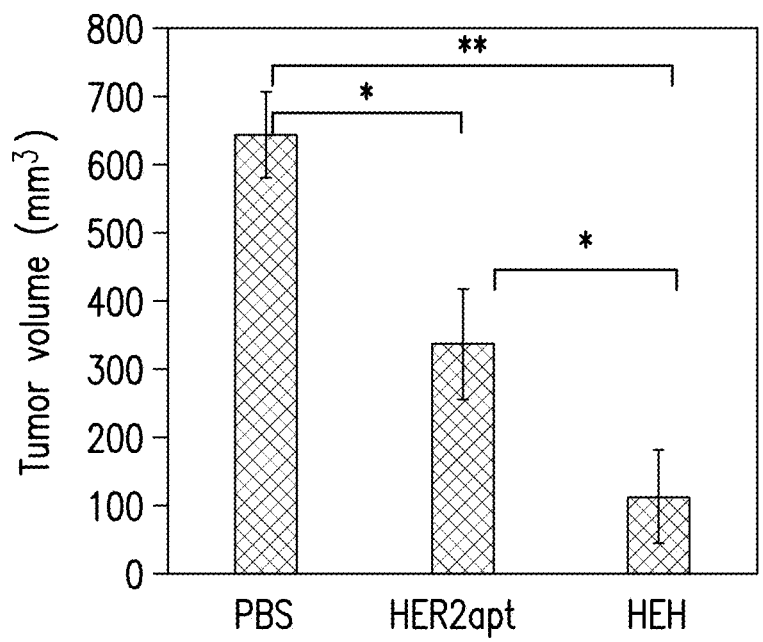
FIG. 6C is a bar graph showing quantitation of dissected tumor size from FIG. 6B (n=4).
Figure 6D:
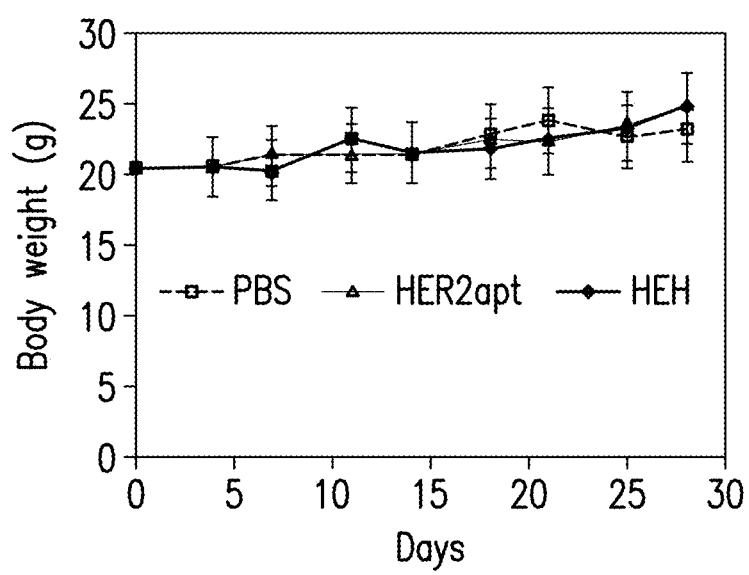
FIG. 6D is a line graph showing body weight measured and averaged (n=4). *p<0.05; **p<0.005. Data represent the mean±SEM.

Results:
Because HEH can reduce protein expression of HER2 and EGFR and trigger cell apoptosis in vitro, treatment efficacy was evaluated to determine if it can be demonstrated in vivo. BT474 cells were implanted into one flank of athymic nude female mice, after tumor size reach about 100 mm, HEH (10 nmoles) was intraperitoneally injected into tumor bearing mice three times per week for 4 weeks. Tumor growth was measured weekly with digital caliper meter. As shown in FIGS. 6A-6C, HEH treatment showed pronounced tumor growth inhibition compared with PBS- and HER2 aptamer-treated tumors. HEH treatment has achieved 5-6-fold reduction in tumor sizes compared with the PBS-treated tumors, and two-fold reduction compared with HER2 aptamer treated tumors. HER2 aptamer treatment has one-fold reduction of tumor size compare with PBS controls. These results suggest that co-targeting of HER2 and EGFR has synergistic efficacy in treating HER2 expressing tumors and is superior to HER2 single targeted treatment. Through time-course measurement of body weight (FIG. 6D), there is no any changes after HEH and HER aptamer treatments compared with PBS controls.

Example 8: HEH Is Capable of Reducing Protein Levels of HER2 and EGFR and Triggering Cell Apoptosis In Vivo Results:
To confirm treatment efficacy, HE staining on excised tumors was performed. As shown in FIGS. 7A-7C, compared with PBS control, HEH treated tumors were highly vacuolated and contained highly condensed nucleus and cytoplasm. To validate if the observed histological alteration correlated with the occurrence of apoptosis, representative tumor samples were analyzed by IHC to evaluate apoptosis maker, Cleaved Caspase-3.

As shown in FIGS. 7J-7L, the intensity of cleaved caspase-3 was increased in HEH-treated tumors compared with PBS- and HER2 aptamer-treated groups. Furthermore, to verify if treatments have reduced HER2 and EGFR in vivo, tumors were examined by IHC staining for detection of HER2 and EGFR expression. As shown in FIGS. 7D-7I, HEH is capable of significantly reducing HER and EGFR in tumor tissue, while HER aptamer alone can reduce HER2 receptor but not EGFR receptor. These findings are consistent with in vitro results in FIGS. 4A-4H. These histology results suggest that HEH enables intervention of EGFR/

HER2 concomitantly and inducing apoptosis in vivo, which is translated into significant suppression of tumor growth in xenograft models.

Figure 8O:
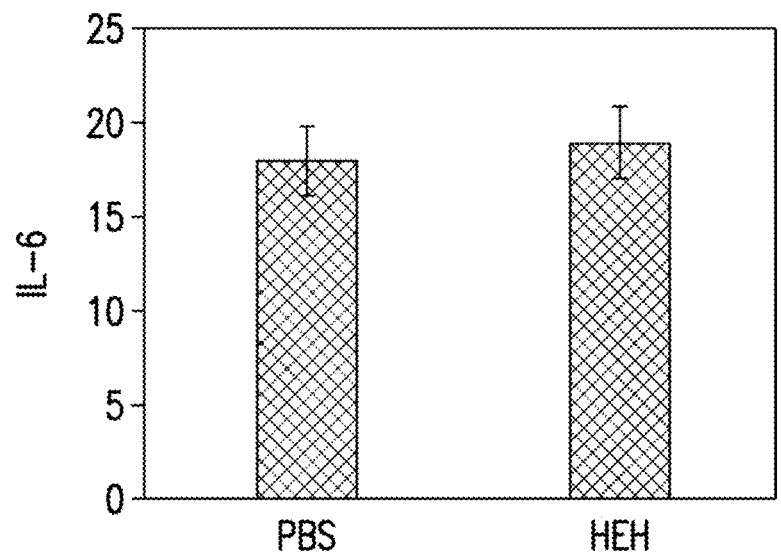
FIG. 8O is a bar graph showing detection of mouse serum for IL-6. The results are the mean±SEM (N=4).

Example 9: There is No Detectable Systemic Toxicity after HEH Treatment in Xenografts Results:

To evaluate potential systemic toxicity, after 4-week treatment, HE staining was performed on major organs including brain, heart, intestine, kidney, liver, lung, and spleen. There is no obvious histological difference between PBS- and HEH-treated mice (FIGS. 8A-8N). IFNα and IL-6 in mouse sera have been evaluated with ELISA shown in Table 1 and FIG. 8O. No statistical difference was identified for IFNα and IL-6 between PBS and HEH groups. That indicates that HEH does not have acute toxicity and not trigger innate immune response. That is consistent with the evaluations from many RNA based chimeras in vivo applications.

TABLE 1

Detection of mouse serum IFNα.

| Standard | | Mouse sera | |
| --- | --- | --- | --- |
| IFNα (pg/ml) | OD450 | Groups | OD450 |
| 0 | 0.160 ± 0.012 | PBS | 0.159 ± 0.03 |
| 12.5 | 0.215 ± 0.015 | | |
| 25 | 0.356 ± 0.031 | HEH | 0.130 ± 0.04 |
| 50 | 0.461 ± 0.033 | | |
| 100 | 0.945 ± 0.044 | | |

Example 10: Detection of Annealed HEH with 3% Agarose

Figure 9:
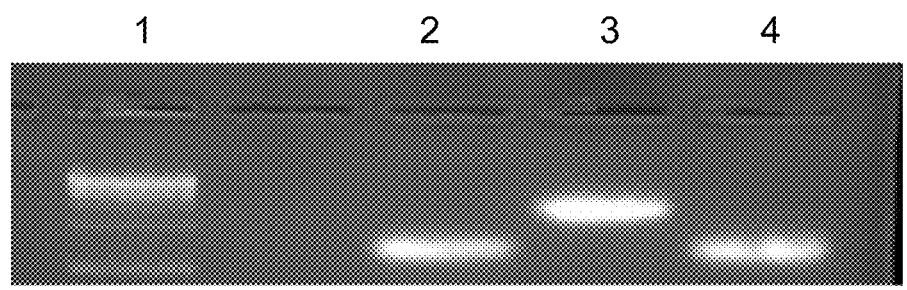
FIG. 9 is an agarose gel showing annealed HEH.

Results:

To generate HEH, equal moles of HER2 aptamer-EGFR siRNA sense strand and HER2 aptamer-EGFR siRNA antisense strand were mixed together and heated to 95° C. for 3 min, followed by slowly cooling to room temperature. After annealing, in HEH lane, no free aptamer-EGFR siRNA sense strand or HER2 aptamer-EGFR siRNA anti-sense strand is detectable. Lane 1: Molecular weight marker; Lane 2: HER2 aptamer-EGFR siRNA sense strand; Lane 3: annealed HEH; Lane 4: HER2 aptamer-EGFR siRNA anti-sense strand (FIG. 9).

Figure 10A:
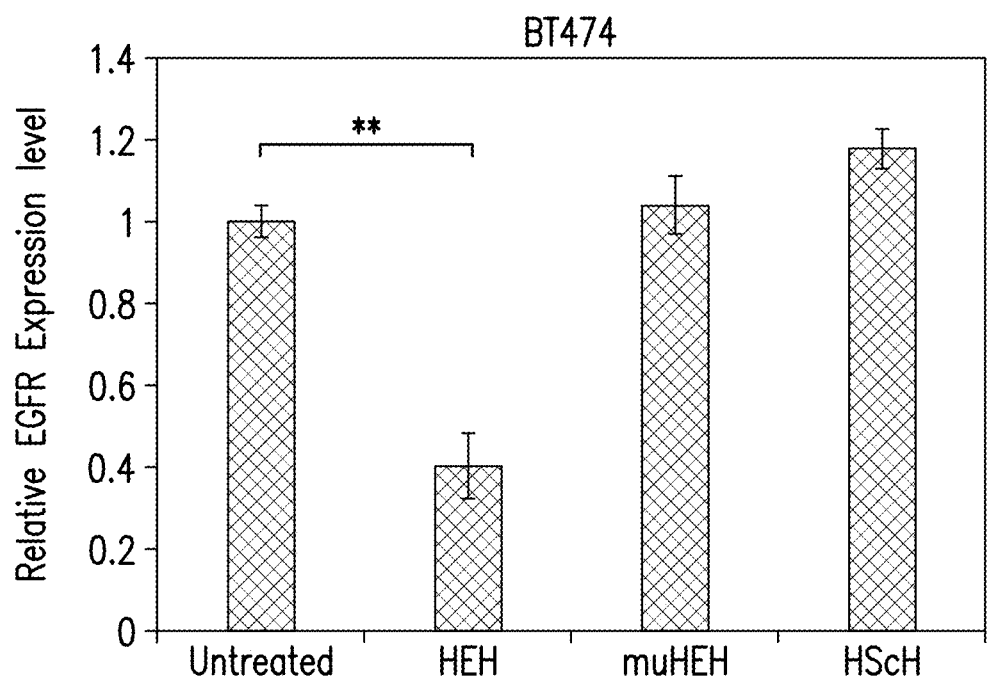
FIG. 10A is a bar graph showing the detection of EGFR mRNA with qRT-PCR in BT474 cells.
Figure 10B:
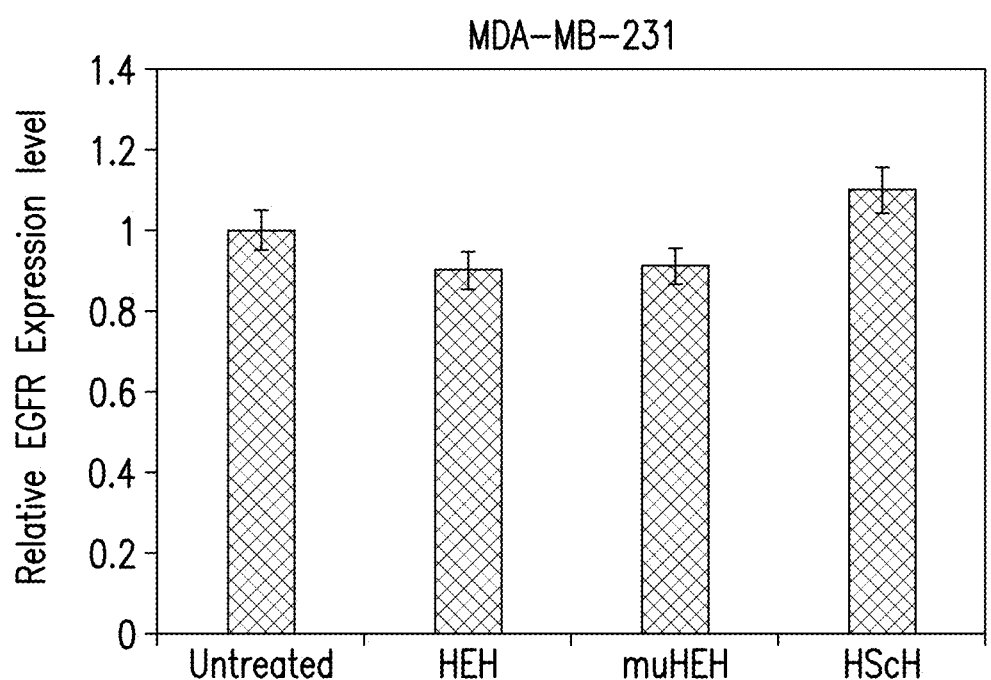
FIG. 10B is a bar graph showing the detection of EGFR mRNA with qRT-PCR in MDA-MB-231 cells.

Example 11: Detection of EGFR mRNA with qRT-PCR in BT474 and MDA-MB-231 Cells HER2 positive BT474 cells and HER2 negative MDA-MB-231 cells were treated with HEH, muHEH or HER2 aptamer-scrambled siRNA at 2 μM for 48 h. RNA was extracted and reverse transcribed as described in material and methods. Gene copy numbers were normalized against GAPDH (FIGS. 10A and 10B). *P<0.05. **P<0.001.

Example 12: Detection of HEH Internalization by Z-Stack Confocal Microscopy

Cy5-labeled HEH, EGFRsiRNA, HER2 aptamer, or muH2EH3 was individually added into BT474 cells for 12 h at 37° C. LysoTracker Green was used to show lysosomes and endosomes. DAPI was used to display nucleus. Confocal laser scanning microscopy with z stack was performed to show cell binding and internalization. As a cell control, HER2 negative MDA-MB-231 cells were treated with Cy5-HEH for 12 h at 37° C. and the internalization was determined with Z-stack confocal microscopy.

Example 13: Engineering of a Three-in-One Aptamer-siRNA Chimera. HER2 Aptamer-EGFR siRNA-HER3 Aptamer Materials and Methods:

Chemicals and Cell culture. Vendors for specific chemicals are listed below. Cell culture products were purchased from Life Technologies (Carlsbad, Calif.). Antibodies were from Cell Signaling Technology (Danvers, Mass.). Single stranded DNAs were synthesized by Integrated DNA Technologies (IDT, Coralville, Iowa). TranscriptAid T7 High Yield Transcription Kits were purchased from Thermo Fisher Scientific. HER2 and HER3 siRNAs were purchased from Life Technologies Corporation. LysoTracker Green DND-26 and Alexa Fluor 488 Annexin V/Dead Cell Apoptosis kits were from Invitrogen. ELISA kits for detection of IFNα and IL-6 were obtained from RayBiotech (Norcross, Ga.). TUNEL assay kit was purchased from R&D systems (Minneapolis, Minn.). 2'Fluoro-2'-deoxycytidine-5'triphosphate and 2'-Fluoro-2'-deoxyuridine-5'-triphosphate, and Cy5 labeled 2'fluoro-labeled HER2 aptamer were purchased from TriLink Biotechnologies (San Diego, Calif.). Cell lines were purchased from the American Type Culture Collection (ATCC, Manassas, Va.). Human serum (Normal Pool) was obtained from Thermo Fisher Scientific.

Aptamer-siRNA Chimera synthesis. The ssDNA templates and primers were synthesized from IDT.

For H2EH3 chimera synthesis, RNA1 (HER3 aptamer-EGFR antisense siRNA): 5'-GAAUUCCGCGU-GUGCCAGCGAAAGUUGCGUAUGGGUCACAUCG CAGGCACAUGUCAUCUGGGCGGUCCGUUCGG-GAUCCAAAAUUAGA UAAGACUGCUAAGGCA-3'. (SEQ ID NO:20)

RNA1 PCR template: 5'-GAAT-TCCGCGTGTGCCAGCGAAAGTTGCGTA TGGGTCA-CATCGCAGGCACATGT-CATCTGGGCGGTCCGTTCGGGATC CAAAATTAGATAAGACTGCTAAGGCA-3'. (SEQ ID NO:21)

RNA1 5' primer: 5'-TAATACGACTCACTATAGAAt-tCCGCG tGtGCCA-3'. (SEQ ID NO:22) The forward primer contains T7 RNA polymerase promoter site (bolded).

RNA1 3' primer: 5'-TGCCTTAGCAGTCTTATCTAAT-TTTGGATCCCGA-3'. (SEQ ID NO:23)

RNA2 (HER2 aptamer-EGFR sense siRNA): 5'-AGCCGCGAGGGGAGGG AUAGG-GUAGGGCGCGGCUAAAACCUUAGCAGUCUUAUC-UAAUU-3'. (SEQ ID NO:24)

RNA2 PCR template: 5'-AGCCGCGAGGGGAGGGA-TAGGGTAGGGCG CGGCTAAAACCTTAGCAGTC TTATCTAATT-3'. (SEQ ID NO:25)

RNA2 5' primer: 5'-TAATACGACTCAC-TATAAGCCGCGAGGGGAG GGA-3'. (SEQ ID NO:2) The forward primer contains T7 RNA polymerase promoter site (bolded).

RNA2 3' primer: 5'-AATTAGATAA-GACTGCTAAGGTTTTA-3'. (SEQ ID NO:3)

Three RNAs were generated by in vitro transcription with PCR products as templates. The PCR products were put into T-A cloning pCR2.1 vector (Invitrogen) and sequenced. Transcription was performed with Transcript Aid T7 High Yield Transcription Kit following manufacture's instruction. 2' F-modified pyrimidines were incorporated into RNAs to replace CTP and UTP. The transcribed RNAs were purified following the methods described in Zheng, et al., *Theranostics*, 7: 1373-1388 (2017); Liu, et al., *Sci Rep*, 6:30346 (2016). Two RNAs were mixed at molar ratio 1:1 and annealed to form one entity by heating at 94° C. for 3 min followed by slowly cooling to room temperature within 1 h. For HER3 aptamer (RNA 3) synthesis, RNA1 PCR template (SEQ ID NO:21) and RNA1 5' primer (SEQ ID NO:22) were used as above, and RNA3 3'primer is 5'-GGAUCCC GAACGGACCGCCCA-3'. (SEQ ID NO:26)

For HER2 aptamer (RNA 4) synthesis, RNA2 PCR template (SEQ ID NO:25) and RNA 2 5' primer (SEQ ID NO:2) were used as above, RNA4 3'primer is 5'-AGCCGCG CCC-TACCCTATCCCT-3'. (SEQ ID NO:6)

For MG aptamer (RNA 5) synthesis, RNA 5: 5'-GGAUCCCGACUGGCG AGAGCCAG-GUAACGAAUG GAUCC-3'. (SEQ ID NO:27)

RNA5 PCR template: 5'-TAATACGACTCACTATAG-GATCCCG ACTGGCGAGAGCCAGG TAAC GAATG-GATCC-3'. (SEQ ID NO:28)

RNA5 5'primer: 5'-TAATACGACTCACTATAG-GATCCCGACTGGC-3'. (SEQ ID NO:29)

RNA5 3'primer: 5'-GGATCCATTCGTTACCT-3'. (SEQ ID NO:30)

The PCR products were transcribed into RNA3, RNA 4 and RNA 5, which were annealed into HER3, HER2 and MG aptamers individually.

For mutant H2EH3 synthesis. RNA 6 (mutant HER3 aptamer-EGFR antisense siRNA). PCR template (IDT):

(SEQ ID NO: 31)
5'GAAttCCGCGtGtGCCAGCGAAAGttGCGtAtGGGtCACAtCGCAca ggacgttCAtCtGGGCGGtCCGttCGGGAtCCAAAAUUAGAUAAGACUG

CUAAGGCA-3'

RNA6 5'-primer:
(SEQ ID NO: 32)
5'-TAATACGACTCACTATAGAAttCCGCGtGtGCCA-3'

RNA6 3'-primer:
(SEQ ID NO: 23)
5'-TGCCTTAGCAGTCTTATCTAATTTTGGA-3'

RNA7 (mutant HER2 aptamer-EGFR sense siRNA).
PCR template (IDT):
(SEQ ID NO: 33)
5'-AGCCAAACGAGGGGGGAGAGGGTGGGGCGCCTGAAAACCTTAGCA

GTC TTATCTAATT-3'

RNA7 5'-primer:
(SEQ ID NO:34)
5'-TAATACGACTCACTATAAGCCAAACGAGGGGGGAGAGGGT-3'

RNA7 3'-primer:
(SEQ ID NO: 9)
5'-AATTAGATAAGACTGCTAAGGTTTTCA-3'

As above procedures, the PCR products were transcribed into RNAs. RNA6 and RNA7 were annealed into mutant H2EH3. Cy5-labeled aptamers were synthesized by TriLink Biotechnologies Dicer assay. H2EH3 (4 µg) was digested using human recombinant dicer enzyme (2 units) at 37° C. for 12 h following manufacturer's instructions (Genlantis, San Diego, Calif.). Reaction was quenched by adding dicer stop solution. The digestion pattern was analyzed on 3.5% agarose gel electrophoresis.

Results

A three-in-one aptamer siRNA chimera was designed to target three important oncogenes: EGFR, HER2, and HER3, respectively. The 3'-terminus of HER3 aptamer (79 bases) (Chen, et al., *Proc Natl Acad Sci USA*, 100: 9226-9231 (2003)) was fused with the anti-sense strand of EGFR siRNA, and the 3'-terminus of HER2 aptamer (34 bases) (Kim, et al., *Nucelic Acid Ther*, 21: 173-178 (2011)) was fused with the sense strand of EGFR siRNA. $K_d$ value of HER2 aptamer is 3.49 nM, and $K_d$ value of HER3 aptamer is 45 nM., 2-4 unpaired "A" s were inserted between an aptamer and an siRNA to offer spatial flexibility to each aptamer (FIG. 11A). Through in vitro transcription, 2'-fluoro pyrimidines were incorporated into two RNA chains to enhance serum stability. Two transcripts with 19-base complementing sequences (sense strand and antisense strand of EGFR siRNA) were annealed together by heating 3 min at 95° C. followed by slowly cooling to room temperature within 1 hour. As shown in FIG. 11A, the new chimera with one HER2 aptamer (MW 11.2 $K_d$), one EGFR siRNA, and one HER3 aptamer (MW 25.4 $K_d$) was annealed into one molecule with molecular weight 55.4 Kd, which is larger than each single aptamer, and larger than renal glomerulus cutoff mass (30-50$K_d$), but smaller than antibody (about 150$K_d$). Thus H2EH3 is expected to have longer circulation time than single aptamer alone. Ma, et al., *Nature*, 429: 318-322 (2004) put the 3' end of the anti-sense strand of EGFR siRNA with a 2-nt overhang which promotes siRNA-RISC (RNA-induced silencing complex) formation.

Figure 11B:
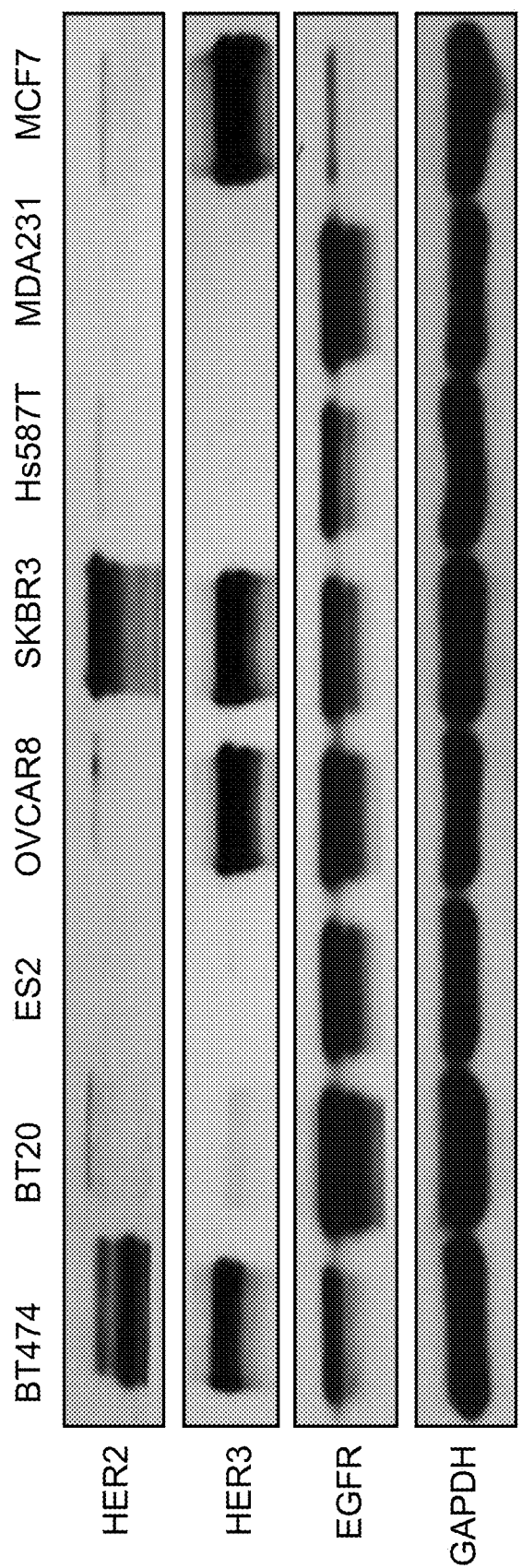
FIG. 11B is an autoradiograph showing detection of HER2 and EGFR expression in breast cancer cell lines by Western blot.
Figure 11C:
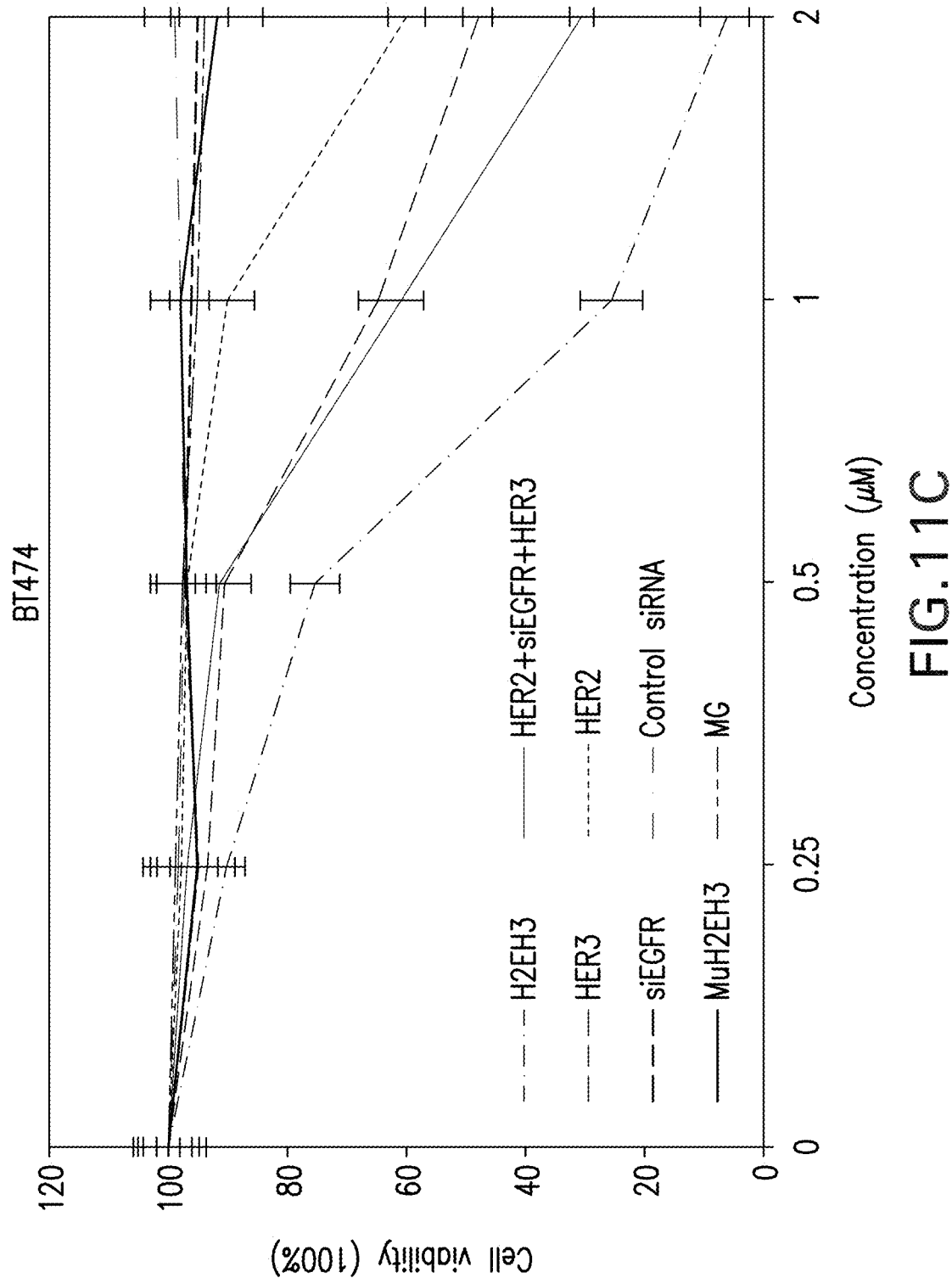
Figure 11E:
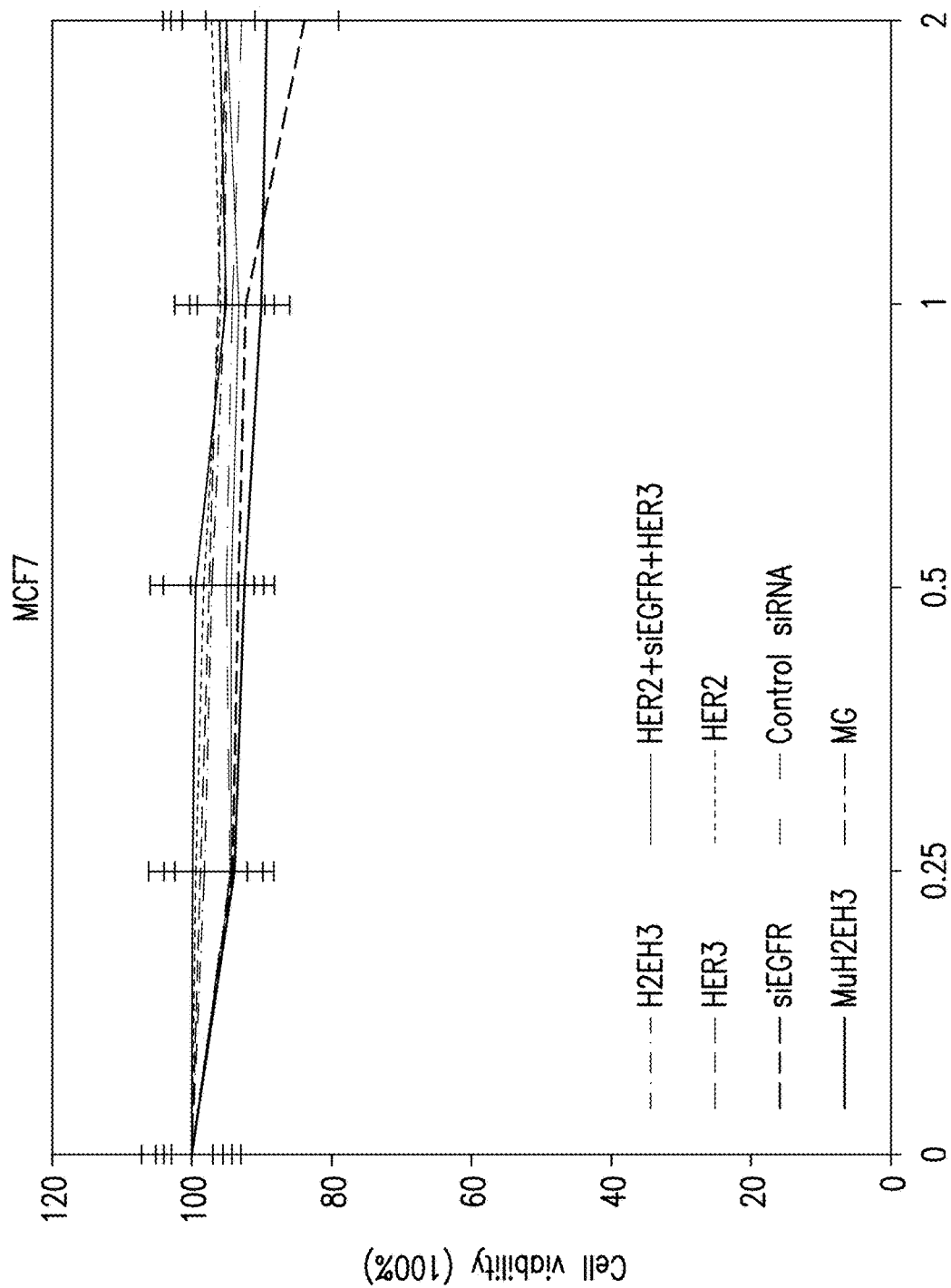
Figure 11F:
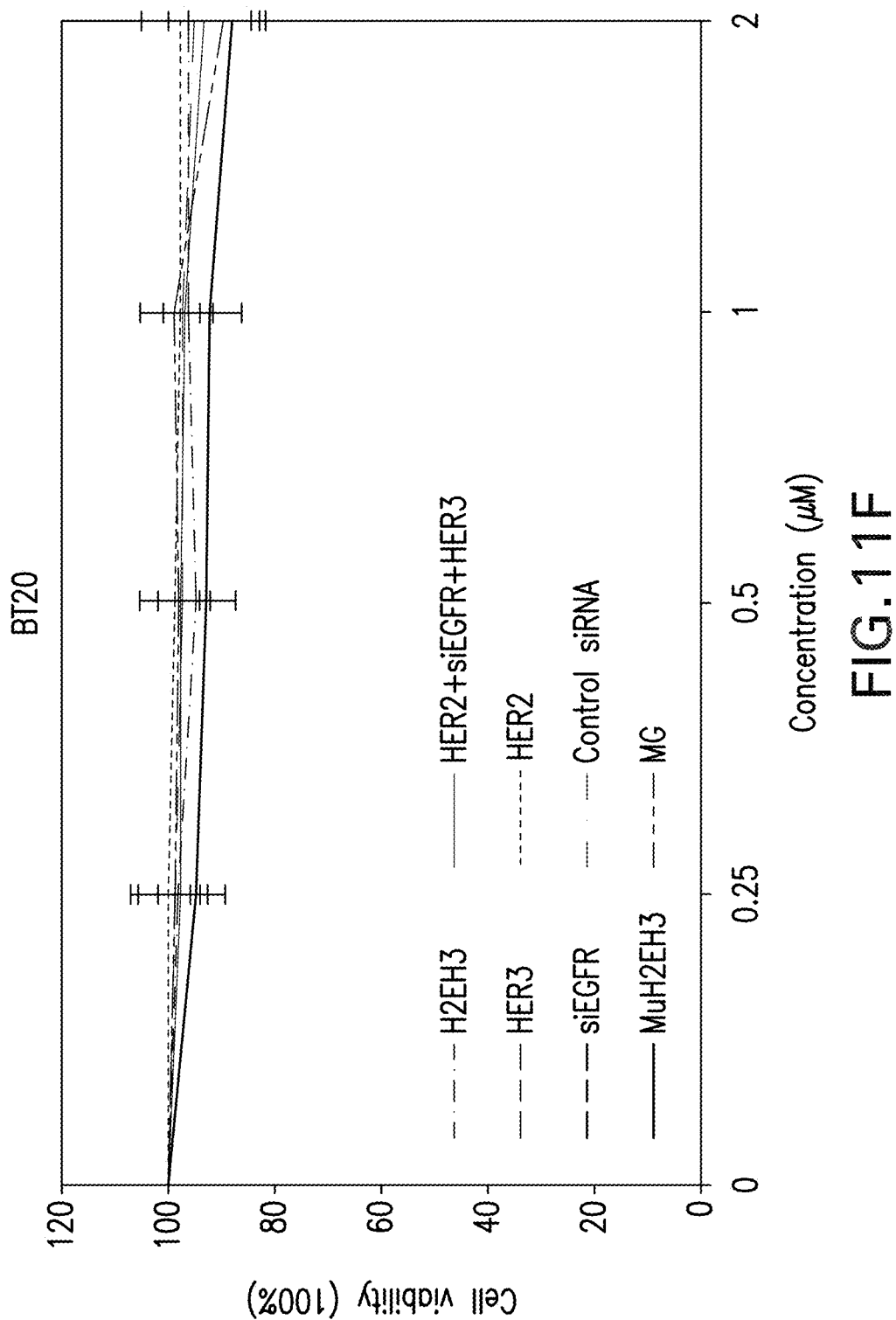
Figure 11G:
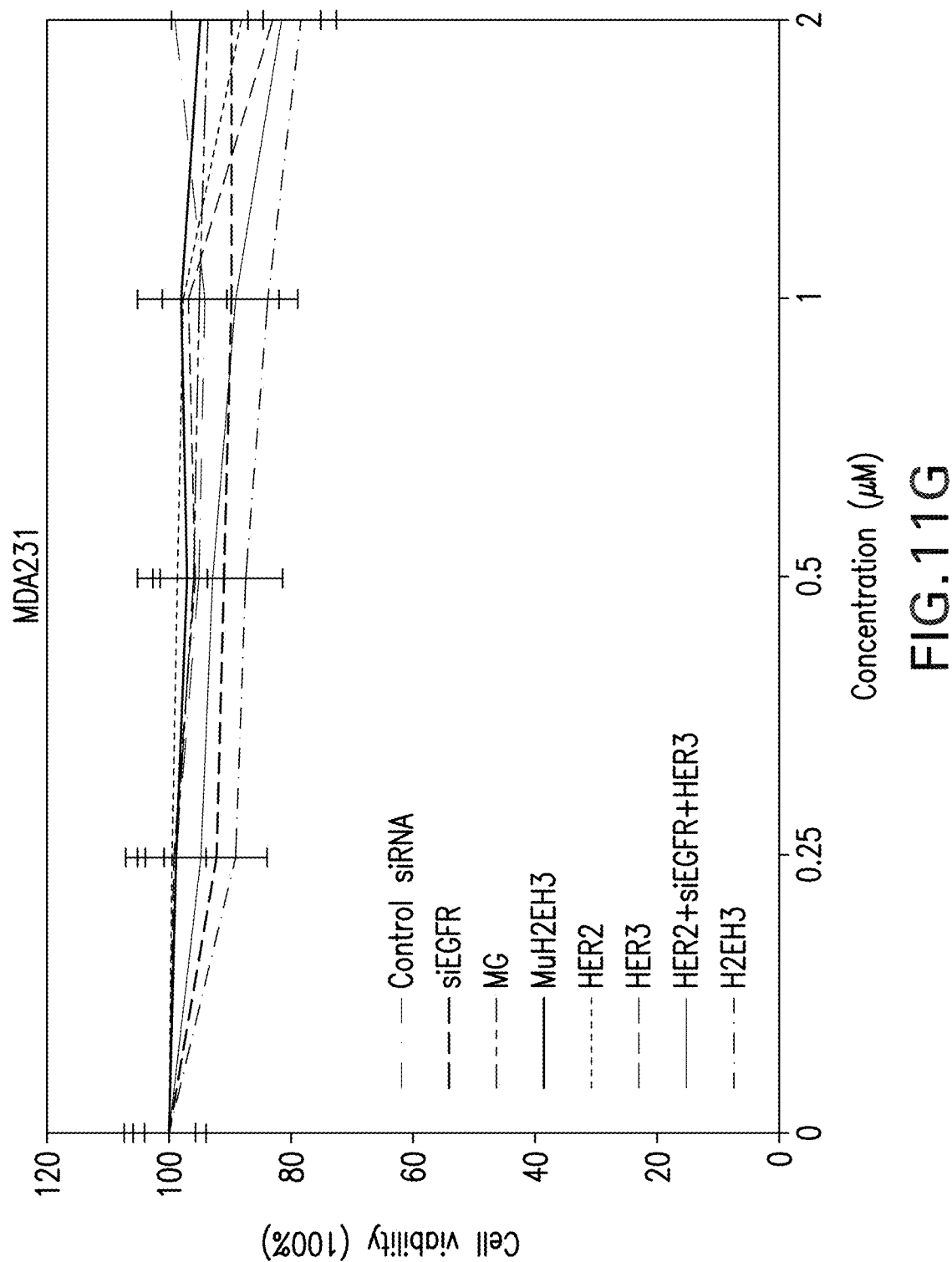
Figure 11H:
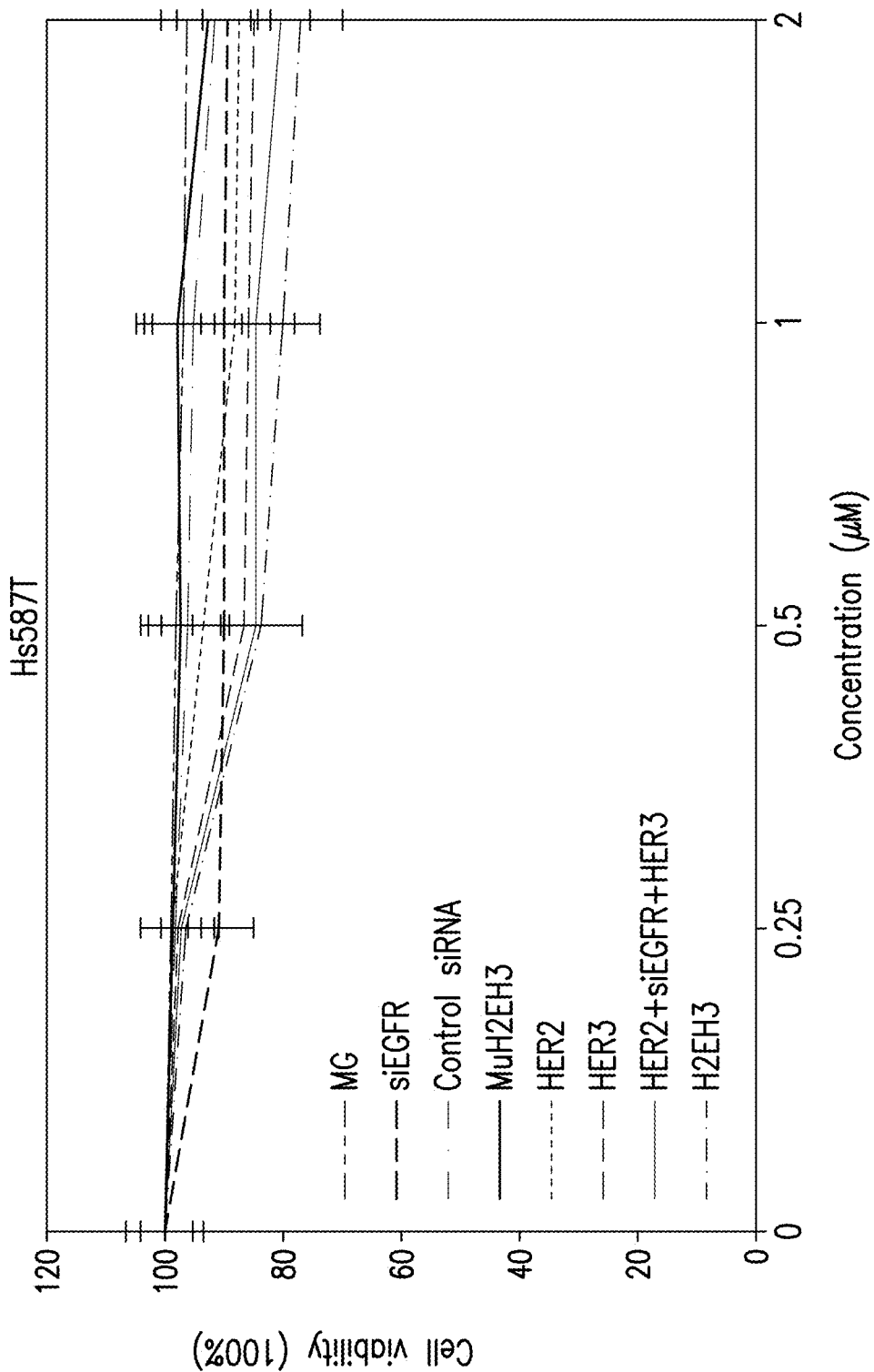
Figure 11I:
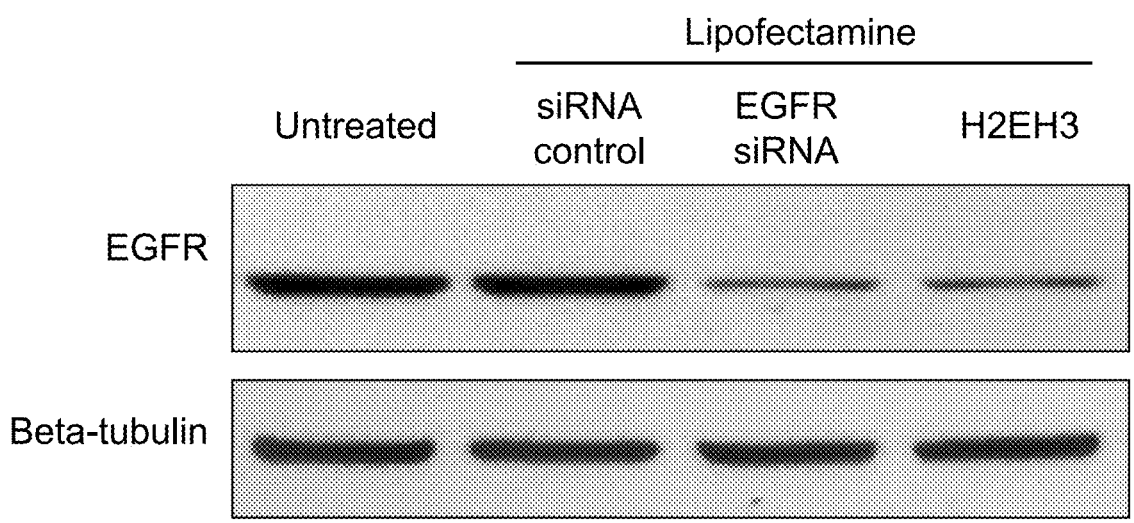
FIG. 11I is a Western blot showing EGFR-silencing capability of H2EH3.
Figure 11J:
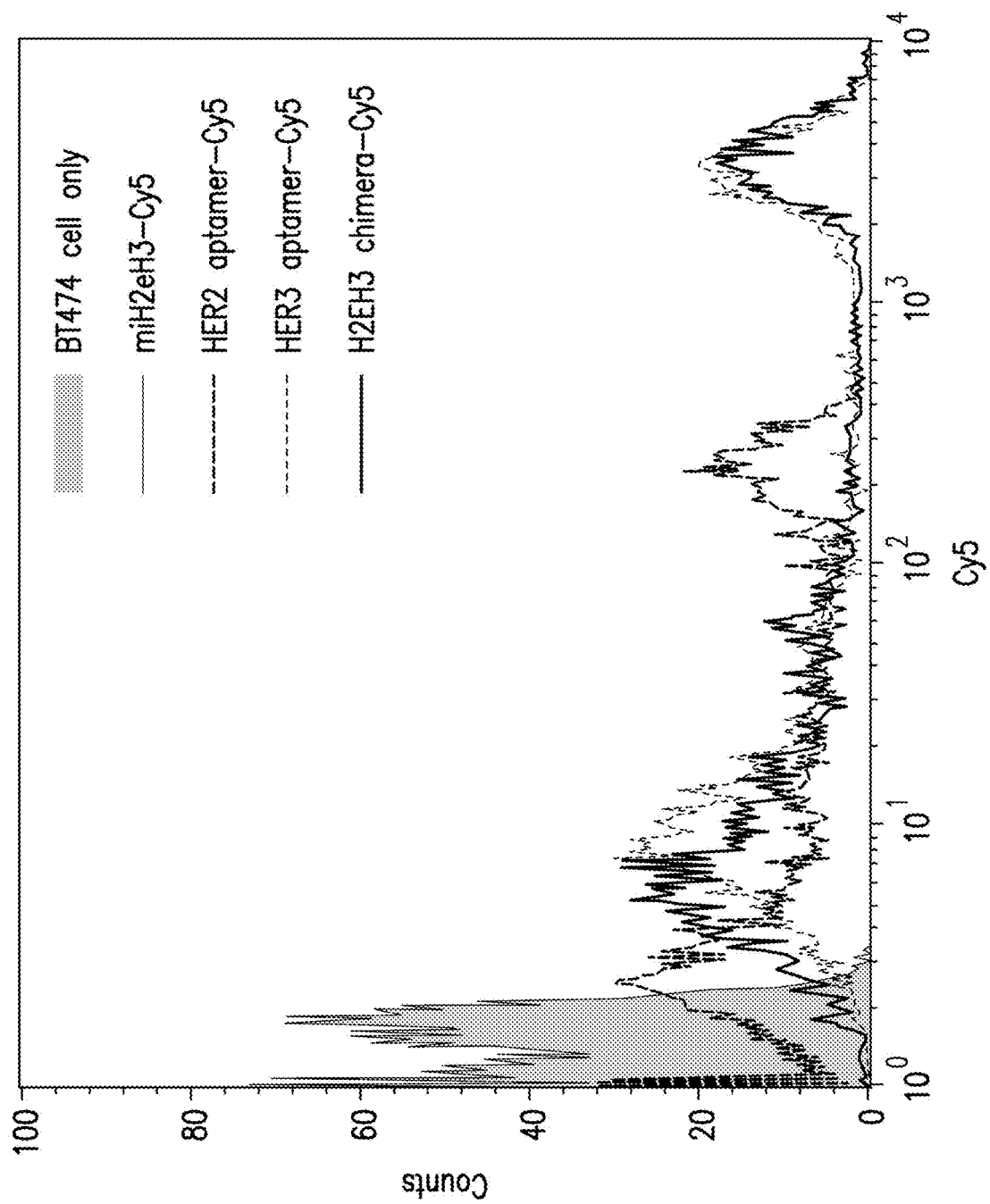
FIG. 11J is a line graph showing H2EH3-binding capability compared with HER2 aptamer and HER3 aptamer.

H2EH3 possesses the activities of HER2 aptamer, EGFR siRNA and HER3 aptamer. The binding affinity of H2EH3 compared with HER2 aptamer and HER3 aptamer individually was investigated. H2EH3 showed strong binding affinity comparable with HER2 aptamer and HER3 aptamer (FIG. 11J). To detect EGFR silencing activity of H2EH3, BT474 cells were transfected with H2EH3 using lipofectamine. As shown in FIG. 11I, H2EH3 has similar silencing effect as EGFR siRNA. In addition, H2EH3 was incubated with dicer for 12 h. The result showed that H2EH3 digested with dicer released an RNA fragment with the same size as EGFR siRNA. This suggests that H2EH3 can be processed with RNA interference machinery.

Example 14: H2EH3 Cytotoxicity

Materials and Methods

Cytotoxicity assay. Cellular cytotoxicity was quantified by measuring WST-8 formazan using Cell Counting Kit-8 (CCK-8) (Dojindo, Japan). Cells were seeded in 96-well plate at a density of $5 \times 10^3$ in 5% $CO_2$ incubator for 24 h at 37° C. Cell lines were incubated with the varying concentrations of H2EH3 or controls for 72 h without transfection reagents (e.g., Lipofectamine). CCK-8 solution (10 µl) was added to each well and incubated at 37° C. for 4 h. Absorbance at 450 nm was measured using a microplate reader.

Results

H2EH3 cytotoxicity on breast cancer cell lines was evaluated. HER2, HER3, and EGFR expression in breast cancer and ovarian cancer cell lines including BT474, BT20, ES2, OVCAR8, SKBR3, Hs587T, MDA-MB-231 and MCF7 were analyzed by Western blot. As shown in FIG. 11B, BT474 and SKBR3 cells expressed the highest levels of HER2 among all detected cell lines. ES2 and MDA-MB-231 cells were negative to HER2, while BT20, OVCAR8 and Hs587T cell lines showed slightly detectable HER2 expression (FIG. 1B). BT474 and SKBR3 cells also expressed high levels of HER3. OVCAR8 and MCF7 showed high abundance of HER3 with trace levels of HER2. EGFR was expressed in all detected cell lines. MCF7 showed much less expression of EGFR than other cell lines, while BT20 and MDA-MB-231, two triple negative breast cancer cell lines, showed the highest EGFR of the cell lines tested here. BT474 and SKBR3 cells showed moderate expression of EGFR.

The growth inhibitory effect of H2EH3 on these cell lines was examined using a CCK8 cell counting kit. Cell lines were treated with increasing concentrations of H2EH3 or controls including HER2 aptamer, HER3 aptamer, EGFR siRNA, mixture of HER2 aptamer, HER3 aptamer, and EGFR siRNA, non-targeting control aptamer MG (specific to Malachite Green), or mutant H2EH3. As shown in FIGS. 11C-11D, the viability of BT474 and SKBR3 cells exposed to H2EH3 for 72 h was significantly reduced in a dose-dependent manner. BT474 and SKBR3 cells only remained about 5-10% viable upon treatment with 2 µM of H2EH3. Whereas upon treatment with 2 µM of the mixture of HER2 aptamer, HER3 aptamer, and EGFR siRNA, the viability remains 30% for BT474 and 50% for SKBR3. The results suggest that three-in-one H2EH3 is superior to a mixture of the three individual components. HER3 aptamer and HER2 aptamer all showed dose-dependent cytotoxicity for BT474 and SKBR3 cells. The efficacy of HER3 aptamer was more potent than HER2 aptamer. Upon treatment with 2 µM of aptamers, the viability of BT474 was 48% with HER3 aptamer and 60% with HER2 aptamer, similarly, the viability of SKBR3 was 65% with HER3 aptamer and 75% with HER2 aptamer. EGFR siRNA only and MG did not show cytotoxicity to SKBR3 and BT474. Mutant H2EH3 (muH2EH3) was constructed containing the same nucleic acid components as H2EH3 and the same EGFR siRNA as H2EH3 but missing original 3-D conformations of HER2 and HER3 aptamers. MuH2EH3 did not show cytotoxicity to any detected cell lines. MCF7 and BT20 cell lines did not have any response to H2EH3 treatment (FIG. 11E-11F). The viability of MDA-MB-231 and Hs578T cell lines showed 10-20% decrease upon 2 µM of H2EH3 treatments (FIG. 11G-11H). Although MCF7 cells have high HER3 expression but no HER2 expression, HER3 aptamer and H2EH3 did not show inhibitory effects on MCF7 growth (FIG. 11E). Furthermore, MCF7 cell survival was investigated to determine whether it was dependent on HER3. HER3 was silenced in MCF7 cells and cell viability was examined. The cell viability only had 7% decrease, which indicates HER family is not the major survival pathway for MCF7 proliferation. BT20, MDA-231 and Hs578T are both HER2 and HER3 negative, thus it was not surprising that their cell viabilities did not decrease significantly upon H2EH3 treatment. These results suggest that H2EH3 has strong cell-type specific targeting capability.

Example 15: H2EH3 Induces Cell Cycle Arrest and Apoptosis in HER2+HER3+ Cell Lines Materials and Methods Cell cycle analysis. SKBR3 and BT474 cells were treated with the different concentrations of H2EH3 for 24 h and 48 h. Collected cells were fixed in cold 70% ethanol. After fix for 30 min at 4° C., ethanol-fixed cells were centrifuged and washed once with PBS. The cells were treated with RNase A and stained with Propidium Iodide (PI) for 30 min at 37° C. Cellular DNA contents were measured by exciting PI at 488 nm and measuring the emission at 580 nm using a BD FACSCalibur flow cytometer.

Detection of apoptosis by flow cytometry. SKBR3 and BT474 cells were treated with the different concentrations of H2EH3 for 72 h. The cells were harvested and washed in cold phosphate-buffered saline (PBS). Cells were stained with Alexa Fluor 488 Annexin V-Propidium Iodide (PI) solution for 1 h at room temperature. Cells ($1 \times 10^4$/sample) were acquired by BD FACSCalibur and analyzed using BD FACStation software.

Results

The decrease in cell viability may be attributed to reduced cell proliferation and/or increased cell death. To identify these effects, the effect of H2EH3 on cell cycle progression was examined. BT474 and SKBR3 cells were treated with H2EH3 at the different concentrations for 24 h and 48 h. As shown in FIGS. 12A-12F, BT474 cells showed G2/M arrest in 24 h, and showed increased subG1 population from 0.27% of untreated cells to 2.83% of cells treated with 2 µM of H2EH3. That suggests that the apoptosis of BT474 cells occurred after 48-h treatment. SKBR3 cells showed slight G2/M arrest in 24 h and significantly increased subG1 population in 24 h and 48 h, indicating that SKBR3 cells underwent apoptosis within 24 h (FIG. 12O-12T).

Figure 12A:
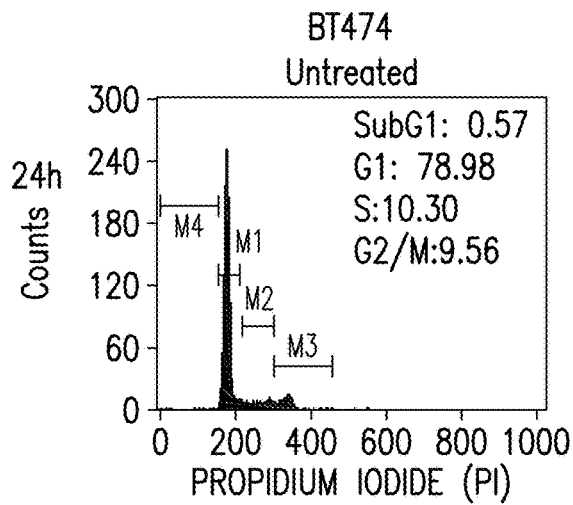
FIGS. 12A-12BB are scatter plots showing the detection of cell apoptosis and death by flow cytometry. BT474 and SKBR3 cells were treated with H2EH3, HScH, and HER2 aptamer for 48 h and 72 h, and then cells were stained with Alexa Fluor 488 Annexin V-Propidium Iodide and analyzed by flow cytometry.
Figure 12B:
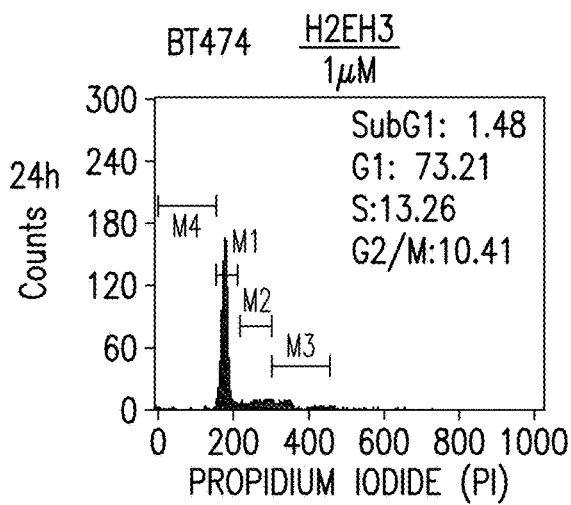
Figure 12C:
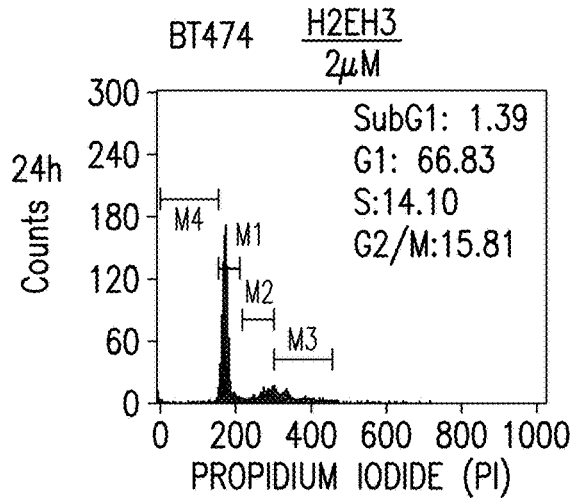
Figure 12D:
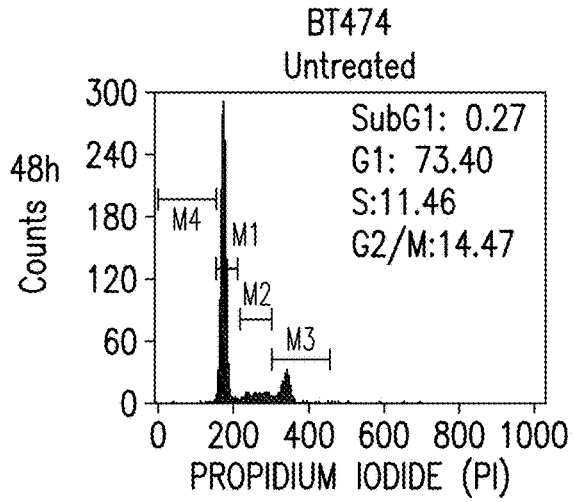
Figure 12E:
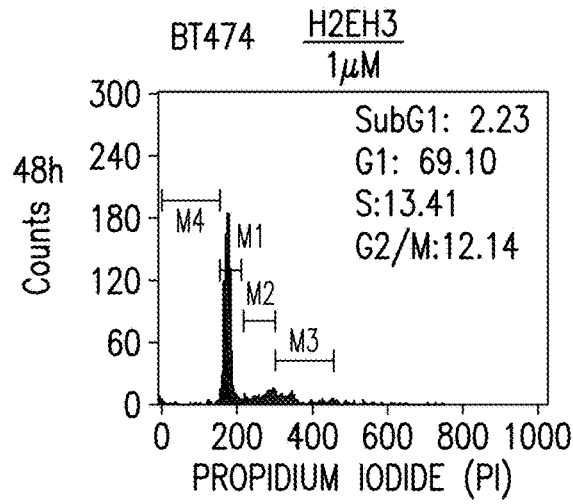
Figure 12F:
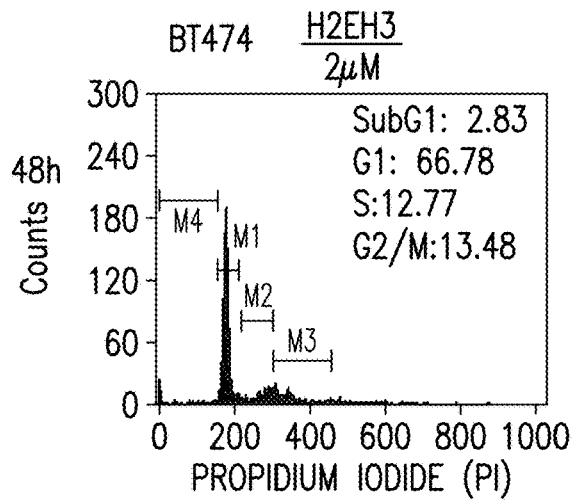
Figure 12G:
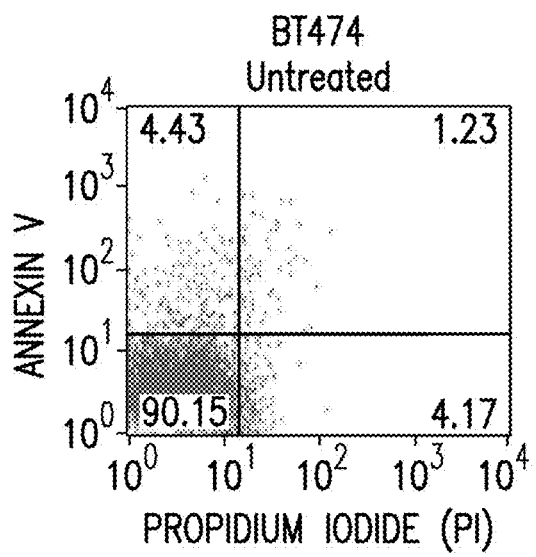
Figure 12H:
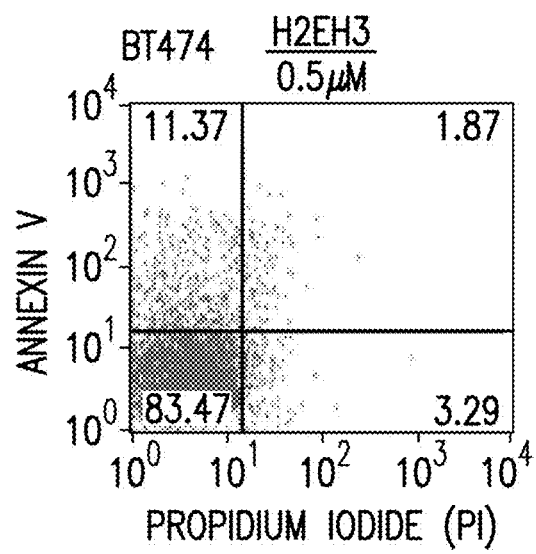
Figure 12I:
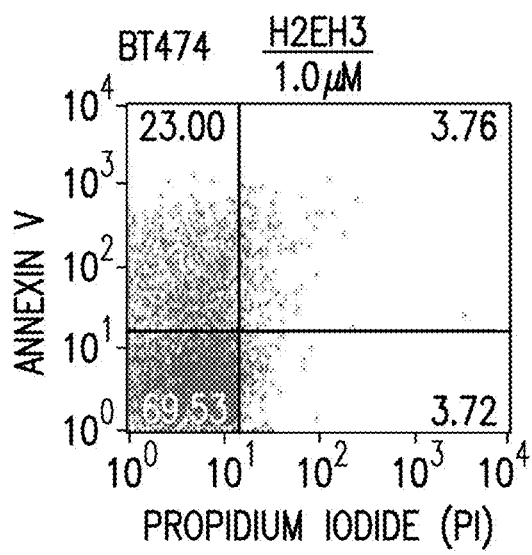
Figure 12J:
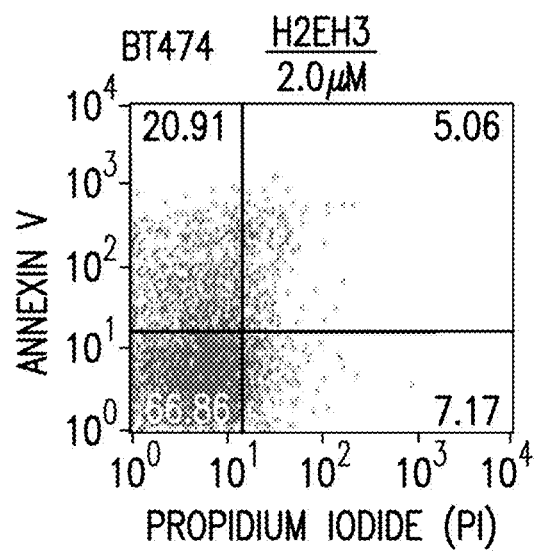
Figure 12K:
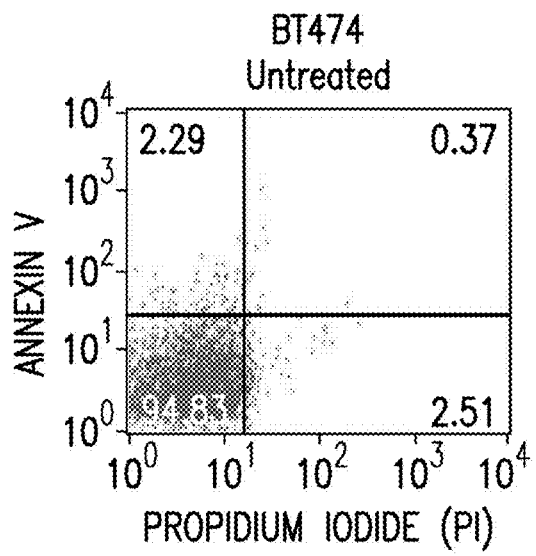
Figure 12L:
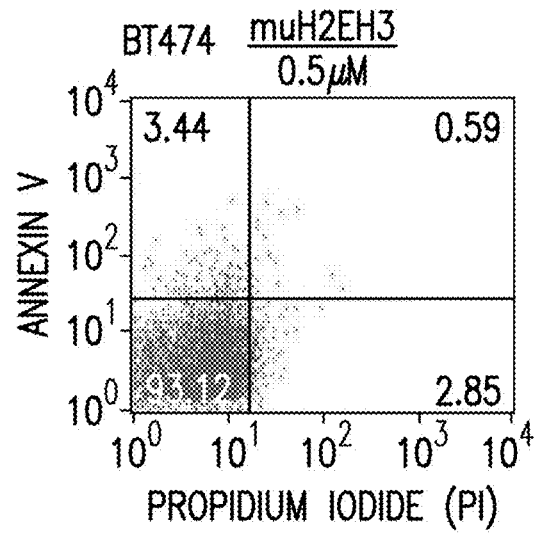
Figure 12M:
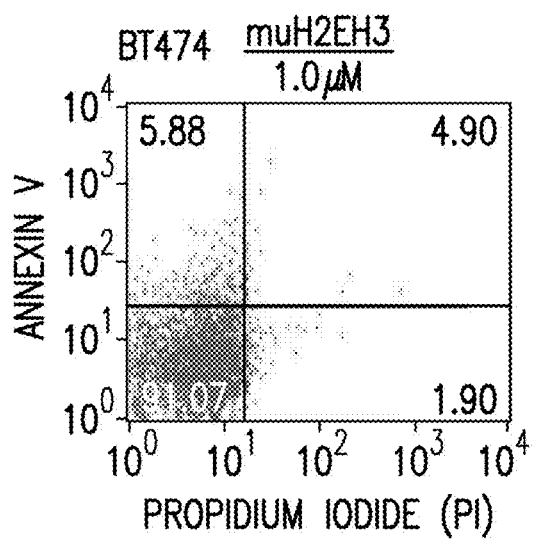
Figure 12N:
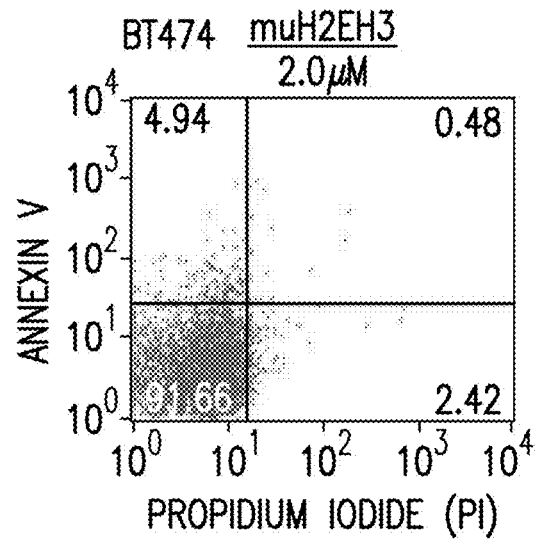
Figure 12O:
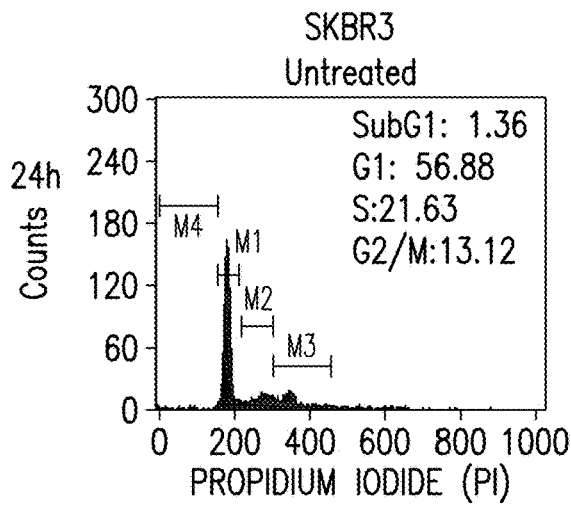
Figure 12P:
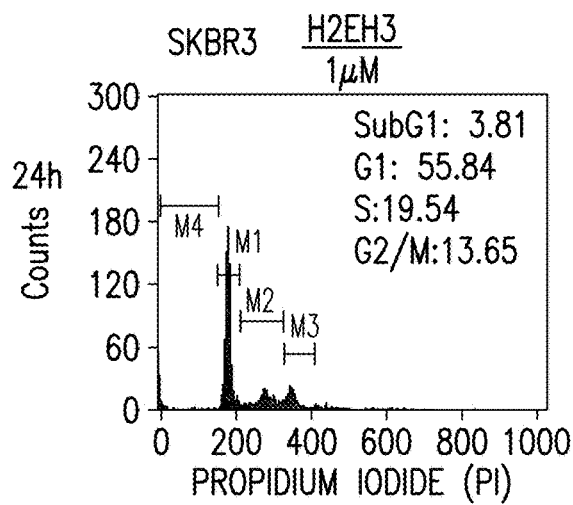
Figure 12Q:
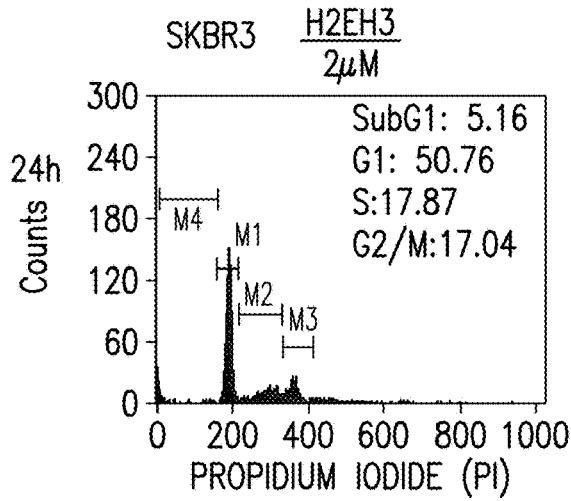
Figure 12R:
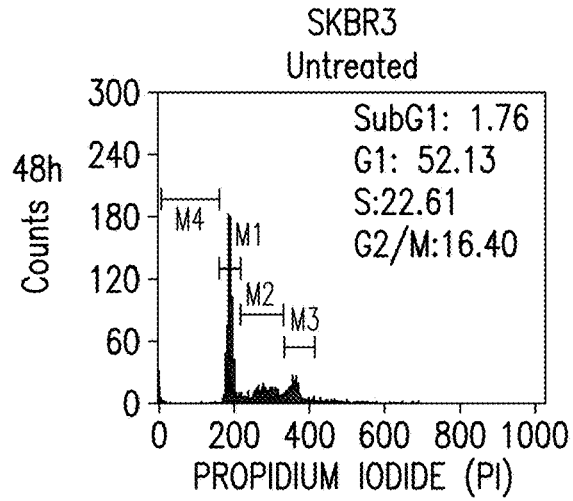
Figure 12S:
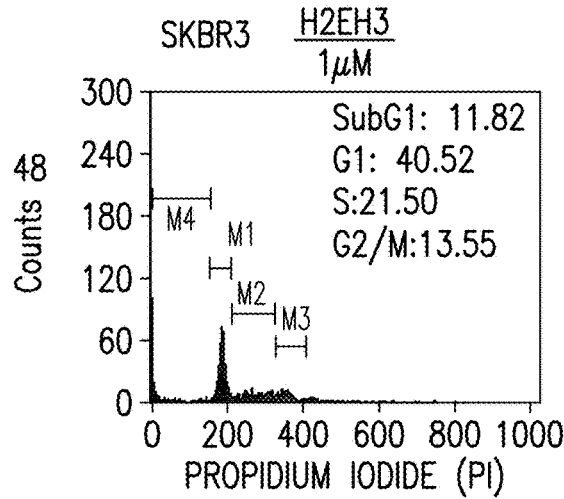
Figure 12T:
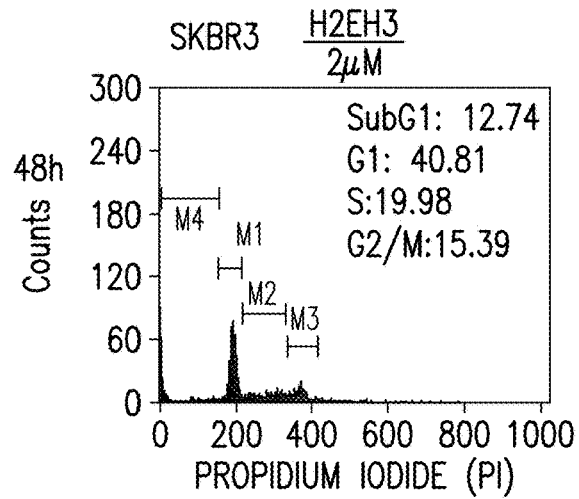
Figure 12U:
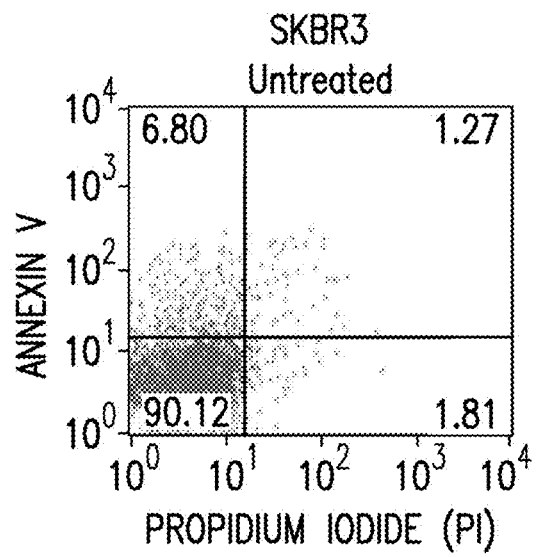
Figure 12V:
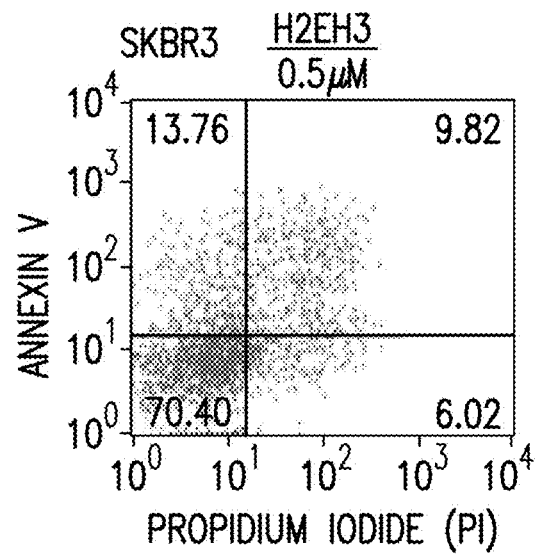
Figure 12W:
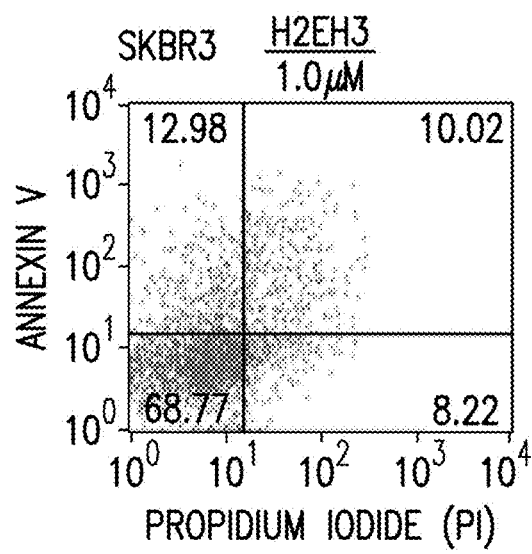
Figure 12X:
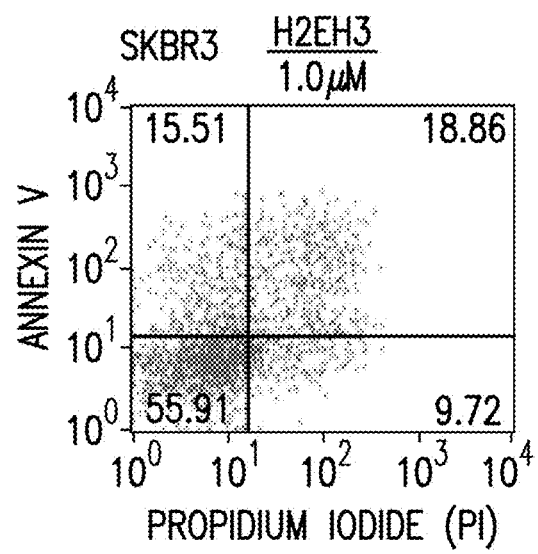
Figure 12Y:
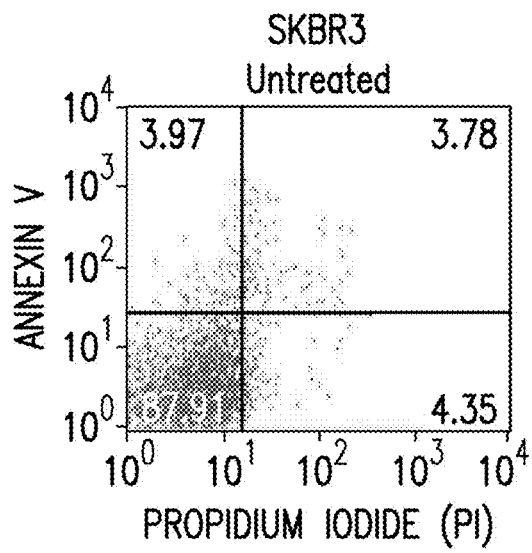
Figure 12Z:
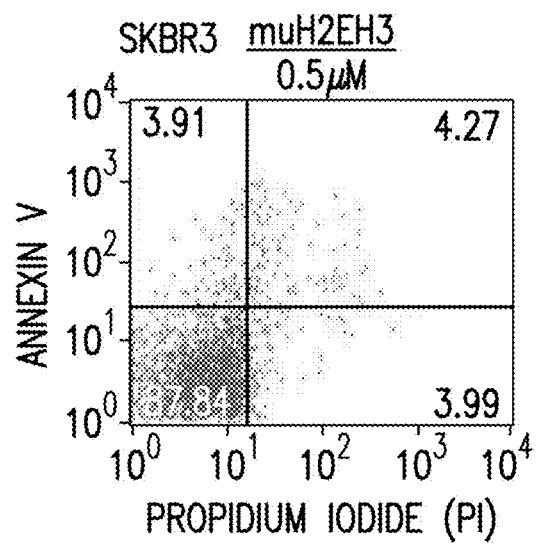
Figure 12A:
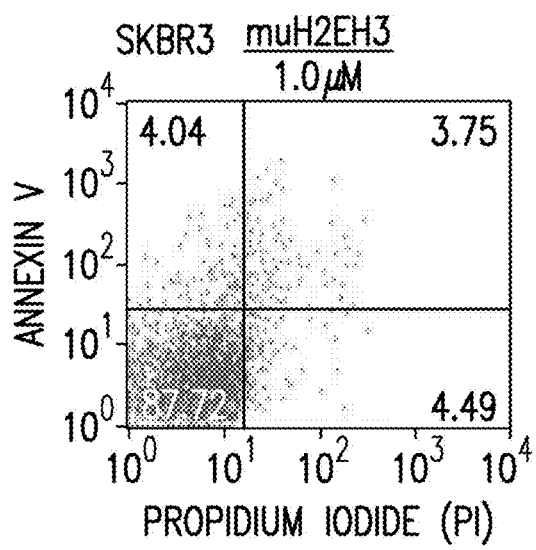
Figure 12B:
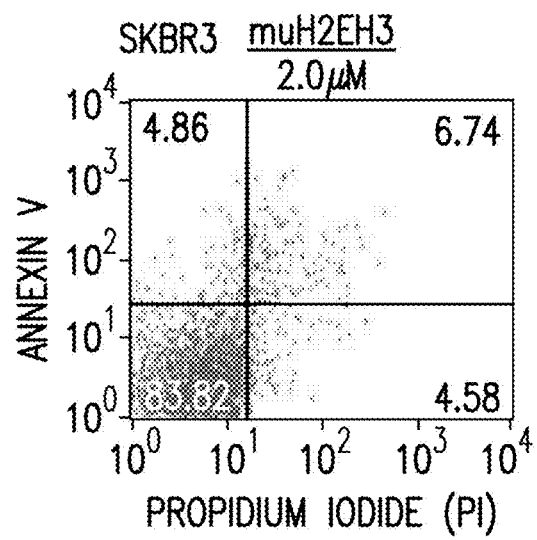

To further assess induction of apoptosis by H2EH3, SKBR3 cells and BT474 cells were treated with H2EH3 for 72 h and stained with Annexin V/PI (Propidium Iodide) for flow cytometry analyses. As shown in FIG. 12G-12N, for BT474 cells, early apoptosis (Annexin V+/PI−) increased from untreated 4.43% to 11.37%, 23% and 20.91% treated with H2EH3 at 0.5 µM, 1.0 µM and 2.0 µM, respectively; late stage (Annexin V+/PI+) increased from untreated 1.23% to 1.87%, 3.76% and 5.06% treated with H2EH3 at 0.5 µM, 1.0 µM and 2.0 µM, respectively, whereas, mH2EH3 at 0.5-2.0 µM range has <6% early apoptosis and <5% late apoptosis. In SKBR3 cells, the most significant change occurred on late apoptosis stage. Late apoptosis of SKBR3 cells increased from untreated 1.27% to 9.82%, 10.02% and 18.86% when treated with H2EH3 at 0.5 µM, 1 µM and 2 µM, respectively, whereas muH2EH3 at 0.5-2.0 µM range has <7% late apoptosis (FIG. 12U-12BB). These results from the analyses of cell cycle progression and apoptosis suggest that H2EH3 induces cell death through cell cycle arrest and apoptosis on HER2+HER3+ cell lines.

Example 16: H2EH3 Internalization

Materials and Methods

Confocal Microscopy

BT474 cells were treated with Cy5-H2EH3 and control Cy5-muH2EH3 aptamer. Confocal microscopy with z-stack was performed to visualize the subcellular locations of H2EH3. Nuclei were stained with DAPI and endosome/lysosomes were revealed by Lysotracker.

Results

Figure 13A:
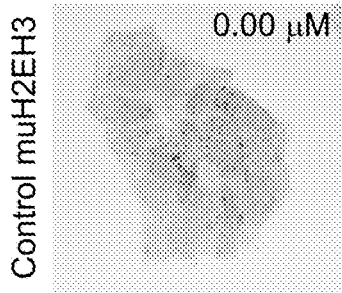
FIG. 13A-13X are a panel of immunofluorescent micrographs showing H2EH3 internalization by Z-stack confocal microscopy. Cy5-labeled H2EH2 or CY-5 labeled H2EH3 was added into BT474 cells for 12 h at 37° C. Lysotracker Green and DAPI were added into cells at the same time as the chimeras. LysoTracker Green was used to show lysosomes and endosomes. DAPI was used to display nucleus. Confocal laser scanning microscopy with z-stack was performed to show cell binding and internalization.
Figure 13B:
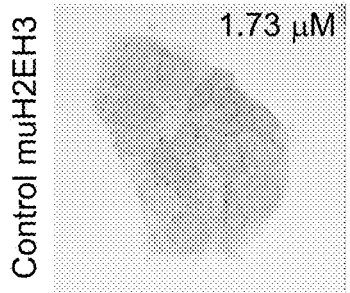
FIGS. 13Y-13Z are Western blots showing total HER family receptors and apoptosis-associated molecules in BT474 cells.
Figure 13C:
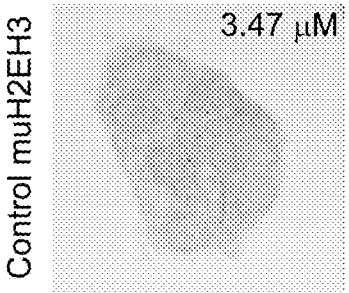
Figure 13D:
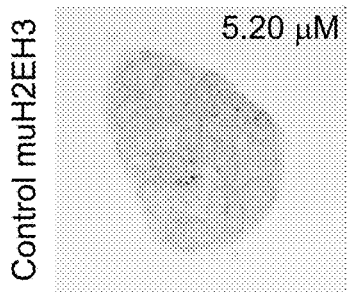
Figure 13E:
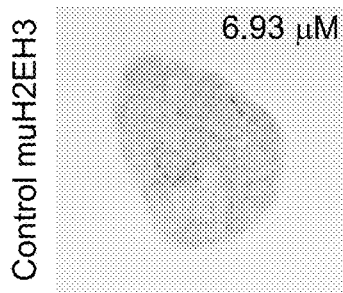
Figure 13F:
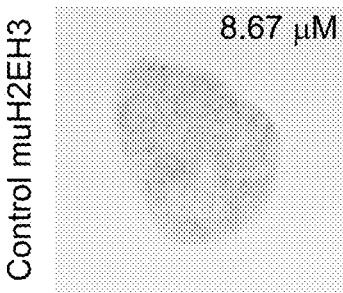
Figure 13G:
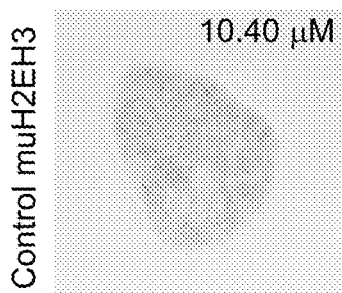
Figure 13H:
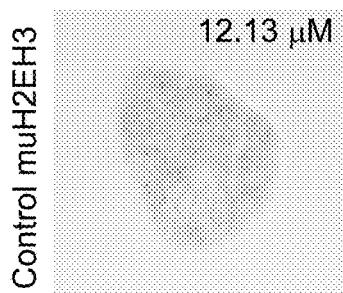
Figure 13I:
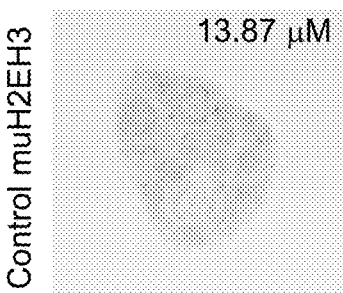
Figure 13J:
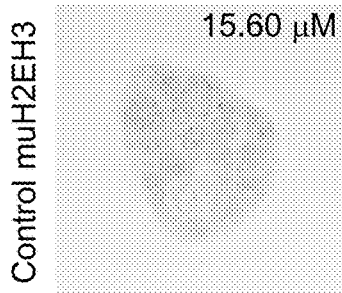
Figure 13K:
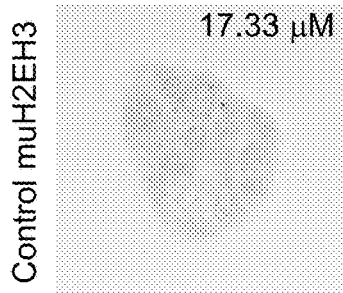
Figure 13L:
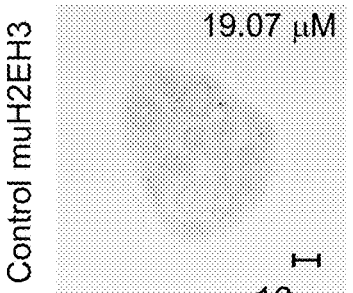
Figure 13M:
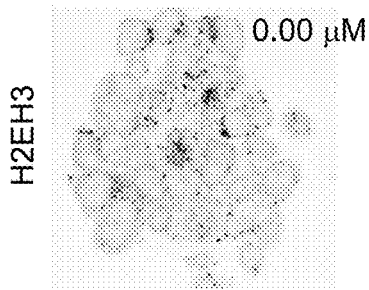
Figure 13N:
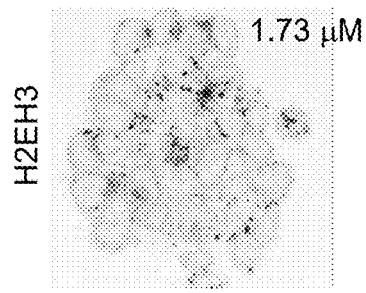
Figure 13O:
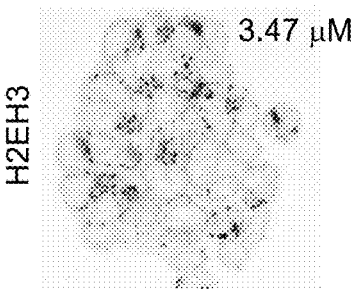
Figure 13P:
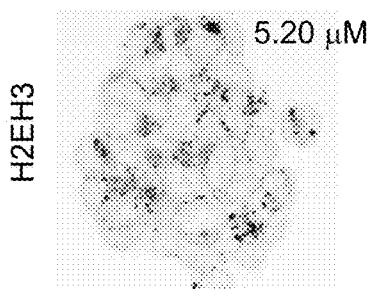
Figure 13Q:
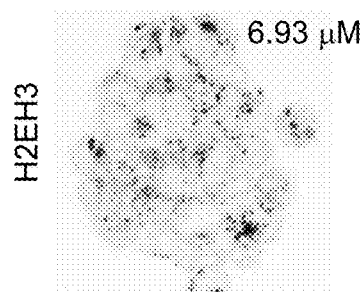
Figure 13R:
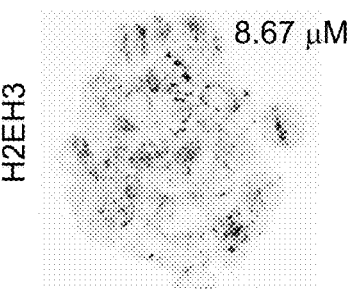
Figure 13S:
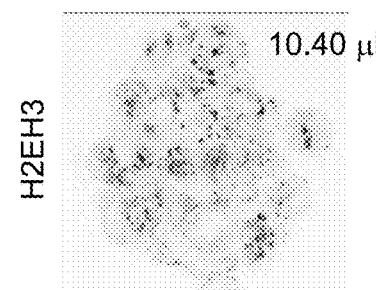
Figure 13T:
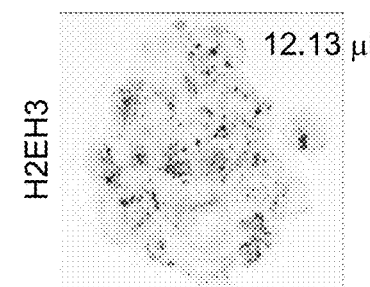
Figure 13U:
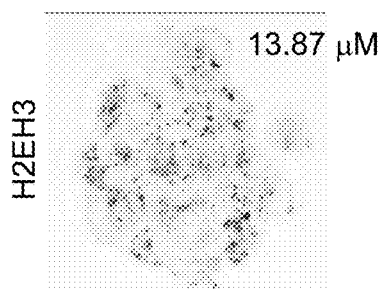
Figure 13V:
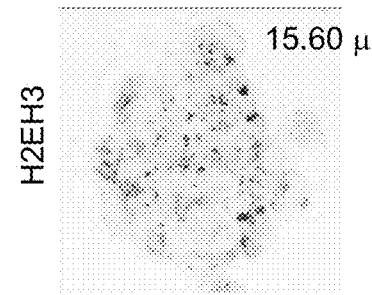
Figure 13W:
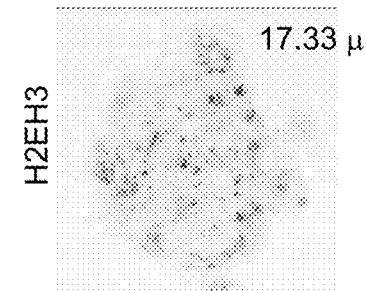
Figure 13X:
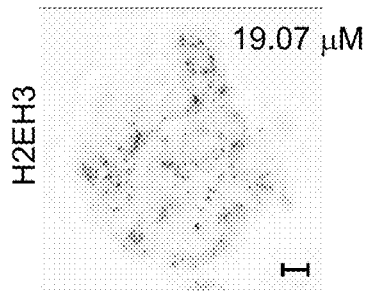

Because EGFR siRNA was inserted between HER2 and HER3 aptamers, EGFR gene knockdown was expected. It was hypothesized that H2EH3 binding to cell receptors of HER2 and HER3 will cross link two receptors and result in ligand-receptor complex internalization. The internalized H2EH3 may lead to EGFR silencing. First, the internalization of H2EH3 was validated, which is the prerequisite of siRNA silencing. As shown in FIGS. 13A-13X, after 12-h incubation, H2EH3 entered the cells and presented in the cytoplasm, and some of H2EH2 escaped from endosome/lysosomes by showing red fluorescence, while some H2EH3 entrapped in endosomes showed yellow signal. The result showed that HER2/HER3 dimerization can lead chimera internalization.

Example 17: H2EH3 Chimera-Mediated Reduction in EGFR, HER2, and HER3 Expression and Upregulation of Cleaved-Caspase 3 and p21

Materials and Methods

Western blot. Cells were lysed in lysis buffer (M-PER Mammalian Protein Extraction Reagent, Thermo Fisher Scientific) containing 1×Protease Inhibitor Cocktails (Sigma Aldrich). The cell lysates were centrifuged at 12,000 g for 10 min at 4° C. The supernatant was collected and the protein concentration was determined with Bio-Rad Protein Assay (Bio-Rad, Hercules, Calif.). Equal amount of proteins was mixed with 4×Laemmli sample buffer containing 5% β-mercaptoethanol and heated at 95° C. for 10 min. Denatured samples was separated on 8%-10% SDS-PAGE and transferred to PVDF membrane. The membranes were blocked with 5% non-fat milk overnight at 4° C., and then incubated with primary antibodies overnight at 4° C., followed by incubation with horseradish peroxidase-conjugated secondary antibodies for 2 h at room temperature. After ECL Western Blotting Substrate (Pierce) was added onto membrane, the signals were captured by the exposure to X-ray film.

Results

Figure 13Y:
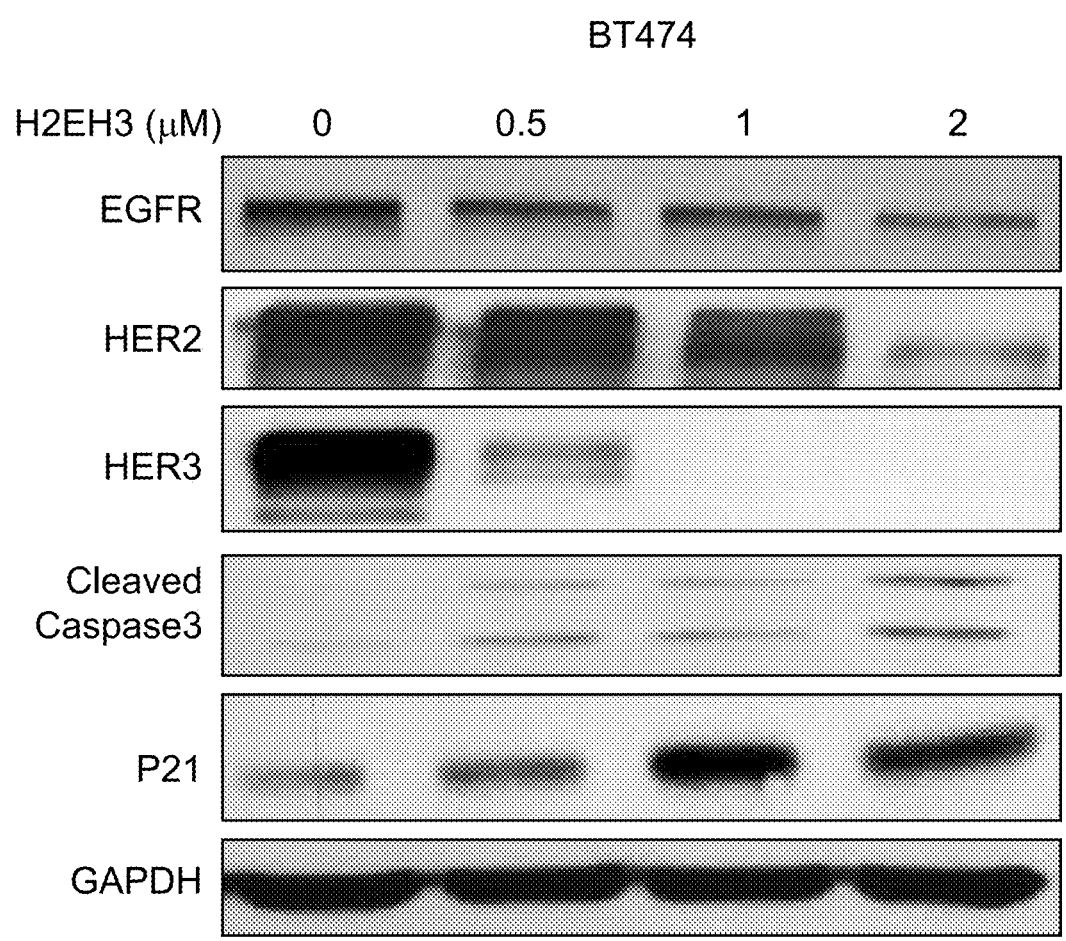
Figure 13Z:
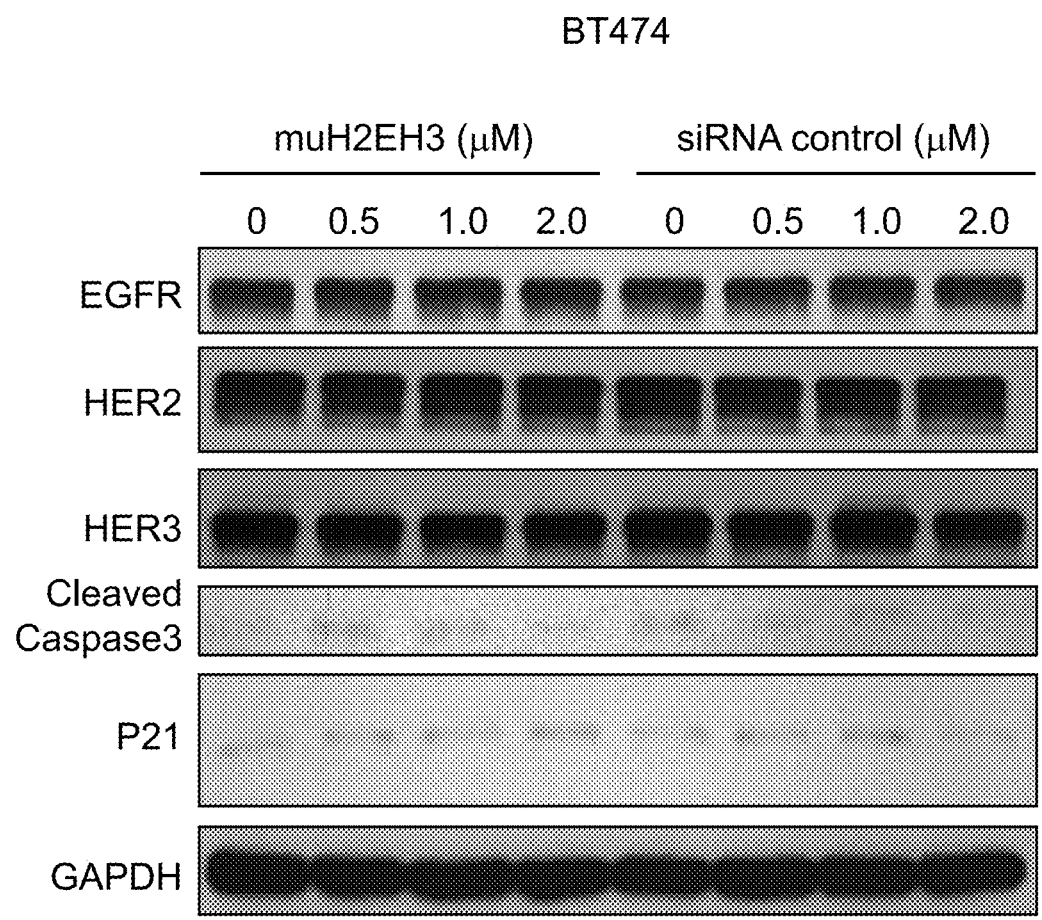
Figure 13A:
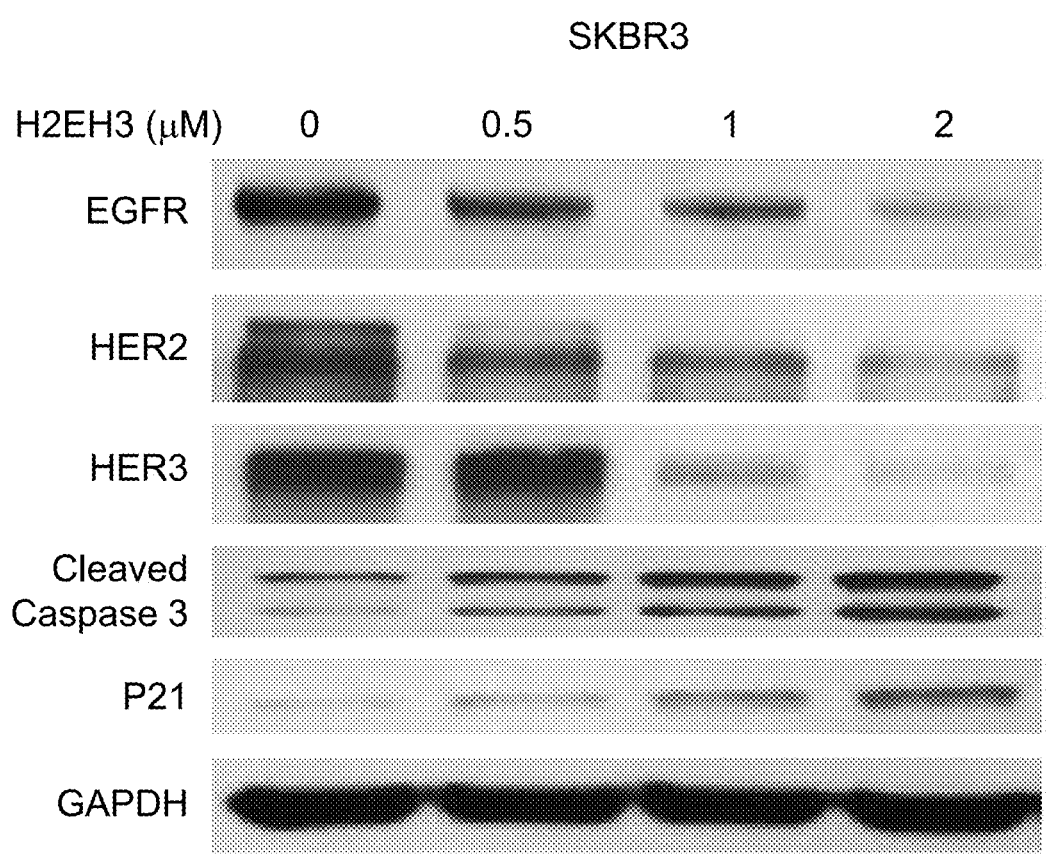
Figure 13B:
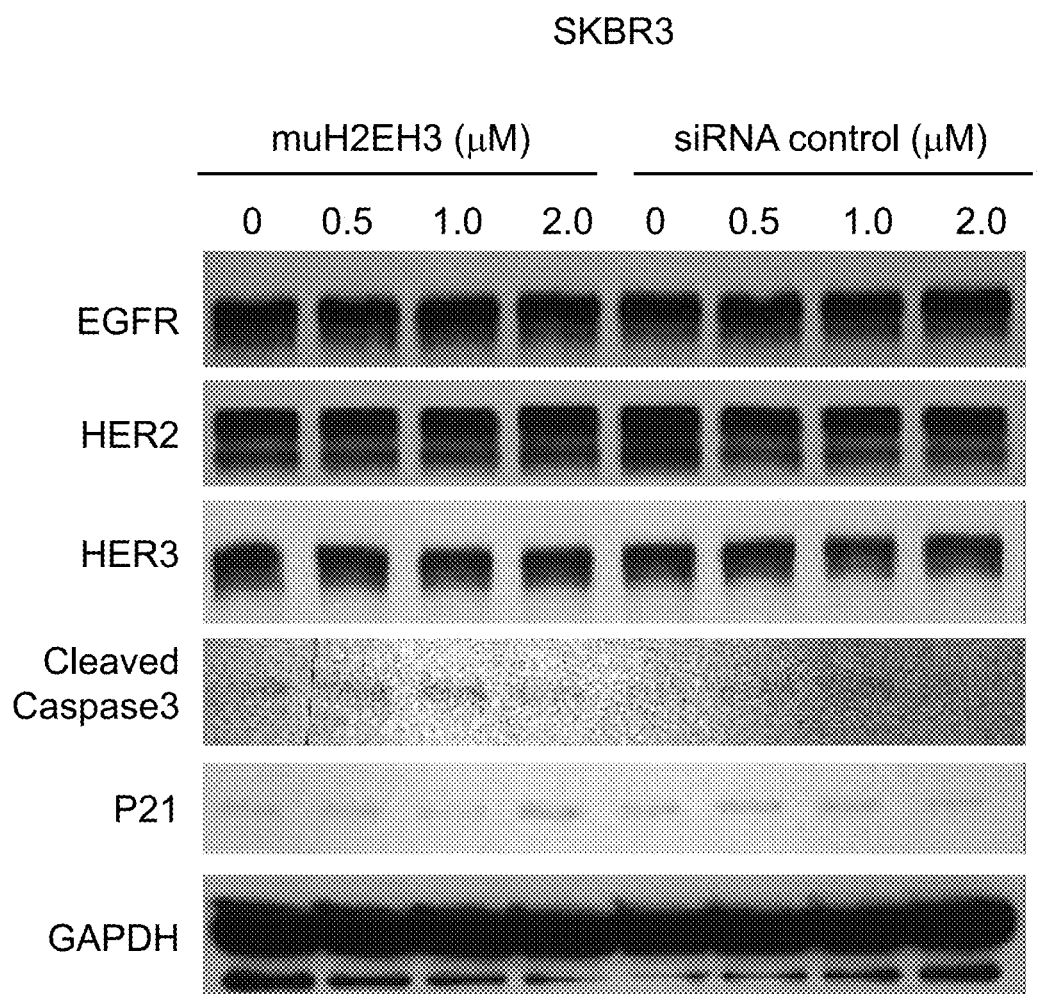

EGFR siRNA triggered gene silencing. EGFR expression was evaluated with Western blot. As shown in FIG. 13Y, after treatment with H2EH3 for 72 h, EGFR expression levels in both BT474 and SKBR3 cells were significantly reduced in a dose-dependent manner but not treated with muH2EH3 or scrambled siRNA control (FIG. 13Y-13BB).

The effect of H2EH3 on protein levels of HER2 and HER3 was examined next. SKBR3 and BT474 cells were treated with the varying concentrations of H2EH3 for 72 h, HER2 and HER3 levels were quantified by Western blot. As shown in FIG. 13Y-13BB, H2EH3 treatment, but not muH2EH3 or scrambled siRNA control, resulted in pronounced reduction of protein levels of HER2 and HER3 in SKBR3 and BT474 cells. That indicates H2EH3 has led ligand-induced HER2 and HER3 receptor internalization and degradation, which results in the reduction of protein levels of HER2 and HER3. From previous studies, targeting a single HER family member often results in increased levels of other HER receptors which will compensate the activity of inhibited HER member and counteract the treatment efficacy (Wheeler, et al., *Oncogene*, 27: 3944-3956 (2008); Dua, et al., *Breast Cancer Res Treat*, 122: 685-697 (2010)). In contrast, H2EH3 is able to significantly reduce the expression of all three receptors, thereby effectively block the compensatory network of HER members.

Next, the effect of H2EH3 on downstream apoptotic signaling was examined. Upon treatment with H2EH3, BT474 and SKBR3 cells were probed for the expression of p21 and Cleaved Caspase-3 (CC3) by Western blot. CC3 is regarded as a signature marker of apoptosis, and p21 upregulation is closely related to cell cycle arrest and apoptosis. As shown in FIG. 13Y-13BB, p21 and CC3 were significantly upregulated by H2EH3 in a dose-dependent manner in SKBR3 and BT474 cells. The results indicate that H2EH3 induces cell growth inhibition through activating the signaling pathways associated with cell cycle arrest and apoptosis.

Example 18: H2EH3 Binding Specificity

Materials and Methods

Knockdown of HER2 and/or HER3. BT474 cells were plated in 6-well plates at a density of $5 \times 10^5$ cells/well for 24 h. HER2 siRNA and/or HER3 siRNA or control siRNA were transfected into cells using Lipofectamine RNAi MAX (Life Technologies) according to the manufacturer's instruction. Cells were harvested 72 h post-transfection and Western blot was performed to confirm gene knockdown. HER2 and/or HER3 silenced cells were subjected to aptamer binding assay by BD flow cytometry.

Results

Figure 14A:
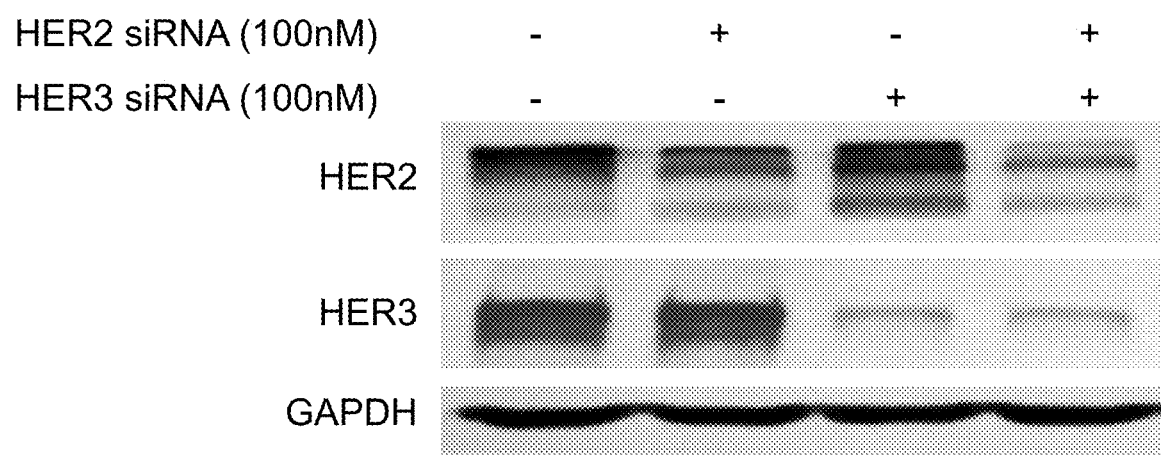
FIG. 14A is a Western blot showing HER2 and/or HER 3 gene knockdown.
Figure 14B:
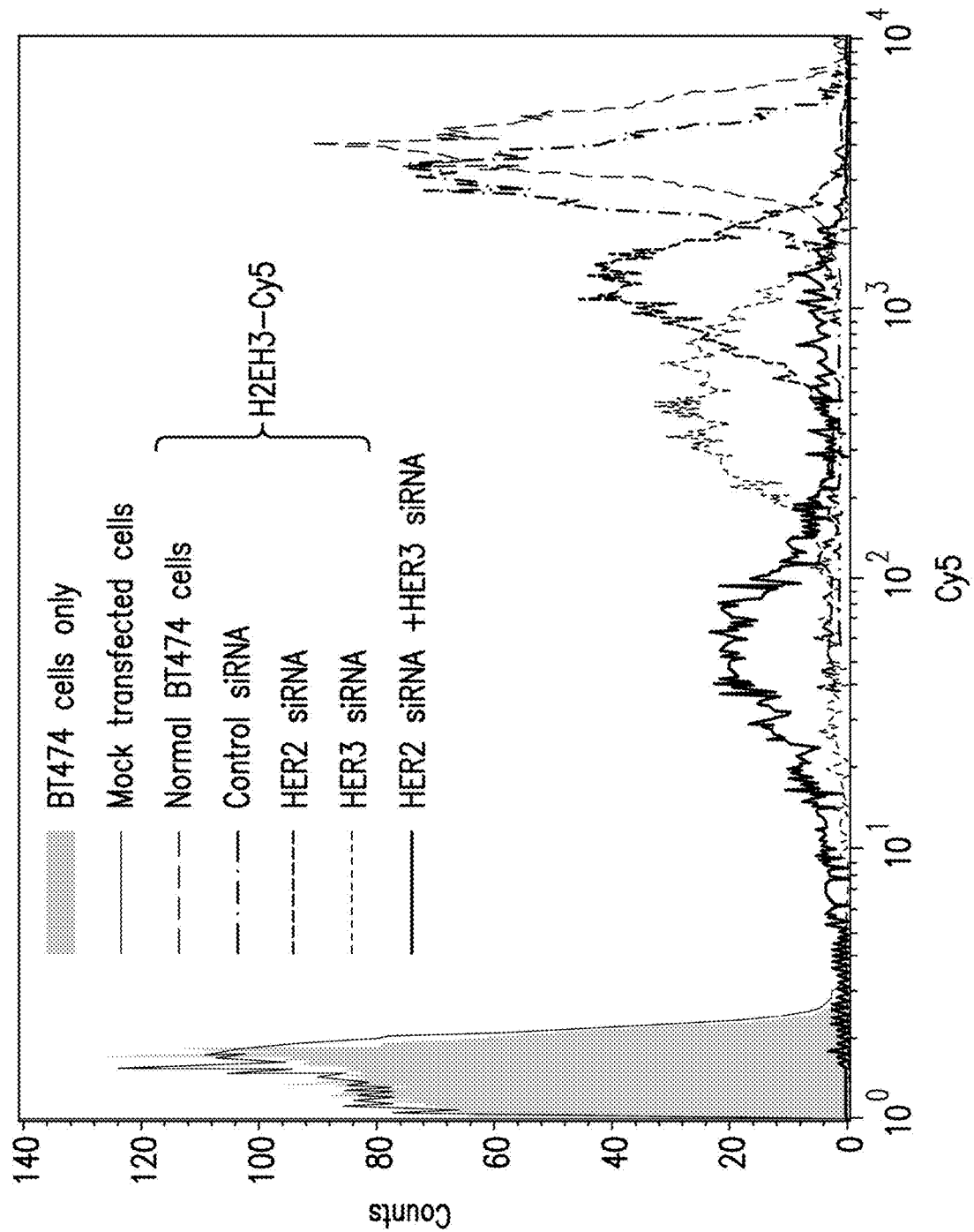
FIG. 14B shows flow cytometric analysis of cell binding of H2EH3 upon HER2 or HER3 knockdown in BT474 cells.

To investigate whether H2EH3 indeed binds to HER2 and HER3 receptors, siRNAs were used to silence each receptor to assess binding specificity. HER2 and/or HER3 siRNAs were transfected into BT474 cells via lipofectamine, then binding pattern was detected after receptor knockdown. HER2 and/or HER3 knockdown was confirmed with Western blot (FIG. 14A). After treatment with 100 nM of HER2 siRNA and/or HER3 siRNA, the protein levels of HER2 and HER3 are significantly reduced. Then, H2EH3 binding was analyzed for HER2 and/or HER3 silenced BT474 cells compared with untreated BT474. BT474 cells (untreated, or HER2/HER3 silenced) were first fixed with 1% paraformaldehyde-PBS and then incubated with Cy5 labeled H2EH3 or controls. As shown in FIG. 14B, untreated BT474 cells have a strong fluorescence peak and high fluorescence intensity. Upon knockdown of HER2 or HER3, the fluorescence peak of single positive HER3+ cells or HER2+ cells has shifted to the left (lower intensity areas) suggesting reduced binding following HER2 or HER3 knockdown. Upon knockdown of both HER2 and HER3, most cells died. However when the remaining cells were analyzed, the fluorescence intensity of double negative HER2−HER3− BT474 cells showed a significant decrease compared with normal BT474. These results indicate that H2EH3 indeed possesses specificity toward HER2 and HER3 receptors.

Example 19: H2EH3 Possesses High Tumor Targeting Capability In Vivo

Materials and Methods:

Bio-distribution assay. To evaluate the bio-distribution properties of H2EH3, tumor bearing mice were intravenously administrated with Cy5-labeled H2EH3 (20 nmoles, 200 μl) or equal mole amount of Cy5-labeled MG aptamer. The whole-body images were obtained at 0.5 h and 6 h using Xenogen IVIS100 imaging system by setting wavelength at excitation 640 nm and emission 710 nm. After 6-h injection of Cy5-labeled aptamers, mice were euthanized with CO2 following whole-body imaging, and organs (heart, lung, liver, spleen, kidney, muscle, brain, stomach, and intestine) were removed. The ex vivo imaging of Cy5 signal were performed using Xenogen IVIS100.

In vivo xenograft treatment study. 4 to 5-week-old female athymic nu/nu mice were injected with tumor cells (BT474 or MDA-MB-231) ($2 \times 10^6$) mixed with Matrigel (v/v 1:1) (Corning, N.Y.) subcutaneously at the left flank of mice, or orthotopically at the mammary fat pads of mice. Following the establishment of tumors (100 mm$^3$), mice were randomly divided into three groups in subcutaneous xenografts, H2EH3 (8 nmoles, 200 μl), or mixture of HER2 aptamer &EGFR siRNA & HER3 aptamer (each 8 nmoles, total 200 μl), or PBS (200 μl) was intra-tumorally injected to mice at every other day for 5 weeks. In the orthotopic xenografts, upon tumor reaching 50 mm$^3$, mice were administrated with H2EH3 (8 nmoles, 200 μl) or PBS every three days through tail-vein intravenous injection for 4 weeks. Tumor sizes and body weights were measured twice a week. The animals were euthanized two days after the last treatment. The tumors and organs (liver, spleen, kidney, brain, heart, muscle, blood and intestine) were removed and fixed in 10% formalin buffer. The sections of tissues were analyzed by immunohistochemistry.

Figure 14C:
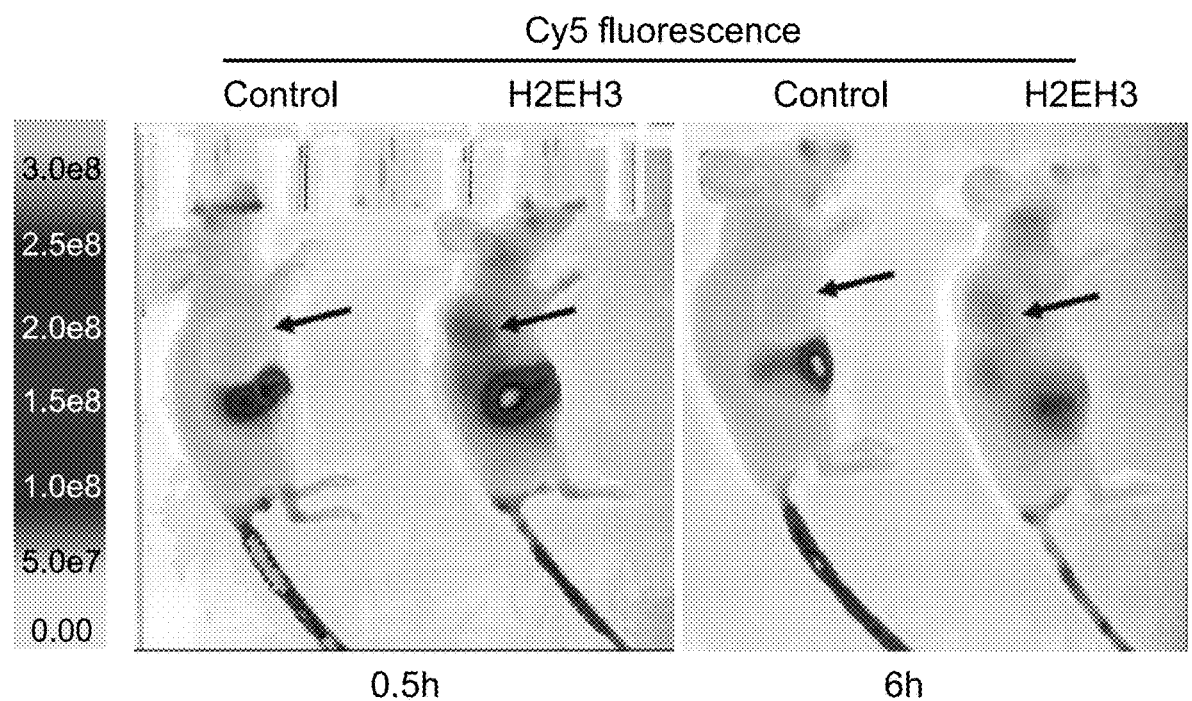
FIGS. 14C-14D are are representative images of time-course whole-body imaging of the binding profile of H2EH3 in tumor-bearing mice intravenously injected with Cy5-H2EH3 or non-targeting control aptamer.
Figure 14D:
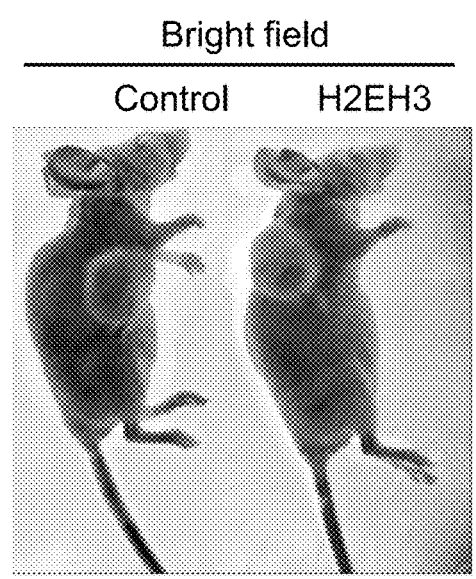
Figure 14E:
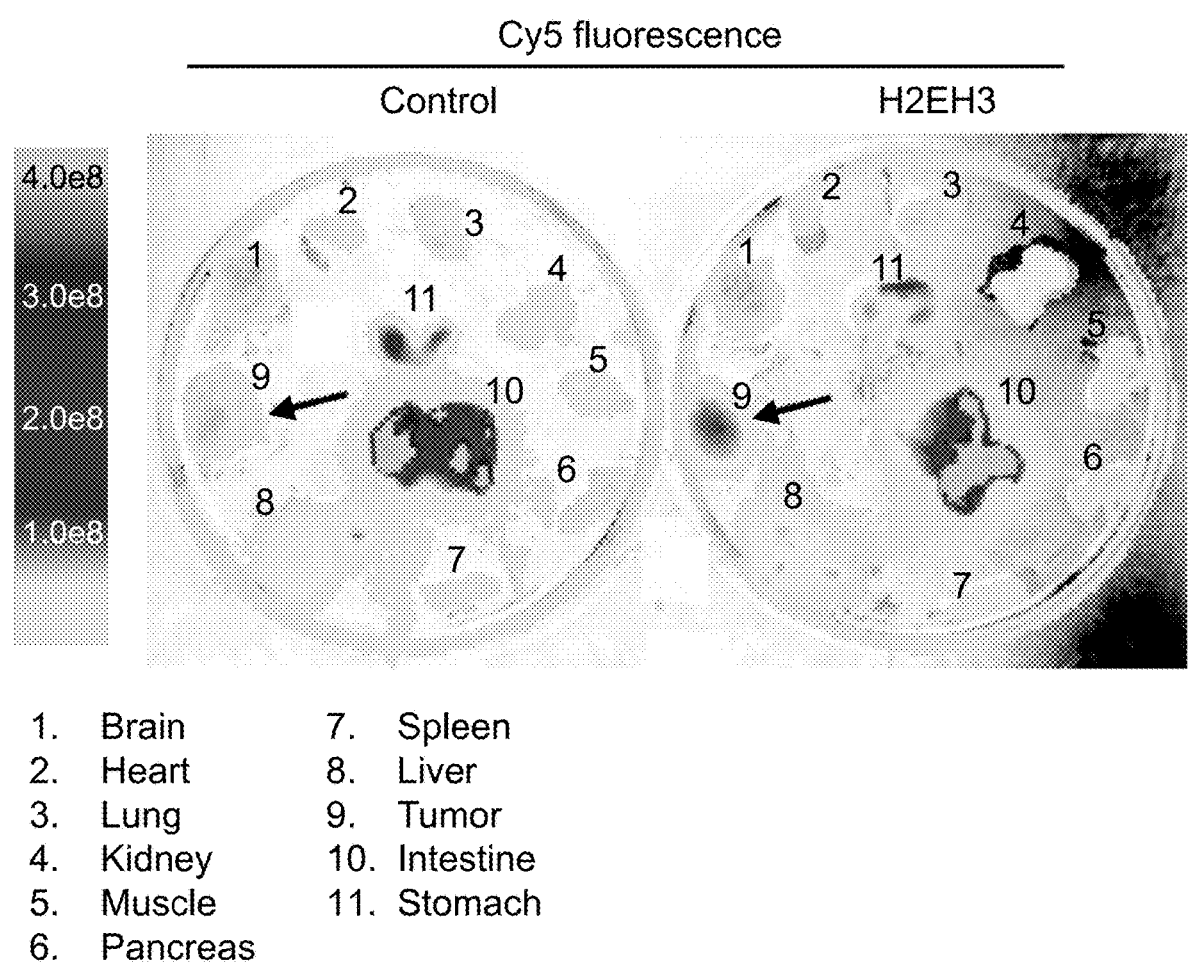
FIG. 14E is a representative image of ex vivo organ imaging in tumor-bearing mice intravenously injected with Cy5-H2EH3 or non-targeting control aptamer. 1. Brain; 2. Heart; 3. Lung; 4. Kidney; 5. Muscle; 6. Pancreas; 7. Spleen; 8. Liver; 9. Tumor; 10. Intestine; 11. Stomach.

Results:

To explore tumor targeting capability and bio-distribution in vivo, BT474 tumor bearing mice were tail-vein injected with Cy5-H2EH3 or non-targeting control aptamer. Thirty minutes after injection with control aptamer or H2EH3, the tumors in H2EH3 treated mice but not tumors in non-targeting control aptamer treated mice show high fluorescence intensity that is clearly delineated from the surrounding background tissues with Xenogen IVIS100 imaging system (FIG. 14C-14D). The fluorescence signals can be detectable for 6 h. After whole body imaging, organs were removed and ex-vivo imaging was performed. As shown in FIG. 14E, the Cy5 florescence in H2EH3 treated tumors, but not control aptamer treated tumors, was detectable. It is not surprising that strong fluorescence are shown in intestines and stomach since that locations are the places for clearance of chimeras from bodies. Noteworthy, Cy5 fluorescence signals are not detectable in organs including brain, spleen, liver, heart, lung, kidney, muscle and pancreas. These results suggest that H2EH3 can bind to tumors in vivo with high specificity.

Example 20: H2EH3 Decreases Tumor Growth in Breast Cancer Xenografts

Materials and Methods

In vivo xenograft treatment study. 4 to 5-week-old female athymic nu/nu mice were injected with tumor cells (BT474 or MDA-MB-231) ($2 \times 10^6$) mixed with Matrigel (v/v 1:1) (Corning, N.Y.) subcutaneously at the left flank of mice, or orthotopically at the mammary fat pads of mice. Following the establishment of tumors (100 mm$^3$), mice were randomly divided into three groups in subcutaneous xenografts, H2EH3 (8 nmoles, 200 μl), or mixture of HER2 aptamer, EGFR siRNA, and HER3 aptamer (each 8 nmoles, total 200 μl), or PBS (200 μl) was intra-tumorally injected to mice at every other day for 5 weeks. In the orthotopic xenografts, upon tumor reaching 50 mm$^3$, mice were administrated with H2EH3 (8 nmoles, 200 μl) or PBS every three days through tail-vein intravenous injection for 4 weeks. Tumor sizes and body weights were measured twice a week. The animals were euthanized two days after the last treatment. The tumors and organs (liver, spleen, kidney, brain, heart, muscle, blood and intestine) were removed and fixed in 10% formalin buffer. The sections of tissues were analyzed by immunohistochemistry.

Results

Figure 15A:
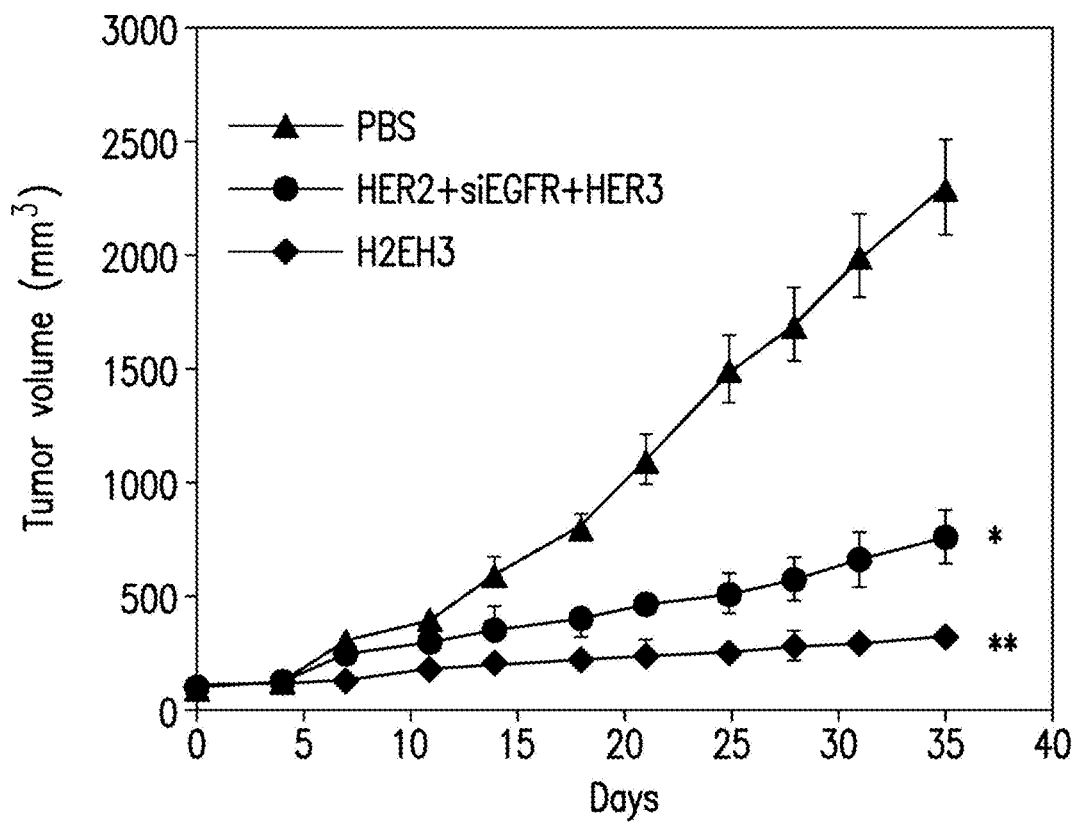
FIG. 15A is a line graph showing tumor volume (mm³) over time (days) in mice with subcutaneous tumors treated with PBS (▲), a mixture of HER2 aptamer and HER3 aptamer (●), or H2EH3 (◆).
Figure 15B:
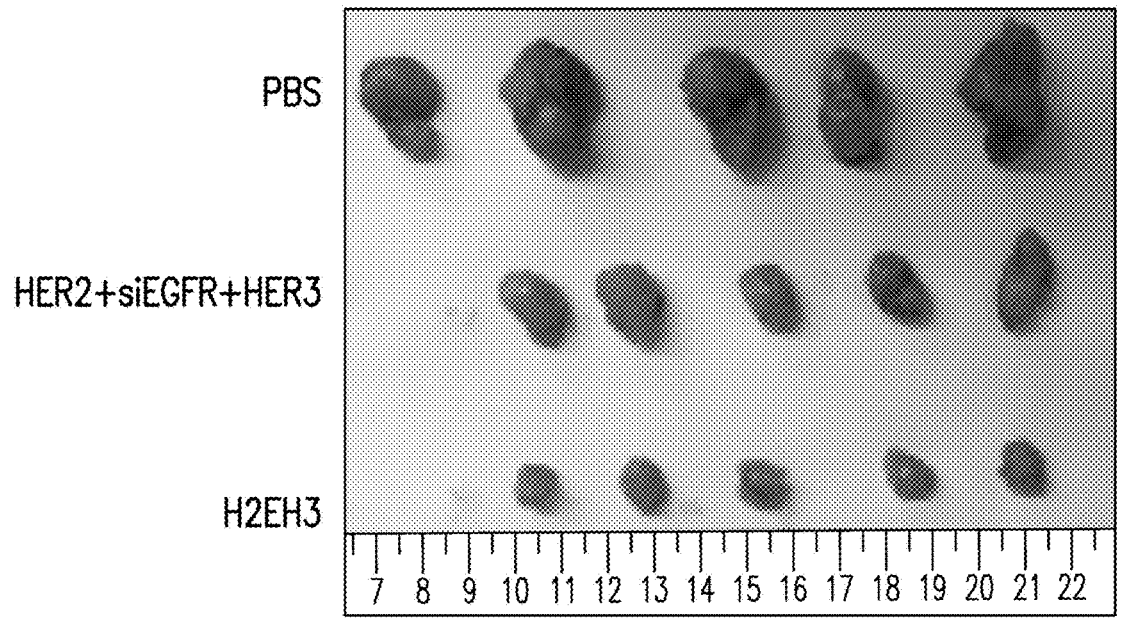
FIG. 15B shows dissected tumors after treatment.
Figure 15C:
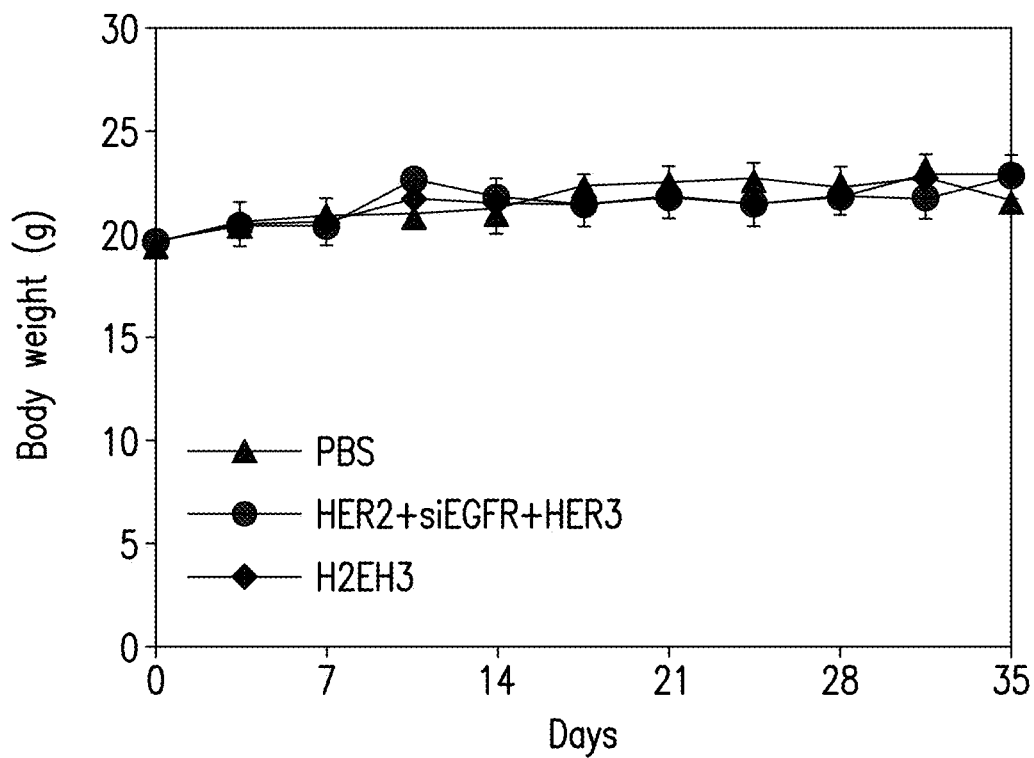
FIG. 15C is a line graph representing body weight (g) over time (days) for tumor-bearing mice treated with PBS (▲), a mixture of HER2 aptamer and HER3 aptamer (●), or H2EH3 (◆).
Figure 15D:
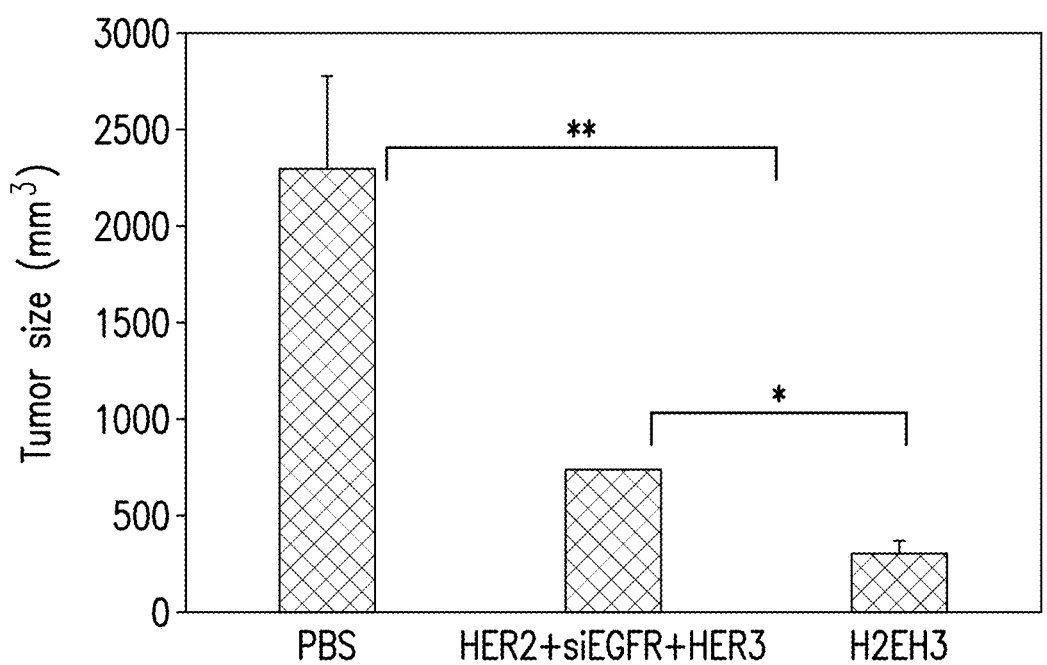
FIG. 15D is a bar graph showing the tumor size (mm³) of subcutaneous tumors treated with PBS, a mixture of HER2 aptamer and HER3 aptamer, or H2EH3.

To investigate whether the in vitro anti-proliferative effect of H2EH3 could translate into in vivo efficacy, H2EH3 treatment was tested in subcutaneous and orthotopic breast cancer xenografts. BT474 cells were subcutaneously injected into 5 to 6 week-old female athymic nu/nu mice at the left flank of mice. Upon tumor reaching 100 mm$^3$, mice were treated with PBS, mixture (HER2 aptamer, HER3 aptamer, and EGFR siRNA) (8 nmoles of each component) or H2EH3 (8 nmoles) by intra-tumor injection every other day for 5 weeks. As shown in FIG. 15A-15D, H2EH3 treatment showed pronounced tumor growth inhibition and is superior to the mixture of HER2 aptamer, HER3 aptamer, and EGFR siRNA. Tumors in H2EH3 treated mice have 6-7 fold reduction in sizes compared with PBS treated controls, and about 1.5 fold reduction compared with those treated with the mixture of HER2 aptamer, HER3 aptamer, and EGFR siRNA (FIG. 15D).

Figure 15E:
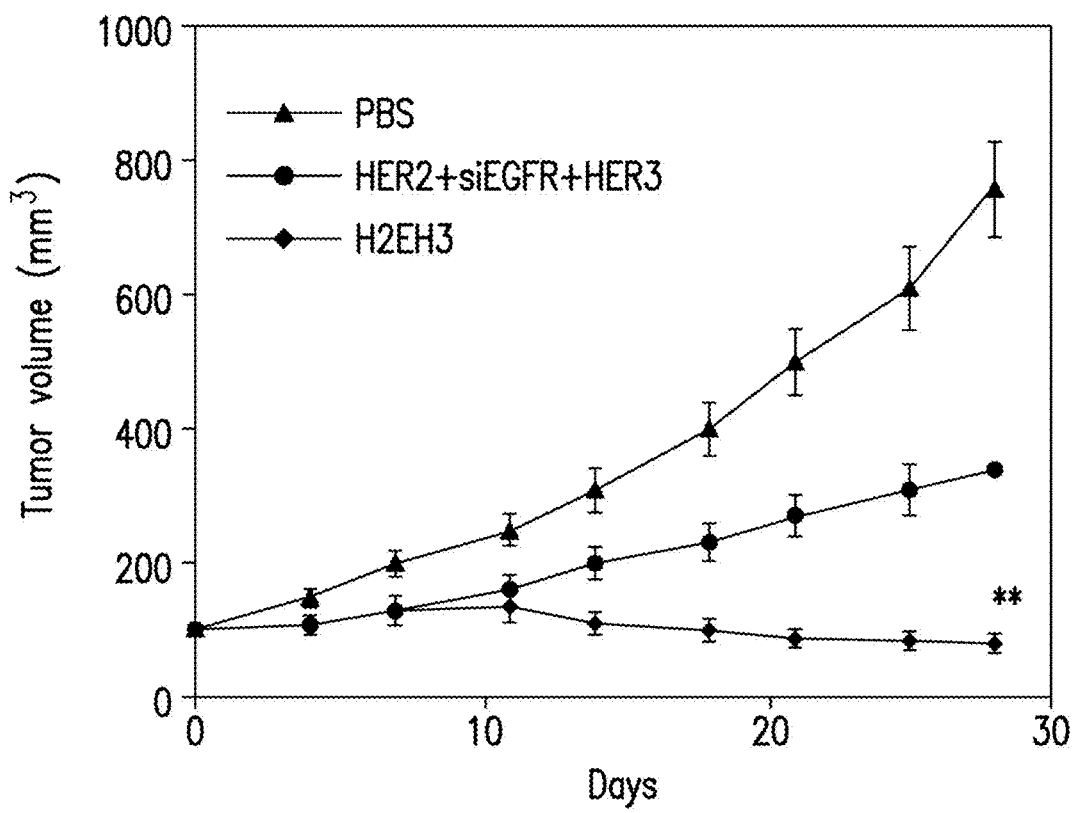
FIG. 15E is a line graph showing tumor volume (mm³) over time (days) in mice with orthotopic tumors treated with PBS (▲), a mixture of HER2 aptamer and HER3 aptamer (●), or H2EH3 (◆).
Figure 15F:
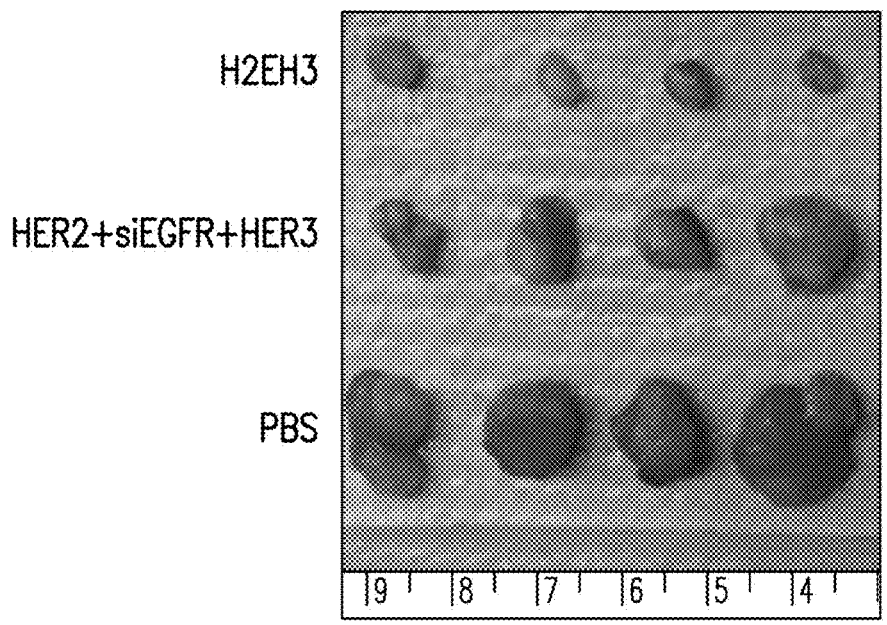
FIG. 15F shows dissected tumors after treatment through intravenous injection.
Figure 15G:
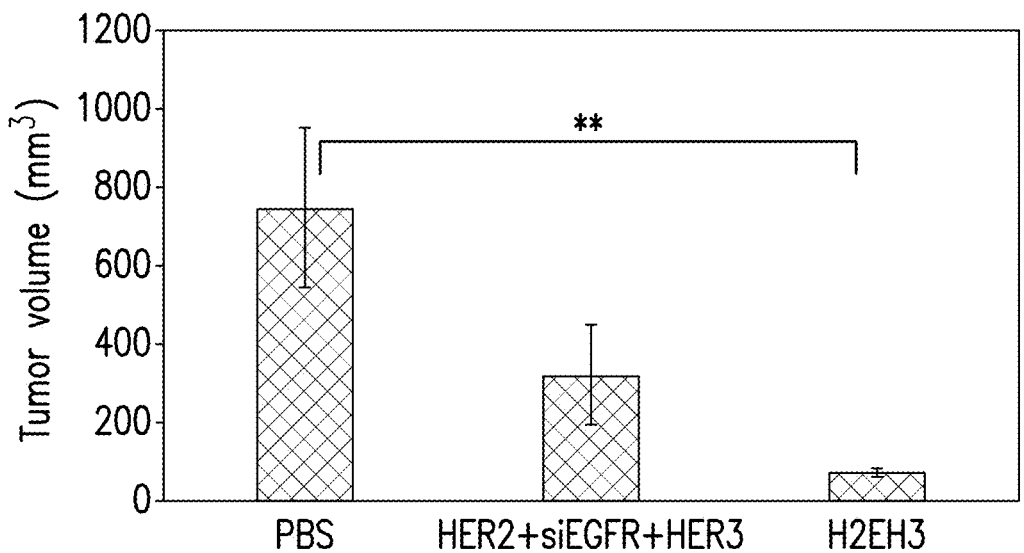
FIG. 15G shows a bar graph quantitation of orthotopic tumor volume (mm³) in mice treated with intravenous injection of PBS, a mixture of HER2 aptamer and HER3 aptamer, or H2EH3.

Next, mammary orthotopic xenografts were set up by injection of BT474 cells in mammary fat pads. Tumor (50 mm$^3$) bearing mice were intravenously (via tail-vein) treated with H2EH3 (8 nmoles), mixture (HER2 aptamer, HER3 aptamer, and EGFR siRNA) or PBS every three days for 4 weeks. As shown in FIG. 15E-15G, H2EH3 treatment achieved 7-8 fold reduction in tumor sizes compared to PBS control group, and 3-4 fold reduction compared with those treated with the mixture of three components. Due to the limitation in available injection times through tail vein in this experiment, administration was continued for 4-weeks. These results show H2EH3 is able to effectively inhibit HER2 expressing breast cancer growth through both intra-tumoral and intravenous injection. As a tumor control, MDA-MB-231 cells (HER2 and HER3 negative) were used to set up mammary orthotopic xenografts. Tumor bearing mice were treated with H2EH3 and controls through IV injection. As shown in the FIG. 16A-16D, there are no significant treatment effects in the groups treated with H2EH3 or the mixture of three components compared with PBS control group. The results proved the targeting capability of H2EH3 in vivo.

Example 21: H2EH3 Downregulation of HER2 and HER3 and Induction of Apoptosis In Vivo Materials and Methods Histology assay. Tumors and organs (spleen, lung, kidney, intestine, heart, liver and muscle) were collected from xenografts, and fixed with 4% paraformaldehyde. Sections (6 μm) were cut and mounted on the slides, and deparaffinized in xylene and ethyl alcohol. For immunohistochemistry assay, sections were incubated in 3% normal goat serum for 2 h and incubated with primary antibodies: caspase-3 (1:200), HER2 (1:800), HER3 (1:250), p21 (1:50), and EGFR (1:50). After washing, the sections were incubated with biotinylated secondary antibody (1:200) (VECTOR, Burlingame, Calif.) for 1 h. Following washing, the sections were incubated with VECTASTAIN ABC reagents for 30 min. The images were captured with Nuance fluorescence microscope with bright field imaging system.

Results

To determine the target specificity of H2EH3, immunohistochemistry (IHC) assay was performed to validate the gene knockdown and induction of apoptosis in vivo. Tumor tissues from subcutaneous and orthotopic xenografts were collected and examined for the expression of HER2, HER3, EGFR, p21 and CC3. As shown in FIG. 17A-17O, subcutaneous tumors treated with H2EH3 through intratumoral injection have reduced protein levels of EGFR, HER2, and HER3 and increased levels of CC3 and p21 compared with PBS treated controls. Similarly, reduced expression of EGFR, HER2, and HER3 and increased expression of CC3 and p21 are visualized in orthotopic tumors treated with H2EH3 via intravenous injection (FIG. 17P-17Y). It was also shown by Western blot that EGFR is knocked down in tumor tissues treated with H2EH3 via either intratumoral or intravenous injection. These findings are consistent with in vitro results in FIG. 13Y-13BB. The histology and Western blot results suggest that H2EH3 enables intervention of EGFR/HER2/HER3 concomitantly and induces tumor cell-cycle arrest and apoptosis in vivo, which is translated into a significant suppression of tumor growth in mouse xenograft models.

Example 22: Assessment of Toxicity of H2EH3

Materials and Methods

Histology assay. Tumors and organs (spleen, lung, kidney, intestine, heart, liver and muscle) were collected from xenografts, and fixed with 4% paraformaldehyde. Sections (6 μm) were cut and mounted on the slides, and deparaffinized in xylene and ethyl alcohol. For immunohistochemistry assay, sections were incubated in 3% normal goat serum for 2 h and incubated with primary antibodies: caspase-3 (1:200), HER2 (1:800), HER3 (1:250), p21 (1:50), and EGFR (1:50). After washing, the sections were incubated with biotinylated secondary antibody (1:200) (VECTOR, Burlingame, Calif.) for 1 h. Following washing, the sections were incubated with VECTASTAIN ABC reagents for 30 min. The images were captured with Nuance fluorescence microscope with bright field imaging system.

ELISA assay. Normal human peripheral blood mononuclear cells (PBMCs) were separated with Ficoll-Plaque Plus (Stem Cell Technologies). Cells were seeded into 24-well plates at $2 \times 10^6$/well for 24 h in RPMI-1640 medium containing 10% fetal bovine serum. H2EH3 with the varying concentrations was added into cells, and cells were incubated for 48 h in 5% CO2 incubator at 37° C. The cell culture supernatant was detected with human IFNα and IL-6 ELISA kits following the manufacture's instruction.

Figure 15H:
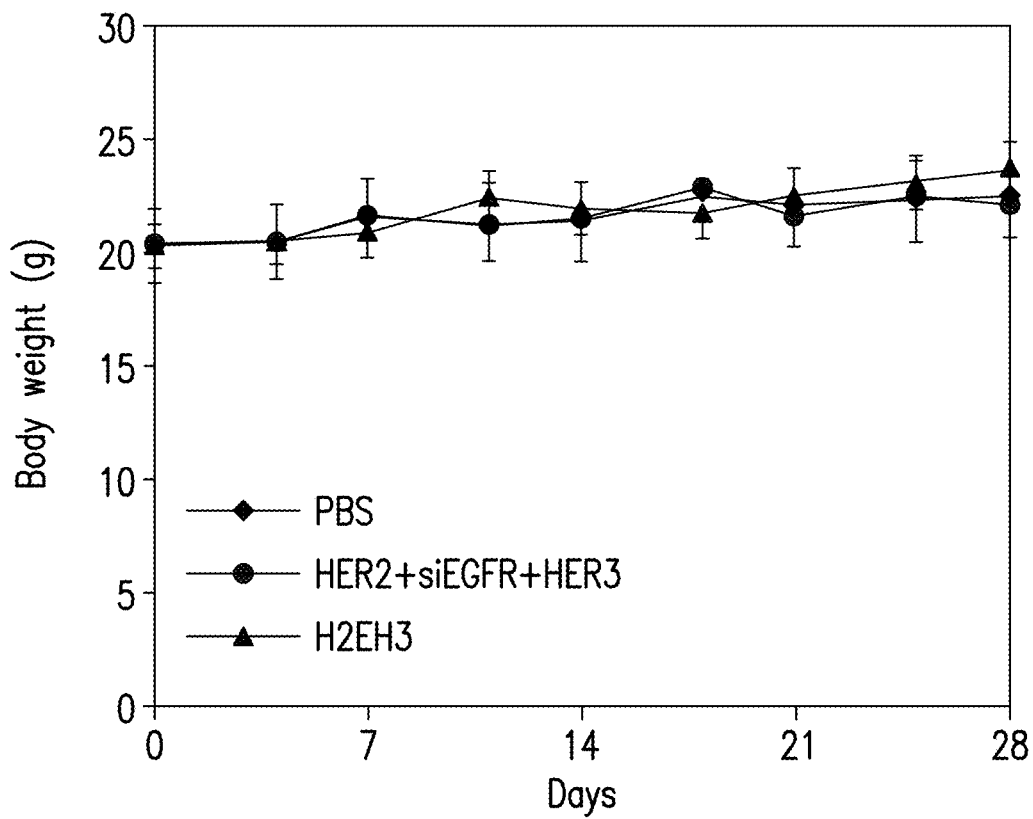
FIG. 15H is a line graph representing body weight (g) over time (days) of mice with orthotopic tumors treated with intravenous injection of PBS (◆), a mixture of HER2 aptamer and HER3 aptamer (●), or H2EH3 (▲).
Figure 16A:
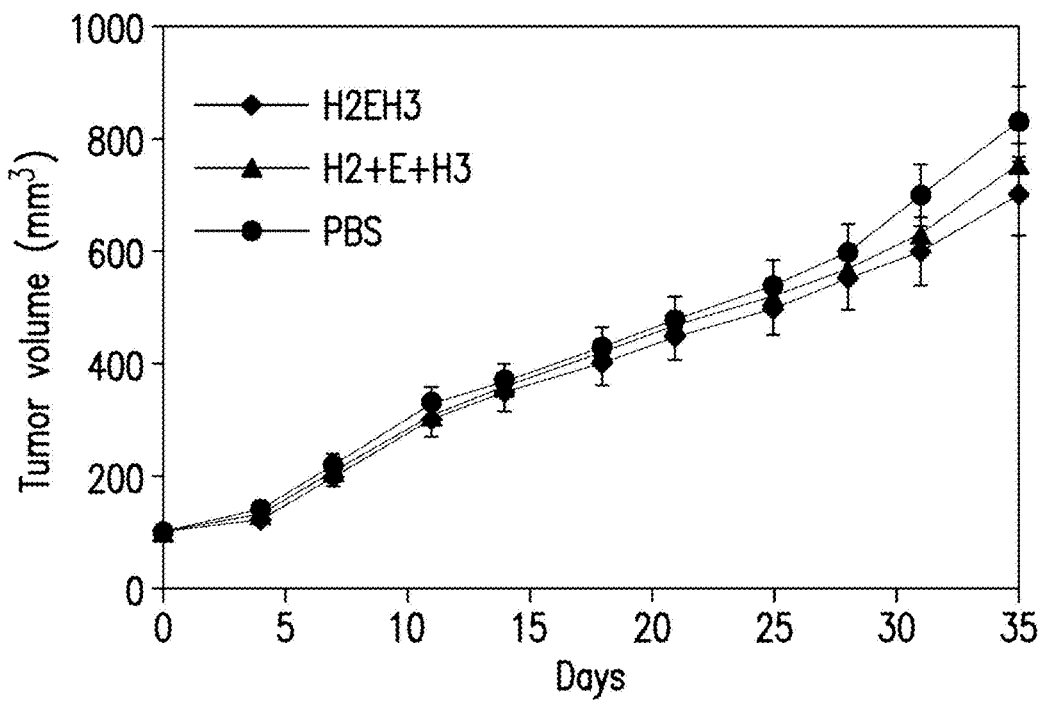
FIG. 16A is a line graph showing tumor volume (mm³) over time (days) in mice with MDA231 xenografts treated with PBS (◆), a mixture of HER2 aptamer and HER3 aptamer (●), or H2EH3 (▲).
Figure 16B:
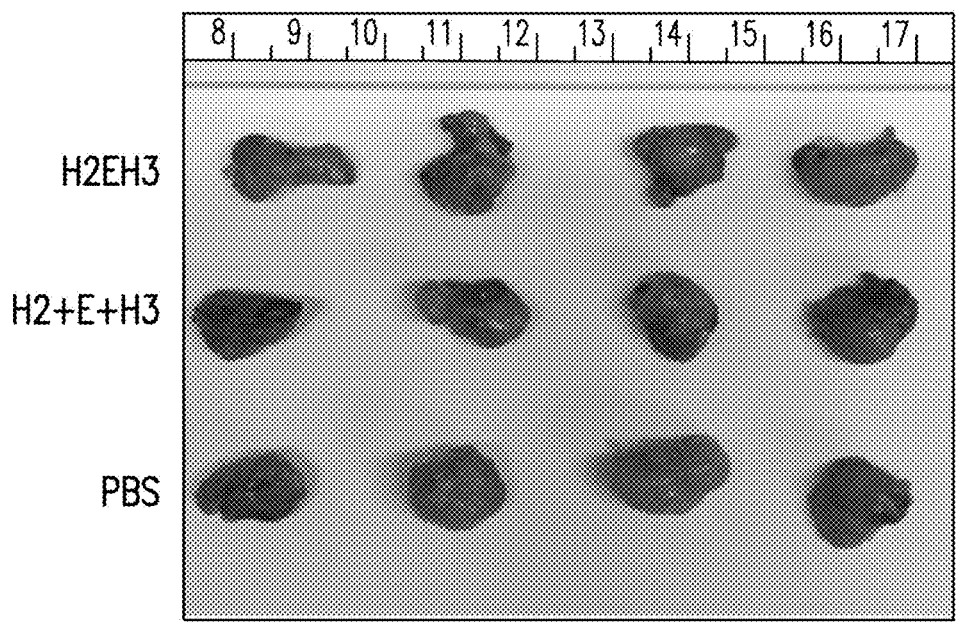
FIG. 16B shows dissected tumors from mice treated with PBS, a mixture of HER2 aptamer and HER3 aptamer, or H2EH3.
Figure 16C:
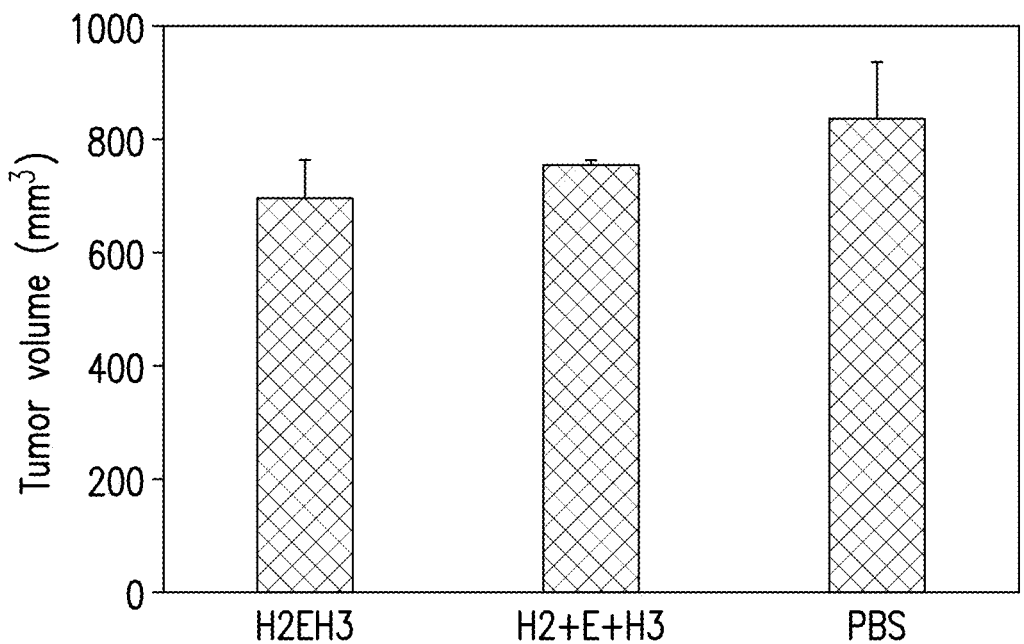
FIG. 16C is a bar graph comparing tumor volume (mm³) in mice treated with PBS, a mixture of HER2 aptamer and HER3 aptamer, or H2EH3.
Figure 16D:
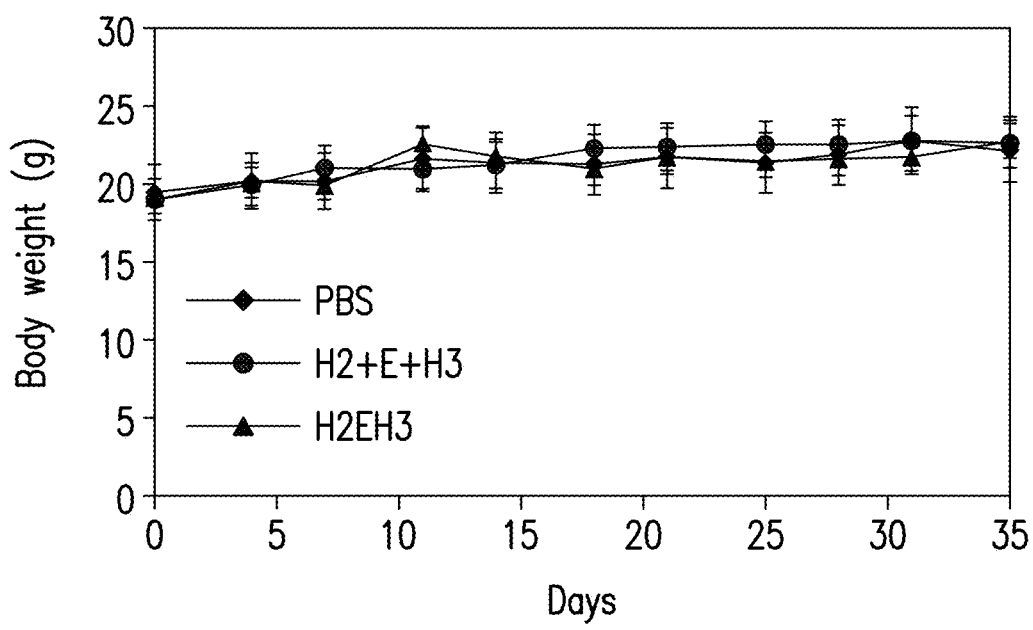
FIG. 16D is a line graph showing body weight (g) over time (days) in tumor bearing mice treated with PBS (●), a mixture of HER2 aptamer and HER3 aptamer (▲), or H2EH3 (◆).
Figure 18A:
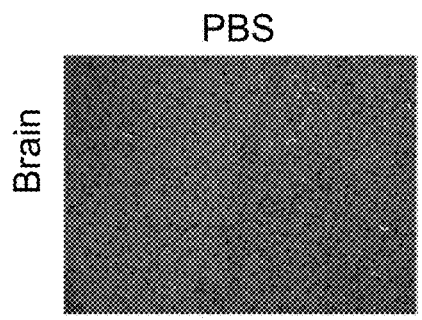
FIGS. 18A-18P are an evaluation of tissue damage in mice with orthotopic tumors treated with PBS or H2EH3.
Figure 18B:
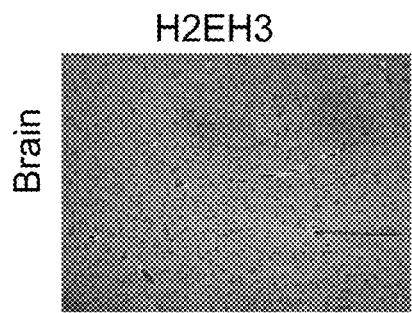
FIG. 18Q is a bar graph showing IFN-α expression (by OD450) in blood mononuclear cells from mice treated with different concentrations of H2EH3 (µM).
FIG. 18R is a bar graph showing IL-6 expression (pg/mol) in blood mononuclear cells from mice treated with different concentrations of H2EH3 (µM).
Figure 18C:
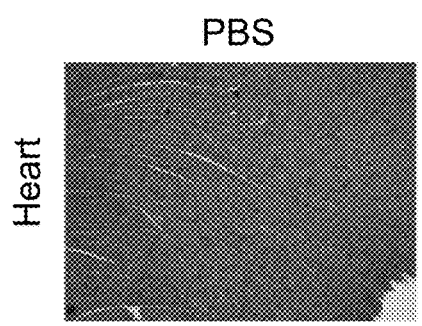
Figure 18D:
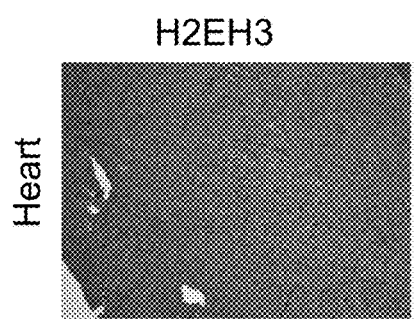
Figure 18E:
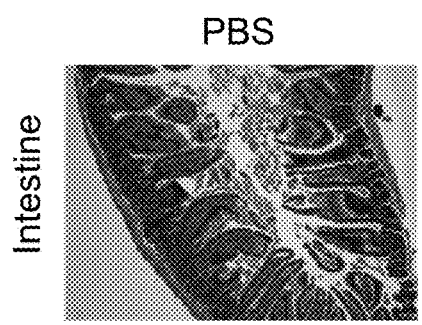
Figure 18F:
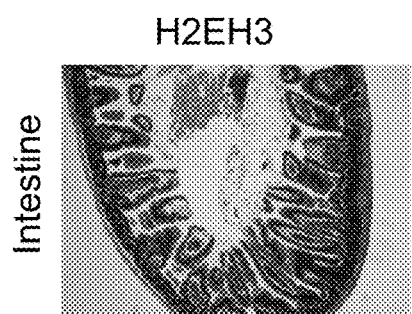
Figure 18G:
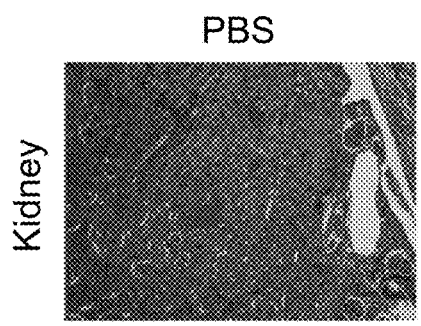
Figure 18H:
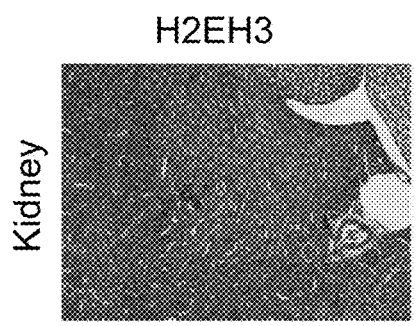
Figure 18I:
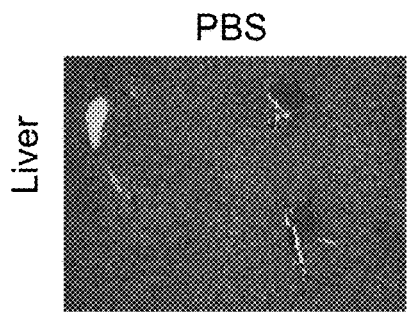
Figure 18J:
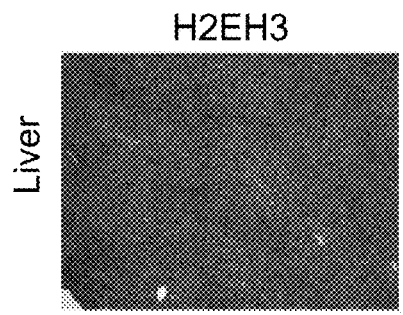
Figure 18K:
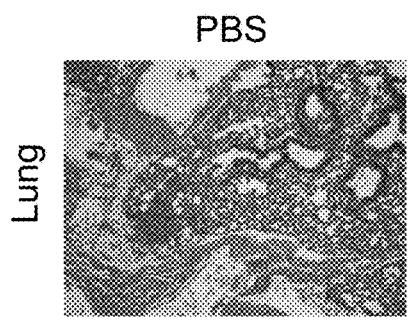
Figure 18L:
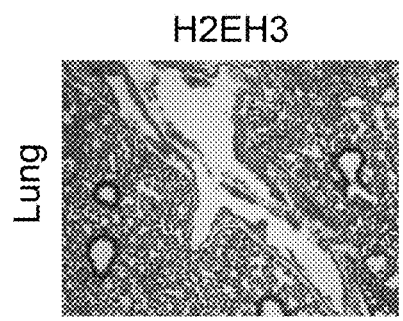
Figure 18M:
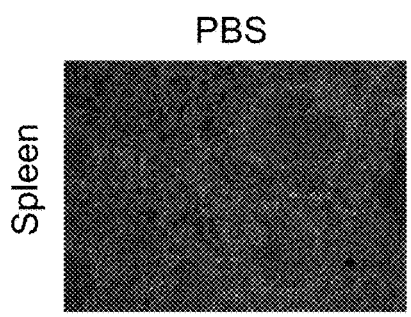
Figure 18N:
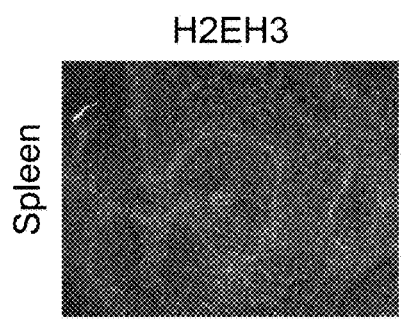
Figure 18O:
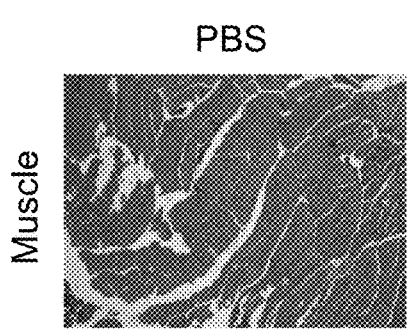
Figure 18P:
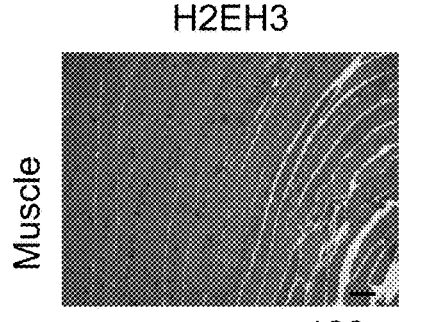
Figure 18Q:
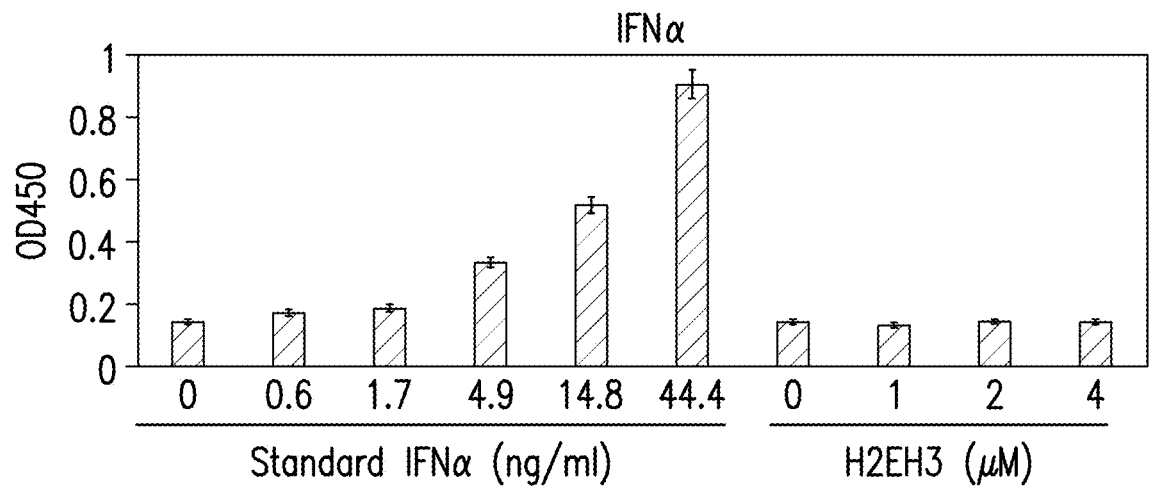
Figure 18R:
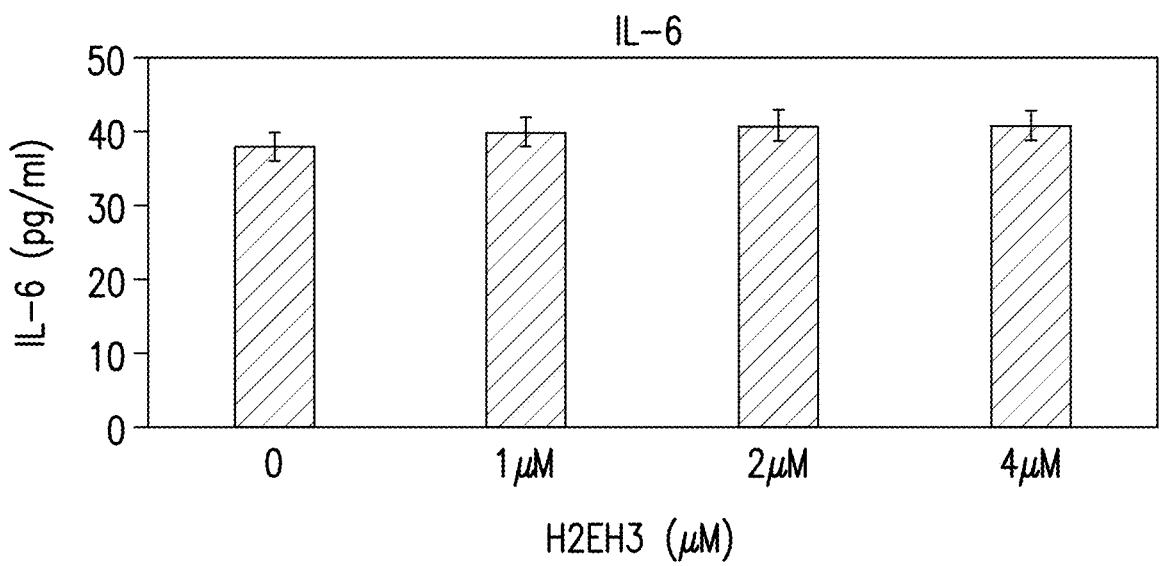

Results:

During the treatment, the body weights of mice were measured. There was no significant difference of body weights between PBS- and H2EH3-treated groups (FIGS. 15D and 15H). Furthermore, histopathology of major organs from mice that have experienced systemic drug administration by i.v injection was examined. As shown in FIG. 18A-18P, H&E staining revealed that there were no pathological changes observed in these organs from H2EH3 treated mice. Additionally, the possible innate immune response of H2EH3 by mixed lymphocyte reaction assay was detected. It was reported that RNA synthesis by transcription may induce interferon α upregulation (Kim, et al. *Nat Biotechnol*, 22: 321-325 (2004)). Human peripheral mononuclear cells (PBMCs) were treated with H2EH3 for 48 h, and then IFNα and pro-inflammatory cytokine IL-6 were measured with ELISA. As shown in FIG. 18Q, there was no detectable IFNα at the concentration up to 4 μM of H2EH3. IL-6 levels in PBMC treated with 1-4 μM of H2EH3 did not show statistical difference compared with untreated control (FIG. 18R). Taken together, these results suggest that nucleic acid-based H2EH3 has no discernible toxicity to the host and may not trigger innate immune response.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

---

I claim:

1. A pharmaceutical composition comprising an effective amount of an aptamer-siRNA chimera comprising:
   first and second ends, wherein the first and second ends comprise an aptamer that specifically binds a target protein, wherein the first end has a nucleic acid sequence according to SEQ ID NO:35, and the second end has a nucleic acid sequence according to SEQ ID NO:36; and
   an siRNA construct between the first and second ends, wherein the siRNA construct is processed by cellular RNAi machinery to produce at least two different siRNAs that specifically inhibit expression of two or more different genes in a cell expressing the target protein, wherein the siRNA construct has a nucleic acid sequence according to SEQ ID NO:37 and SEQ ID NO:38.

2. A method for reducing tumor burden in a subject in need thereof comprising, administering to the subject an effective amount of the pharmaceutical composition according to claim 1.

3. The method of claim 2, wherein the subject has breast cancer.

4. The method of claim 2, wherein the target protein of the siRNA is EGFR.

5. The method of claim 4, wherein the two or more different genes bound by the aptamers comprise HER2 and HER3 oncogene expressed by the cancer cell.

6. A method of reducing tumor associated angiogenesis in a subject in need thereof comprising:
   administering to the subject an effective amount of the pharmaceutical composition of claim 1.

7. The method of claim 2, wherein the subject has breast cancer.

* * * * *

SEQUENCE LISTING

```
<160> NUMBER OF SEQ ID NOS: 38

<210> SEQ ID NO 1
<211> LENGTH: 59
<212> TYPE: DNA
<213> ORGANISM: Artificial Sequence
<220> FEATURE:
<223> OTHER INFORMATION: Synthetic

<400> SEQUENCE: 1
agccgcgagg ggagggatag ggtagggcgc ggctaaaacc ttagcagtct tatctaatt          59

<210> SEQ ID NO 2
<211> LENGTH: 34
<212> TYPE: DNA
<213> ORGANISM: Artificial Sequence
<220> FEATURE:
<223> OTHER INFORMATION: Synthetic

<400> SEQUENCE: 2
taatacgact cactataagc cgcgagggga ggga                                     34

<210> SEQ ID NO 3
<211> LENGTH: 26
<212> TYPE: DNA
<213> ORGANISM: Artificial Sequence
<220> FEATURE:
<223> OTHER INFORMATION: Synthetic
```

<400> SEQUENCE: 3
aattagataa gactgctaag gtttta                                26

<210> SEQ ID NO 4
<211> LENGTH: 59
<212> TYPE: DNA
<213> ORGANISM: Artificial Sequence
<220> FEATURE:
<223> OTHER INFORMATION: Synthetic

<400> SEQUENCE: 4
agccgcgagg ggagggatag ggtagggcgc ggctaaaatt agataagact gctaaggca   59

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
tgccttagca gtcttatcta attttagccg cgccct                     36

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
agccgcgccc taccctatcc ct                                    22

<210> SEQ ID NO 7
<211> LENGTH: 59
<212> TYPE: DNA
<213> ORGANISM: Artificial Sequence
<220> FEATURE:
<223> OTHER INFORMATION: Synthetic

<400> SEQUENCE: 7
agccaaacga gggggagag ggtgggggcg cctgaaaacc ttagcagtct tatctaatt    59

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
taatacgact cactataagc caaacgaggg gggagagggt                 40

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
aattagataa gactgctaag gttttca                               27

<210> SEQ ID NO 10
<211> LENGTH: 59

```
<212> TYPE: DNA
<213> ORGANISM: Artificial Sequence
<220> FEATURE:
<223> OTHER INFORMATION: Synthetic

<400> SEQUENCE: 10
agccaaacga gggggagag ggtgggggcg cctgaaaatt agataagact gctaaggca      59

<210> SEQ ID NO 11
<211> LENGTH: 27
<212> TYPE: DNA
<213> ORGANISM: Artificial Sequence
<220> FEATURE:
<223> OTHER INFORMATION: Synthetic

<400> SEQUENCE: 11
tgccttagca gtcttatcta attttca                                       27

<210> SEQ ID NO 12
<211> LENGTH: 59
<212> TYPE: DNA
<213> ORGANISM: Artificial Sequence
<220> FEATURE:
<223> OTHER INFORMATION: Synthetic

<400> SEQUENCE: 12
agccaaacga gggggagag ggtgggggcg cctgaaaaaa cagtcgcgtt tgcgactgg      59

<210> SEQ ID NO 13
<211> LENGTH: 27
<212> TYPE: DNA
<213> ORGANISM: Artificial Sequence
<220> FEATURE:
<223> OTHER INFORMATION: Synthetic

<400> SEQUENCE: 13
ccagtcgcaa acgcgactgt tttttca                                       27

<210> SEQ ID NO 14
<211> LENGTH: 59
<212> TYPE: DNA
<213> ORGANISM: Artificial Sequence
<220> FEATURE:
<223> OTHER INFORMATION: Synthetic

<400> SEQUENCE: 14
agccaaacga gggggagag ggtgggggcg cctgaaaacc agtcgcaaac gcgactgtt      59

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
aacagtcgcg tttgcgactg gttttca                                       27

<210> SEQ ID NO 16
<211> LENGTH: 22
<212> TYPE: DNA
<213> ORGANISM: Artificial Sequence
<220> FEATURE:
<223> OTHER INFORMATION: Synthetic

<400> SEQUENCE: 16
```

```
ccatgccttt gagaacctag aa                                              22
```

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17

```
gagcgtaatc ccaaggatgt ta                                              22
```

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18

```
ggtgtgaacc atgagaagta tga                                             23
```

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19

```
gagtccttcc acgataccaa ag                                              22
```

<210> SEQ ID NO 20
<211> LENGTH: 104
<212> TYPE: RNA
<213> ORGANISM: Artificial Sequence
<220> FEATURE:
<223> OTHER INFORMATION: Synthetic

<400> SEQUENCE: 20

```
gaauuccgcg ugugccagcg aaaguugcgu augggucaca ucgcaggcac augucaucug     60
ggcgguccgu ucgggaucca aaauuagaua agacugcuaa ggca                     104
```

<210> SEQ ID NO 21
<211> LENGTH: 104
<212> TYPE: DNA
<213> ORGANISM: Artificial Sequence
<220> FEATURE:
<223> OTHER INFORMATION: Synthetic

<400> SEQUENCE: 21

```
gaattccgcg tgtgccagcg aaagttgcgt atgggtcaca tcgcaggcac atgtcatctg     60
ggcggtccgt tcgggatcca aaattagata agactgctaa ggca                     104
```

<210> SEQ ID NO 22
<211> LENGTH: 34
<212> TYPE: DNA
<213> ORGANISM: Artificial Sequence
<220> FEATURE:
<223> OTHER INFORMATION: Synthetic

<400> SEQUENCE: 22

```
taatacgact cactatagaa ttccgcgtgt gcca                                 34
```

```
<210> SEQ ID NO 23
<211> LENGTH: 34
<212> TYPE: DNA
<213> ORGANISM: Artificial Sequence
<220> FEATURE:
<223> OTHER INFORMATION: Synthetic

<400> SEQUENCE: 23
tgccttagca gtcttatcta attttggatc ccga                                34

<210> SEQ ID NO 24
<211> LENGTH: 59
<212> TYPE: RNA
<213> ORGANISM: Artificial Sequence
<220> FEATURE:
<223> OTHER INFORMATION: Synthetic

<400> SEQUENCE: 24
agccgcgagg ggagggauag gguagggcgc ggcuaaaacc uuagcagucu uaucuaauu     59

<210> SEQ ID NO 25
<211> LENGTH: 59
<212> TYPE: DNA
<213> ORGANISM: Artificial Sequence
<220> FEATURE:
<223> OTHER INFORMATION: Synthetic

<400> SEQUENCE: 25
agccgcgagg ggagggatag ggtagggcgc ggctaaaacc ttagcagtct tatctaatt     59

<210> SEQ ID NO 26
<211> LENGTH: 21
<212> TYPE: RNA
<213> ORGANISM: Artificial Sequence
<220> FEATURE:
<223> OTHER INFORMATION: Synthetic

<400> SEQUENCE: 26
ggaucccgaa cggaccgccc a                                              21

<210> SEQ ID NO 27
<211> LENGTH: 38
<212> TYPE: RNA
<213> ORGANISM: Artificial Sequence
<220> FEATURE:
<223> OTHER INFORMATION: Synthetic

<400> SEQUENCE: 27
ggaucccgac uggcgagagc cagguaacga auggaucc                            38

<210> SEQ ID NO 28
<211> LENGTH: 55
<212> TYPE: DNA
<213> ORGANISM: Artificial Sequence
<220> FEATURE:
<223> OTHER INFORMATION: Synthetic

<400> SEQUENCE: 28
taatacgact cactatagga tcccgactgg cgagagccag gtaacgaatg gatcc          55

<210> SEQ ID NO 29
<211> LENGTH: 31
<212> TYPE: DNA
<213> ORGANISM: Artificial Sequence
<220> FEATURE:
<223> OTHER INFORMATION: Synthetic
```

<400> SEQUENCE: 29
taatacgact cactatagga tcccgactgg c    31

<210> SEQ ID NO 30
<211> LENGTH: 17
<212> TYPE: DNA
<213> ORGANISM: Artificial Sequence
<220> FEATURE:
<223> OTHER INFORMATION: Synthetic

<400> SEQUENCE: 30
ggatccattc gttacct    17

<210> SEQ ID NO 31
<211> LENGTH: 104
<212> TYPE: DNA
<213> ORGANISM: Artificial Sequence
<220> FEATURE:
<223> OTHER INFORMATION: Synthetic

<400> SEQUENCE: 31
gaattccgcg tgtgccagcg aaagttgcgt atgggtcaca tcgcacagga cgttcatctg    60
ggcggtccgt tcgggatcca aaauuagaua agacugcuaa ggca    104

<210> SEQ ID NO 32
<211> LENGTH: 34
<212> TYPE: DNA
<213> ORGANISM: Artificial Sequence
<220> FEATURE:
<223> OTHER INFORMATION: Synthetic

<400> SEQUENCE: 32
taatacgact cactatagaa ttccgcgtgt gcca    34

<210> SEQ ID NO 33
<211> LENGTH: 59
<212> TYPE: DNA
<213> ORGANISM: Artificial Sequence
<220> FEATURE:
<223> OTHER INFORMATION: Synthetic

<400> SEQUENCE: 33
agccaaacga ggggggagag ggtgggggcg cctgaaaacc ttagcagtct tatctaatt    59

<210> SEQ ID NO 34
<211> LENGTH: 40
<212> TYPE: DNA
<213> ORGANISM: Artificial Sequence
<220> FEATURE:
<223> OTHER INFORMATION: Synthetic

<400> SEQUENCE: 34
taatacgact cactataagc caaacgaggg gggagagggt    40

<210> SEQ ID NO 35
<211> LENGTH: 34
<212> TYPE: DNA
<213> ORGANISM: Artificial Sequence
<220> FEATURE:
<223> OTHER INFORMATION: Synthetic

<400> SEQUENCE: 35
agccgcgagg ggagggauag gguagggaga ggau    34

```
<210> SEQ ID NO 36
<211> LENGTH: 79
<212> TYPE: DNA
<213> ORGANISM: Artificial Sequence
<220> FEATURE:
<223> OTHER INFORMATION: Synthetic

<400> SEQUENCE: 36
gaauuccgcg ugugccagcg aaaguugcgu augggucaca ucgcaggcac augucaucug      60
ggcgguccgu ucgggaucc                                                  79

<210> SEQ ID NO 37
<211> LENGTH: 25
<212> TYPE: DNA
<213> ORGANISM: Artificial Sequence
<220> FEATURE:
<223> OTHER INFORMATION: Synthetic

<400> SEQUENCE: 37
aaaaccttag cagtcttatc taatt                                           25

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
aaaattagat aagactgcta aggca                                           25
```